United States Patent
Arata et al.

(10) Patent No.: US 10,952,796 B2
(45) Date of Patent: Mar. 23, 2021

(54) SYSTEM AND METHOD FOR VERIFYING CALIBRATION OF A SURGICAL DEVICE

(71) Applicant: MAKO SURGICAL CORP., Ft. Lauderdale, FL (US)

(72) Inventors: Louis Arata, Mentor, OH (US); Sherif Aly, Boca Raton, FL (US); Robert Van Vorhis, Davis, CA (US); Sandi Glauser, Weston, FL (US); Timothy Blackwell, Vienna, MO (US); Rony Abovitz, Hollywood, FL (US); Maurice Ferre, Key Biscayne, FL (US)

(73) Assignee: MAKO Surgical Corp., Fort Lauderdale, FL (US)

( * ) Notice: Subject to any disclaimer, the term of this patent is extended or adjusted under 35 U.S.C. 154(b) by 421 days.

(21) Appl. No.: 15/670,906

(22) Filed: Aug. 7, 2017

(65) Prior Publication Data
US 2017/0333138 A1    Nov. 23, 2017

Related U.S. Application Data

(63) Continuation of application No. 11/750,807, filed on May 18, 2007, now Pat. No. 9,724,165.
(Continued)

(51) Int. Cl.
*A61B 34/20* (2016.01)
*A61B 90/00* (2016.01)
(Continued)

(52) U.S. Cl.
CPC ........ *A61B 34/20* (2016.02); *A61B 17/1764* (2013.01); *A61B 34/10* (2016.02);
(Continued)

(58) Field of Classification Search
CPC ..... A61B 17/1764; A61B 34/71; A61B 34/30; A61B 34/76; A61B 34/20; A61B 34/10; A61B 90/03
See application file for complete search history.

(56) References Cited

U.S. PATENT DOCUMENTS

| 4,903,536 A | 2/1990 | Salisbury et al. |
| 4,979,949 A | 12/1990 | Matsen et al. |
(Continued)

FOREIGN PATENT DOCUMENTS

| CN | 1684729 | 10/2005 |
| EP | 1 059 067 A1 | 12/2000 |
(Continued)

OTHER PUBLICATIONS

U.S. Appl. No. 10/357,197, filed Feb. 21, 2006, Quaid et al.
(Continued)

*Primary Examiner* — Sujoy K Kundu
*Assistant Examiner* — L. Anderson
(74) *Attorney, Agent, or Firm* — Foley & Lardner LLP

(57) ABSTRACT

A system for verifying a tool for use in a surgical procedure includes a mechanical interface configured to be affixed to a portion of a patient's anatomy, wherein the mechanical interface comprises at least a first portion having a first diameter and a second portion having a second diameter. The system further includes a probe configured to be inserted into the mechanical interface to establish a checkpoint location, and a computing system configured to determine a location of a portion of the probe when the probe is inserted a maximum distance into the mechanical interface, wherein the location of the portion of the probe establishes the checkpoint location. The computing system is further configured to verify a surgical tool by comparing the checkpoint location to a location of a portion of the surgical tool
(Continued)

when the surgical tool is inserted a maximum distance into the mechanical interface.

20 Claims, 28 Drawing Sheets

Related U.S. Application Data

(60) Provisional application No. 60/801,378, filed on May 19, 2006.

(51) Int. Cl.
  *A61B 34/30* (2016.01)
  *A61B 17/17* (2006.01)
  *A61B 34/00* (2016.01)
  *A61B 34/10* (2016.01)
  *A61B 17/00* (2006.01)

(52) U.S. Cl.
  CPC .............. *A61B 34/30* (2016.02); *A61B 34/71* (2016.02); *A61B 34/76* (2016.02); *A61B 90/03* (2016.02); *A61B 34/25* (2016.02); *A61B 2017/00119* (2013.01); *A61B 2017/00694* (2013.01); *A61B 2017/00712* (2013.01); *A61B 2017/00725* (2013.01); *A61B 2034/102* (2016.02); *A61B 2034/107* (2016.02); *A61B 2034/108* (2016.02); *A61B 2034/207* (2016.02); *A61B 2034/2055* (2016.02); *A61B 2034/2059* (2016.02); *A61B 2034/2065* (2016.02); *A61B 2034/2068* (2016.02); *A61B 2034/2072* (2016.02); *A61B 2034/305* (2016.02); *A61B 2090/363* (2016.02); *A61B 2090/364* (2016.02); *A61B 2090/3983* (2016.02)

(56) References Cited

U.S. PATENT DOCUMENTS

| | | |
|---|---|---|
| 5,046,375 A | 9/1991 | Salisbury et al. |
| 5,086,401 A | 2/1992 | Glassman et al. |
| 5,142,930 A | 9/1992 | Allen et al. |
| 5,154,717 A | 10/1992 | Matsen et al. |
| 5,207,114 A | 5/1993 | Salisbury et al. |
| 5,230,338 A | 7/1993 | Allen et al. |
| 5,236,432 A | 8/1993 | Matsen et al. |
| 5,299,288 A | 3/1994 | Glassman et al. |
| 5,343,385 A | 8/1994 | Joskowicz et al. |
| 5,383,901 A * | 1/1995 | McGregor ....... A61B 17/06066 606/223 |
| 5,388,480 A | 2/1995 | Townsend |
| 5,399,951 A | 3/1995 | Lavallee et al. |
| 5,408,409 A | 4/1995 | Glassman et al. |
| 5,445,144 A | 8/1995 | Wodicka et al. |
| 5,445,166 A | 8/1995 | Taylor |
| 5,452,941 A | 9/1995 | Halse et al. |
| 5,551,429 A | 9/1996 | Fitzpatrick et al. |
| 5,572,999 A | 11/1996 | Funda et al. |
| 5,576,727 A | 11/1996 | Rosenberg et al. |
| 5,587,937 A | 12/1996 | Massie et al. |
| 5,611,353 A | 3/1997 | Dance et al. |
| 5,625,576 A | 4/1997 | Massie et al. |
| 5,630,431 A | 5/1997 | Taylor |
| 5,638,819 A | 6/1997 | Manwaring et al. |
| 5,676,673 A | 10/1997 | Ferre et al. |
| 5,682,886 A | 11/1997 | Delp et al. |
| 5,688,280 A | 11/1997 | Booth et al. |
| 5,694,013 A | 12/1997 | Stewart et al. |
| 5,695,500 A | 12/1997 | Taylor et al. |
| 5,701,140 A | 12/1997 | Rosenberg et al. |
| 5,704,791 A | 1/1998 | Gillio |
| 5,727,554 A | 3/1998 | Kalend et al. |
| 5,792,147 A | 8/1998 | Evans et al. |
| 5,799,055 A | 8/1998 | Peshkin et al. |
| 5,806,518 A | 9/1998 | Mittelstadt |
| 5,831,408 A | 11/1998 | Jacobus et al. |
| 5,855,553 A | 1/1999 | Tajima et al. |
| 5,871,018 A | 2/1999 | Delp et al. |
| 5,887,121 A | 3/1999 | Funda et al. |
| 5,888,220 A | 3/1999 | Felt et al. |
| 5,898,599 A | 4/1999 | Massie et al. |
| 5,928,137 A | 7/1999 | Green |
| 5,950,629 A | 9/1999 | Taylor et al. |
| 5,971,997 A | 10/1999 | Guthrie et al. |
| 5,976,156 A | 11/1999 | Taylor et al. |
| 5,978,696 A | 11/1999 | Vomlehn et al. |
| 5,980,535 A | 11/1999 | Barnett et al. |
| 5,984,930 A | 11/1999 | Maciunas et al. |
| 5,987,960 A | 11/1999 | Messner et al. |
| 6,002,859 A | 12/1999 | DiGioia, III et al. |
| 6,006,126 A | 12/1999 | Cosman |
| 6,006,127 A | 12/1999 | Van Der Brug et al. |
| 6,017,305 A | 1/2000 | Bonutti |
| 6,033,415 A | 3/2000 | Mittelstadt et al. |
| 6,084,587 A | 7/2000 | Tarr et al. |
| 6,104,158 A | 8/2000 | Jacobus et al. |
| 6,109,270 A | 8/2000 | Mah et al. |
| 6,111,577 A | 8/2000 | Zilles et al. |
| 6,147,674 A | 11/2000 | Rosenberg et al. |
| 6,161,032 A | 12/2000 | Acker |
| 6,188,728 B1 | 2/2001 | Hurst |
| 6,191,796 B1 | 2/2001 | Tarr |
| 6,205,411 B1 | 3/2001 | DiGioia, III et al. |
| 6,219,032 B1 | 4/2001 | Rosenberg et al. |
| 6,223,100 B1 | 4/2001 | Green |
| 6,226,566 B1 | 5/2001 | Funda et al. |
| 6,228,089 B1 | 5/2001 | Wahrburg |
| 6,231,526 B1 | 5/2001 | Taylor et al. |
| 6,233,504 B1 | 5/2001 | Das et al. |
| 6,259,806 B1 | 7/2001 | Green |
| 6,285,902 B1 | 9/2001 | Kienzle et al. |
| 6,288,705 B1 | 9/2001 | Rosenberg et al. |
| 6,292,174 B1 | 9/2001 | Mallett et al. |
| 6,300,936 B1 | 10/2001 | Braun et al. |
| 6,322,467 B1 | 11/2001 | Hook et al. |
| 6,322,567 B1 | 11/2001 | Mittelstadt et al. |
| 6,325,808 B1 | 12/2001 | Bernard et al. |
| 6,337,994 B1 | 1/2002 | Stoianovici et al. |
| 6,366,273 B1 | 4/2002 | Rosenberg et al. |
| 6,369,834 B1 | 4/2002 | Zilles et al. |
| 6,377,011 B1 | 4/2002 | Ben-Ur |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,393,340 B2 | 5/2002 | Funda et al. |
| 6,405,072 B1 | 6/2002 | Cosman |
| 6,405,158 B1 | 6/2002 | Massie et al. |
| 6,417,638 B1 | 7/2002 | Guy et al. |
| 6,421,048 B1 | 7/2002 | Shih et al. |
| 6,424,885 B1 | 7/2002 | Niemeyer et al. |
| 6,430,434 B1 | 8/2002 | Mittelstadt |
| 6,434,416 B1 | 8/2002 | Mizoguchi et al. |
| 6,443,894 B1 | 9/2002 | Sumanaweera et al. |
| 6,466,815 B1 | 10/2002 | Saito et al. |
| 6,468,265 B1 | 10/2002 | Evans et al. |
| 6,493,608 B1 | 12/2002 | Niemeyer |
| 6,494,039 B2 | 12/2002 | Pratt et al. |
| 6,533,737 B1 | 3/2003 | Brosseau et al. |
| 6,546,277 B1 | 4/2003 | Franck et al. |
| 6,547,782 B1 | 4/2003 | Taylor |
| 6,551,325 B2 | 4/2003 | Neubauer et al. |
| 6,552,722 B1 | 4/2003 | Shih et al. |
| 6,583,161 B1 | 6/2003 | Medina |
| 6,642,686 B1 | 11/2003 | Ruch |
| 6,671,651 B2 | 12/2003 | Goodwin et al. |
| 6,674,916 B1 | 1/2004 | Deman et al. |
| 6,690,964 B2 | 2/2004 | Bieger et al. |
| 6,692,485 B1 | 2/2004 | Brock et al. |
| 6,701,174 B1 | 3/2004 | Krause et al. |
| 6,704,694 B1 | 3/2004 | Basdogan et al. |
| 6,711,431 B2 | 3/2004 | Sarin et al. |

(56) References Cited

U.S. PATENT DOCUMENTS

| | | |
|---|---|---|
| 6,711,432 B1 | 3/2004 | Krause et al. |
| 6,748,819 B2 | 6/2004 | Maeguchi et al. |
| 6,750,877 B2 | 6/2004 | Rosenberg et al. |
| 6,757,582 B2 | 6/2004 | Brisson et al. |
| 6,778,850 B1 | 8/2004 | Adler et al. |
| 6,785,572 B2 | 8/2004 | Yanof et al. |
| 6,786,896 B1 | 9/2004 | Madhani et al. |
| 6,801,801 B1 | 10/2004 | Sati |
| 6,810,281 B2 | 10/2004 | Brock et al. |
| 6,816,148 B2 | 11/2004 | Mallett et al. |
| 6,831,640 B2 | 12/2004 | Shih et al. |
| 6,850,794 B2 | 2/2005 | Shahidi |
| 6,853,965 B2 | 2/2005 | Massie et al. |
| 6,859,661 B2 | 2/2005 | Tuke |
| 6,877,239 B2 | 4/2005 | Leitner et al. |
| 6,894,678 B2 | 5/2005 | Rosenberg et al. |
| 6,920,347 B2 | 7/2005 | Simon et al. |
| 6,985,133 B1 | 1/2006 | Rodomista et al. |
| 6,987,504 B2 | 1/2006 | Rosenberg et al. |
| 7,001,346 B2 | 2/2006 | White |
| 7,035,716 B2 | 4/2006 | Harris et al. |
| 7,039,866 B1 | 5/2006 | Rosenberg et al. |
| 7,131,073 B2 | 10/2006 | Rosenberg et al. |
| 7,168,042 B2 | 1/2007 | Braun et al. |
| 7,199,790 B2 | 4/2007 | Rosenberg et al. |
| 7,206,626 B2 | 4/2007 | Quaid, III |
| 7,206,627 B2 | 4/2007 | Abovitz et al. |
| 7,491,198 B2 | 2/2009 | Kockro |
| 7,660,623 B2 | 2/2010 | Hunter et al. |
| 7,717,932 B2 | 5/2010 | McFarlin et al. |
| 7,742,804 B2 | 6/2010 | Faul |
| 7,747,311 B2 | 6/2010 | Quaid, III |
| 7,774,044 B2 | 8/2010 | Sauer et al. |
| 7,831,292 B2 | 11/2010 | Quaid et al. |
| 8,391,954 B2 | 3/2013 | Quaid, III |
| 8,911,499 B2 | 12/2014 | Quaid et al. |
| 9,002,426 B2 | 4/2015 | Quaid et al. |
| 9,492,237 B2 | 11/2016 | Kang et al. |
| 2001/0034530 A1 | 10/2001 | Malackowski et al. |
| 2001/0037064 A1 | 11/2001 | Shahidi |
| 2001/0039422 A1 | 11/2001 | Carol et al. |
| 2001/0041838 A1 | 11/2001 | Holupka et al. |
| 2002/0062177 A1 | 5/2002 | Hannaford et al. |
| 2002/0082498 A1 | 6/2002 | Wendt et al. |
| 2002/0107521 A1 | 8/2002 | Petersen et al. |
| 2002/0108054 A1 | 8/2002 | Moore et al. |
| 2002/0120188 A1 | 8/2002 | Brock et al. |
| 2003/0093103 A1 | 5/2003 | Malackowski et al. |
| 2003/0112281 A1 | 6/2003 | Sriram et al. |
| 2003/0187351 A1 | 10/2003 | Franck et al. |
| 2003/0209096 A1 | 11/2003 | Pandey et al. |
| 2004/0009459 A1 | 1/2004 | Anderson et al. |
| 2004/0012806 A1 | 1/2004 | Murata |
| 2004/0024311 A1 | 2/2004 | Quaid, III |
| 2004/0034282 A1 | 2/2004 | Quaid et al. |
| 2004/0034283 A1 | 2/2004 | Quaid |
| 2004/0034302 A1 | 2/2004 | Abovitz et al. |
| 2004/0102866 A1 | 5/2004 | Harris et al. |
| 2004/0106916 A1 | 6/2004 | Quaid et al. |
| 2004/0115606 A1 | 6/2004 | Davies |
| 2004/0127788 A1 | 7/2004 | Arata |
| 2004/0128026 A1 | 7/2004 | Harris et al. |
| 2004/0157188 A1 | 8/2004 | Luth et al. |
| 2004/0167654 A1 | 8/2004 | Grimm et al. |
| 2004/0171924 A1 | 9/2004 | Mire et al. |
| 2004/0236424 A1 | 11/2004 | Berez et al. |
| 2005/0001831 A1 | 1/2005 | Shih et al. |
| 2005/0062738 A1 | 3/2005 | Handley et al. |
| 2005/0093821 A1 | 5/2005 | Massie et al. |
| 2005/0107801 A1 | 5/2005 | Davies et al. |
| 2005/0113677 A1 | 5/2005 | Davies et al. |
| 2005/0154471 A1 | 7/2005 | Aram et al. |
| 2005/0165489 A1 | 7/2005 | Michelson |
| 2005/0197800 A1 | 9/2005 | Goodwin et al. |
| 2005/0203384 A1 | 9/2005 | Sati et al. |
| 2005/0215879 A1 | 9/2005 | Chuanggui |
| 2005/0215888 A1 | 9/2005 | Grimm et al. |
| 2005/0217394 A1 | 10/2005 | Langley et al. |
| 2005/0222830 A1 | 10/2005 | Massie et al. |
| 2006/0033707 A1 | 2/2006 | Rodomista et al. |
| 2006/0058616 A1 | 3/2006 | Marquart et al. |
| 2006/0084867 A1 | 4/2006 | Tremblay et al. |
| 2006/0109266 A1 | 5/2006 | Itkowitz et al. |
| 2006/0133827 A1 | 6/2006 | Becouarn et al. |
| 2006/0142657 A1 | 6/2006 | Quaid et al. |
| 2006/0207419 A1 | 9/2006 | Okazaki et al. |
| 2006/0265179 A1 | 11/2006 | Jansen et al. |
| 2006/0293598 A1 | 12/2006 | Fraser |
| 2007/0142751 A1 | 6/2007 | Kang et al. |
| 2007/0260140 A1 | 11/2007 | Solar et al. |
| 2008/0004633 A1 | 1/2008 | Arata et al. |
| 2008/0010705 A1 | 1/2008 | Quaid et al. |
| 2008/0010706 A1 | 1/2008 | Moses et al. |
| 2008/0058945 A1 | 3/2008 | Hajaj et al. |
| 2009/0000626 A1 | 1/2009 | Quaid et al. |
| 2009/0000627 A1 | 1/2009 | Quaid et al. |
| 2009/0012531 A1 | 1/2009 | Quaid et al. |
| 2009/0012532 A1 | 1/2009 | Quaid et al. |
| 2010/0170362 A1 | 7/2010 | Bennett et al. |
| 2010/0198219 A1 | 8/2010 | McFarlin et al. |
| 2010/0225209 A1 | 9/2010 | Goldberg et al. |
| 2011/0130761 A1* | 6/2011 | Plaskos ............ A61B 17/155 606/87 |
| 2011/0270120 A1 | 11/2011 | McFarlin et al. |
| 2012/0176306 A1 | 7/2012 | Lightcap et al. |
| 2013/0096573 A1 | 4/2013 | Kang et al. |
| 2013/0096574 A1 | 4/2013 | Kang et al. |
| 2014/0350571 A1 | 11/2014 | Maillet et al. |

FOREIGN PATENT DOCUMENTS

| | | |
|---|---|---|
| EP | 1 184 684 A2 | 3/2002 |
| EP | 1 380 266 A1 | 1/2004 |
| EP | 1 871 267 | 1/2008 |
| EP | 1 574 186 | 6/2008 |
| JP | 08-215211 A | 8/1996 |
| JP | 09-330016 A | 12/1997 |
| JP | 2000-279425 A | 10/2000 |
| JP | 2002-102251 | 4/2002 |
| JP | 2003-053684 | 2/2003 |
| JP | 2004-513684 | 5/2004 |
| WO | WO-95/01757 A1 | 1/1995 |
| WO | WO-96/17552 A1 | 6/1996 |
| WO | WO-00/35336 A2 | 6/2000 |
| WO | WO-02/24051 A2 | 3/2002 |
| WO | WO-02/060653 A2 | 8/2002 |
| WO | WO-02/061371 A1 | 8/2002 |
| WO | WO-03/007101 | 1/2003 |
| WO | WO-03/077101 A2 | 9/2003 |
| WO | WO-2004/069036 A2 | 8/2004 |
| WO | WO-2004/069040 A2 | 8/2004 |
| WO | WO-2004/069041 A2 | 8/2004 |
| WO | WO-2004/070573 A2 | 8/2004 |
| WO | WO-2004/070577 A1 | 8/2004 |
| WO | WO-2004/070580 A2 | 8/2004 |
| WO | WO-2004/070581 A2 | 8/2004 |
| WO | WO-2004/075987 A1 | 9/2004 |
| WO | WO-2005/009215 A2 | 2/2005 |
| WO | WO-2005/013841 | 2/2005 |
| WO | WO-2005/072629 A1 | 8/2005 |
| WO | WO-2005/120380 A1 | 12/2005 |
| WO | WO-2005/122916 A1 | 12/2005 |
| WO | WO-2006/004894 A2 | 1/2006 |
| WO | WO-2006/091494 A1 | 8/2006 |
| WO | WO-2007/117297 A2 | 10/2007 |

OTHER PUBLICATIONS

U.S. Appl. No. 10/384,072, filed Mar. 6, 2003, Quaid, III.
U.S. Appl. No. 10/384,077, filed Mar. 6, 2003, Abovitz et al.
U.S. Appl. No. 10/384,078, filed Mar. 6, 2003, Quaid, III.
U.S. Appl. No. 10/384,194, filed Mar. 6, 2003, Quaid, III.
U.S. Appl. No. 10/621,119, filed Jul. 16, 2003, Quaid et al.

(56) References Cited

OTHER PUBLICATIONS

U.S. Appl. No. 11/646,204, filed Dec. 27, 2006, Kang et al.
U.S. Appl. No. 11/750,815, filed May 18, 2007, Kang et al.
U.S. Appl. No. 12/144,496, filed Jun. 23, 2008, Quaid et al.
U.S. Appl. No. 12/144,507, filed Jun. 23, 2008, Quaid et al.
U.S. Appl. No. 12/144,517, filed Jun. 23, 2008, Quaid et al.
U.S. Appl. No. 12/144,526, filed Jun. 23, 2008, Quaid et al.
U.S. Appl. No. 12/698,353, filed Feb. 2, 2010, Quaid, III.
Abovitz et al., "The Future Use of Networked Haptic Learning Information Systems in Computer-Assisted Surgery," CAOS 2001, Jul. 6-8, 2001, pp. 337-338.
Abovitz, "Digital surgery: the future of medicine and human-robot symbiotic interaction," Industrial Robot: An International Journal, Oct. 2001, vol. 28, Issue 5, pp. 401-406 (abstract only).
Abovitz, "Human-Interactive Medical Robotics," CAOS 2000, Jun. 15-17, 2000, pp. 71-72.
Abovitz, "Human-Interactive Medical Robotics," CAOS 2001, Jul. 6-8, 2001, pp. 81-82.
Acosta, et al., "Development of a Haptic Virtual Environment", Computer-Based Medical Systems, Proceedings 12th IEEE Symposium. pp. 35-39, 1999.
Bennett et al., "Autonomous Calibration of Single-Loop Kinematic Chains Formed by Manipulators With Passive End-Point Constraints," IEEE Transactions on Robotics and Automation, vol. 7, pp. 597-606, 1991.
Bettini et al., "Vision assisted control for manipulation using virtual fixtures: Experiments at macro and micro scales," in Proc. 2002 IEEE Intl. Conf. on Robotics and Automation, (Washington, DC), May 2002, 8 pages.
Chapter II Demand and Response to Written Opinion for PCT/US2006/005700, dated Dec. 15, 2006, 16 pages.
Chapter II Demand and Response to Written Opinion for PCT/US2006/049216, dated Jul. 15, 2008, 19 pages.
Chen et al., "Force Feedback for Surgical Simulation," Proceedings of the IEEE, New York, US, vol. 86, No. 3, Mar. 1, 1998. pp. 524-530.
Cobb et al., "A robotic system for TKR surgery," in Third Annual North American Program on Computer Assisted Orthopaedic Surgery, (Pittsburgh, PA), pp. 70-74, Jun. 1999.
Colgate, J. Edward, et al., "Cobots: Robots for Collaboration with Human Operators," proceedings of International Mechanical Engineering Congress & Exhibition, DSC—vol. 58, 1996, pp. 433-439.
Davies et al, "Acrobot-using Robots and Surgeons Synergistically in Knee Surgery", 1997 British Crown Copyright, pp. 173-178.
Davies et al., "The use of force control in robot assisted knee surgery," in Proceedings of the First Annual Symposium on Medical Robotics and Computer Assisted Surgery, vol. 2, (Pittsburgh, PA), pp. 258-262, Sep. 1994.
Decision to Refuse a European Patent Application for EP Application No. 07756266.8 dated Aug. 3, 2016, 32 pages.
Examination report for EP 04757075.9, dated Jan. 12, 2011, 5 pages.
Fritz, et al., "Design of a Haptic Data Visualization System for People with Visual Impairments", IEEE Trans. on Rehabiliation Engineering, vol. 7, No. 3, Sep. 1999, 13 pages.
Germano et al., Clinical Use of the Optical Digitizer for Intracranial Neuronavigation, Neurosurgery, vol. 45(2), Aug. 1999, 15 pages.
Goswami, et al., "Identifying Robot Parameters Using Partial Pose Information," IEEE Control Systems Magazine, vol. 13, No. 5, Oct. 1993, 11 pages.
Ho, S.C. et al., "Robot Assisted Knee Surgery Establishing a Force Control Strategy Incorporating Active Motion Constraint," IEEE Engineering in Medicine and Biology Magazine, vol. 14, No. 3, May 1, 1995, col. 2-3, p. 293.
Hollerbach, J.M. & D. E. Johnson. Virtual Environment Rendering. To appear in Human and Machine Haptics, M. Cutkosky, R. Howe, K. Salisbury, and M. Srinivasan (eds.), MIT Press, 2000 (available at http://www.cs.ubc.ca/labs/spin/publications/related/hollerbach00.pdf), 25 pages.

International Preliminary Examination Report for PCT/US2003/007063, dated Sep. 2, 2004 (2 pages).
International Preliminary Report on Patentability for PCT/US2004/022978 including International Search Report and Written Opinion, dated Feb. 13, 2007 (6 pages).
International Preliminary Report on Patentability for PCT/US2006/005700, dated May 8, 2007 (7 pages).
International Preliminary Report on Patentability for PCT/US2006/049216, dated Sep. 10, 2008, 9 pages.
International Search Report and Written Opinion for corresponding PCT Application no. PCT/US2006/049216, dated May 8, 2008 (15 pgs.).
International Search Report and Written Opinion for PCT/US2006/005700, dated Jun. 27, 2006, 10 pages.
International Search Report for PCT/US2003/007063, dated Apr. 16, 2004 (7 pages).
Kanazides, Peter et al., "An Integrated System for Cementless Hip Replacement", Integrated Surgical Systems Department of Orthopedic Surgery, Sutter General Hospital, May/Jun. 1995, pp. 307-313.
Leeser et al., "Computerassisted teach and play: Novel user-friendly robot teach mode using gravity compensation and backdrivability," in Proceedings of the Robotics International/SME Fifth World Conference on Robotics Research, (Cambridge, MA), Sep. 1994, 7 pages.
Leeser, Karl, et al., "Control and Exploitation of Kinematic Redundancy in Torque-Controllable Manipulators via Multiple-Jacobian Superposition," to the International Conf. on Field & Service Robotics, Dec. 8-10, 1997, 7 pages.
London Press Services, "Acrobot capable of delicate knee surgery," Can. Med. Assoc. J., Jun. 15, 1997, 156(12), p. 1690.
Matsuoka, Yoky, et al., "Design of Life-Size Haptic Environments," Experimental Robotics VII, 2001, pp. 461-470.
Meggiolaro, et al., "Manipulator calibration using a single endpoint contact constraint," in 26th ASME Bienniel Mechanisms Conference, (Baltimore, MD), 2000, 9 pages.
Moore, Carl A., et al., "Cobot Implementation of 3D Virtual Surfaces," proceedings of the 2002 Institute of Electrical and Electronics Engineers International Conference on Robotics & Automation, May 2002, pp. 3242-3247.
Niki, et al., "Simple Haptic Display and Object Data Design", Proceedings of the 2000 IEEE/RSJ International Conference on Intelligent Robots and Systems, pp. 967-972, 2000.
Otmane, S., et al., "Active Virtual Guides as an Apparatus for Augmented Reality Based Telemanipulation System on the Internet," presented at Institute of Electrical and Electronics Engineers Computer Society 33rd Annual Simulation Symposium ANSS 2000, held Apr. 16-20, 2000, pp. 185-191.
Park et al., "Virtual fixtures for robotic cardiac surgery," in Proc. Medical Image Computing and Computer-Assisted Intervention, (Utrecht, Netherlands), Oct. 2001, 2 pages.
PCT/US2006/049216, Partial Intl. Search Report, dated Jan. 18, 2008 (2 pgs.).
Press Release, "The Acrobot Company Wins Best Surgical Innovation Award," Acrobot Precision Surgical Systems, May 24, 2002, 1 page.
Provision of the Minutes in Accordance with Rule 124(4) EPC for EP Application No. 07756266.8 dated Aug. 2, 2016, 5 pages.
Quaid et al., "Haptic Information Displays for Computer-Assisted Surgery," Proceedings of the 2002 IEEE International Conference on Robotics & Automation, May 2002, pp. 2092-2097.
Quaid, Arthur E., et al., "FGS WAM: First Cadaver Trial," Z-Kat, Inc. Confidential Material, Sep. 28, 2001, pp. 1-7.
Quaid, Arthur E., et al., "FGS WAM: Integration of Fluorotactic Guidance with the Whole-Arm Manipulator," Z-Kat, Inc. Confidential Material, Dec. 28, 2000, pp. 1-6.
Quaid, et al., "The Use of Haptic Information Displays for Assisting in the Execution of Image-Guided Surgery Plans," Syllabus of the Computer Assisted Orthopaedic Surgery Meeting, Jul. 2001, pp. 338-340.
Roche, "Changing the way surgeons plan and execute minimally invasive unicompartmental knee surgery," Orthopaedic Product News, pp. 16-18, Jul./Aug. 2006.

(56) References Cited

OTHER PUBLICATIONS

Rosenberg, "Virtual Fixtures: Perceptual Tools for Telerobotic Manipulation", 1993 IEEE, 76-82.
Rosenberg, Virtual Fixtures: Perceptual overlays enhance operator performance in telepresence tasks. PhD thesis, Stanford University, Aug. 1994, 7 pages.
Sayers, Craig P., et al., "An Operator Interface for Teleprogramming Employing Synthetic Fixtures," to appear in Presence, Special Issue on Networked Virtual Environments and Teleoperation, Jun. 1994, pp. 1-27.
Schneider, O., et al., "Synergistic Robotic Assistance to Cardiac Procedures," presented to Computer Assisted Radiology and Surgery on Jun. 23-26, 1999, 5 pages.
Sensable Technologies, Inc., "Freeform Feel the Difference", 2001, 4 pages.
Sensable Technologies, Inc., "FreeForm Modeling—Technical Features," 2003, 2 pages.
Staecker et al., "Use of the LandmarX (tm) Surgical Navigation System in Lateral Skull Base and Temporal Bone Surgery", SkullBase, vol. 11, No. 4, 2001, pp. 245-255; Thieme Medical Publishers, Inc. 11 pages.
Taylor, Russell et al., "An Image-Directed Robotic System for Precise Orthopaedic Surgery", IEEE Transactions on Robotics and Automation, vol. 10, No. 3, Jun. 1994, pp. 261-275.
Taylor, Russell et al., "Redundant Consistency Checking in a Precise Surgical Robot", Annual International Conference of the IEEE Engineering in Medicine and Biology Society, vol. 12, No. 5, 1990, pp. 1933-1935.
Taylor, Russell et al., "Robotic Joint Replacement Surgery", NSF Engineering Research Center for Computer-Integrated Surgical Systems and Technology, 2000, 2001, 2004, 71 pages.
Tognetti, Lawrence Joseph, "Actuator Design for a Passive Haptic Display," Georgia Institute of Technology, Jun. 1999, 33 pages.
Townsend et al., "Teleoperator slave—WAM design methodology," Industrial Robot, vol. 26, No. 3, pp. 167-177, 1999.
World Wide Web, http://haptics.me.jhu.edu/r.sub.--hapt.html, "Haptic Interfaces and Virtual Environments," printed on Jun. 12, 2003, 2 pages.
World Wide Web, http://haptics.me.jhu.edu/r.sub.--kine.html, "Robot Design and Kinematics," printed on Jun. 12, 2003, 2 pages.
World Wide Web, http://www.acrobot.co.uk/background.html, "The Acrobot Company Limited—Background," printed on Jul. 10, 2002, 1 page.
World Wide Web, http://www.acrobot.co.uk/home.html, "The Acrobot Company Limited—Precision Surgical Systems," printed on Jul. 10, 2002, 1 page.
World Wide Web, http://www.acrobot.co.uk/meetings.html, "The Acrobot Company Limited—Meetings and Publications," printed on Jul. 10, 2002, pp. 1-3.
World Wide Web, http://www.acrobot.co.uk/products.html, "The Acrobot Company Limited—Products," printed on Jul. 10, 2002, pp. 1-6.
World Wide Web, http://www.fcs-cs.com/robotics/content/assistance.htm, "Surgical Assistance," printed on Jun. 12, 2003, 1 page.
World Wide Web, http://www.fcs-cs.com/robotics/content/design.htm, "Virtual Design, Assembly & Maintenance," printed on Jun. 12, 2003, 1 page.
World Wide Web, http://www.fcs-cs.com/robotics/content/endeffectors.htm, "End effectors," printed on Jun. 12, 2003, 1 page.
World Wide Web, http://www.fcs-cs.com/robotics/content/hapticmaster.htm, "HapticMASTER", printed on Jun. 12, 2003, 1 page.
World Wide Web, http://www.fcs-cs.com/robotics/content/reality.htm, "Virtual Reality," printed on Jun. 12, 2003, 1 page.
World Wide Web, http://www.fcs-cs.com/robotics/content/rehabilitation.htm, "Rehabilitation," printed on Jun. 12, 2003, 1 page.
World Wide Web, http://www.fcs-cs.com/robotics/content/research.htm, "Research," printed on Jun. 12, 2003, 1 page.
World Wide Web, http://www.fcs-cs.com/robotics/content/simulation.htm, "Simulation & Training," printed on Jun. 12, 2003, 1 page.
World Wide Web, http://www.fcs-cs.com/robotics/content/software.htm, "Software," printed on Jun. 12, 2003, 1 page.
World Wide Web, http://www.merl.com/projects/surgSim99/, "Knee Arthroscopy Simulation," printed on Jun. 12, 2003, 2 pages.
Written Opinion for PCT/US2006/049216, dated May 8, 2008, 12 pages.
Zilles, et al., "A Constraint-Based God-object Method for Haptic Display", IEEE Proceedings, pp. 146-151, 1995.

\* cited by examiner

SYSTEM AND METHOD FOR VERIFYING CALIBRATION OF A SURGICAL DEVICE

CROSS REFERENCE TO RELATED APPLICATIONS

The present application is a continuation of U.S. patent application Ser. No. 11/750,807, filed May 18, 2007, which claims priority to U.S. Provisional Patent Application Ser. No. 60/801,378, filed on May 19, 2006, each of which is hereby incorporated by reference in its entirety.

BACKGROUND

The invention relates to a surgical system and method and, more particularly, to a surgical system and method for verifying calibration of a surgical device.

Minimally invasive surgery (MIS) is the performance of surgery through incisions that are considerably smaller than incisions used in traditional surgical approaches. For example, in an orthopedic application such as total knee replacement surgery, an MIS incision length may be in a range of about 4 to 6 inches whereas an incision length in traditional total knee surgery is typically in a range of about 6 to 12 inches. As a result of the smaller incision length, MIS procedures are generally less invasive than traditional surgical approaches, which minimizes trauma to soft tissue, reduces post-operative pain, promotes earlier mobilization, shortens hospital stays, and speeds rehabilitation.

One drawback of MIS is that the small incision size reduces a surgeon's ability to view and access the anatomy. For example, in minimally invasive orthopedic joint replacement, limited visibility and limited access to the joint increase the complexity of assessing proper implant position and of reshaping bone. As a result, accurate placement of implants may be more difficult. Conventional techniques for counteracting these problems include, for example, surgical navigation, positioning the leg for optimal joint exposure, and employing specially designed, downsized instrumentation and complex surgical techniques. Such techniques, however, typically require a large amount of specialized instrumentation, a lengthy training process, and a high degree of skill. Moreover, operative results for a single surgeon and among various surgeons are not sufficiently predictable, repeatable, and/or accurate. As a result, implant performance and longevity varies among patients.

In orthopedic applications, one drawback of both MIS and traditional surgical approaches is that healthy as well as diseased bone is removed when the bone is prepared to receive the implant. For example, a total knee replacement can require removal of up to ½ inch of bone on each of three compartments of the knee.

Another drawback of both MIS and traditional orthopedic surgical approaches is that such approaches do not enhance the surgeon's inherent surgical skill in a cooperative manner. For example, some conventional techniques for joint replacement include autonomous robotic systems to aid the surgeon. Such systems, however, typically serve primarily to enhance bone machining by performing autonomous cutting with a high speed burr or by moving a drill guide into place and holding the position of the drill guide while the surgeon inserts cutting tools through the guide. Although such systems enable precise bone resections for improved implant fit and placement, they act autonomously (rather than cooperatively with the surgeon) and thus require the surgeon to cede a degree of control to the robot. Additional drawbacks of autonomous systems include the large size of the robot, poor ergonomics, the need to rigidly clamp the bone during registration and cutting, increased incision length for adequate robot access, and limited acceptance by surgeons and regulatory agencies due to the autonomous nature of the system.

Other conventional robotic systems include robots that cooperatively interact with the surgeon. One drawback of conventional interactive robotic systems is that such systems lack the ability to adapt surgical planning and navigation in real-time to a dynamic intraoperative environment. For example, U.S. patent application Ser. No. 10/470,314 (Pub. No. US 2004/0128026), which is hereby incorporated by reference herein in its entirety, discloses an interactive robotic system programmed with a three-dimensional virtual region of constraint that is registered to a patient. The robotic system includes a three degree of freedom (3-DOF) arm having a handle that incorporates force sensors. The surgeon utilizes the handle to manipulate the arm to move the cutting tool. Moving the arm via the handle is required so that the force sensors can measure the force being applied to the handle by the surgeon. The measured force is then used in controlling motors to assist or resist movement of the cutting tool. For example, during a knee replacement operation, the femur and tibia of the patient are fixed in position relative to the robotic system. As the surgeon applies force to the handle to move the cutting tool, the interactive robotic system may apply an increasing degree of resistance to resist movement of the cutting tool as the cutting tool approaches a boundary of the virtual region of constraint. In this manner, the robotic system guides the surgeon in preparing the bone by maintaining the cutting tool within the virtual region of constraint. As with the above-described autonomous systems, however, the interactive robotic system functions primarily to enhance bone machining. The interactive robotic system also requires the relevant anatomy to be rigidly restrained and the robotic system to be fixed in a gross position and thus lacks real-time adaptability to the intraoperative scene. Moreover, the 3-DOF configuration of the arm and the requirement that the surgeon manipulate the arm using the force handle results in limited flexibility and dexterity, making the robotic system unsuitable for certain MIS applications.

In view of the foregoing, a need exists for a surgical system that can replace direct visualization in minimally invasive surgery, spare healthy bone in orthopedic joint replacement applications, enable intraoperative adaptability and surgical planning, and produce operative results that are sufficiently predictable, repeatable, and/or accurate regardless of surgical skill level. A surgical system need not necessarily meet all or any of these needs to be an advance, though a system meeting these needs would me more desirable.

Furthermore, there is a need for a surgical system and method that can accurately verify the calibration of a surgical device. By verifying the calibration of a surgical device, the surgical system can accurately provide positional information to a user of the surgical device, thus enabling the user to locate the surgical device relative to the anatomy of a patient, despite the size of an incision used for MIS, and to minimize the amount of bone removed during a surgical procedure.

SUMMARY OF THE INVENTION

According to an aspect of the present invention, a method for verifying calibration of a surgical device, comprises the steps of: identifying an interface on an anatomy of a patient;

determining a position of a checkpoint of the interface in a coordinate frame of reference; contacting the interface with a portion of a surgical tool of the surgical device; determining a position of the portion of the surgical tool in the coordinate frame of reference; and determining whether the position of the portion of the surgical tool has an expected correspondence to the position of the checkpoint.

According to a further aspect, the interface can comprise a mechanical interface that includes a portion configured to be affixed to a bone of the patient and an interface portion that is configured to be contacted by the portion of the surgical tool.

According to an aspect of the present invention, a system for verifying calibration of a surgical device, comprises: a portion of a surgical tool of the surgical device configured to contact an interface on an anatomy of a patient; and a computing system programmed to: determine a position of a checkpoint of the interface in a coordinate frame of reference; determine a position of the portion of the surgical tool when contacting the interface, in the coordinate frame of reference; and determine whether the position of the portion of the surgical tool has an expected correspondence to the position of the interface.

BRIEF DESCRIPTION OF THE DRAWINGS

The accompanying drawings, which are incorporated in and constitute a part of this specification, illustrate embodiments of the invention and together with the description serve to explain principles of the invention.

DETAILED DESCRIPTION

Figure 1:
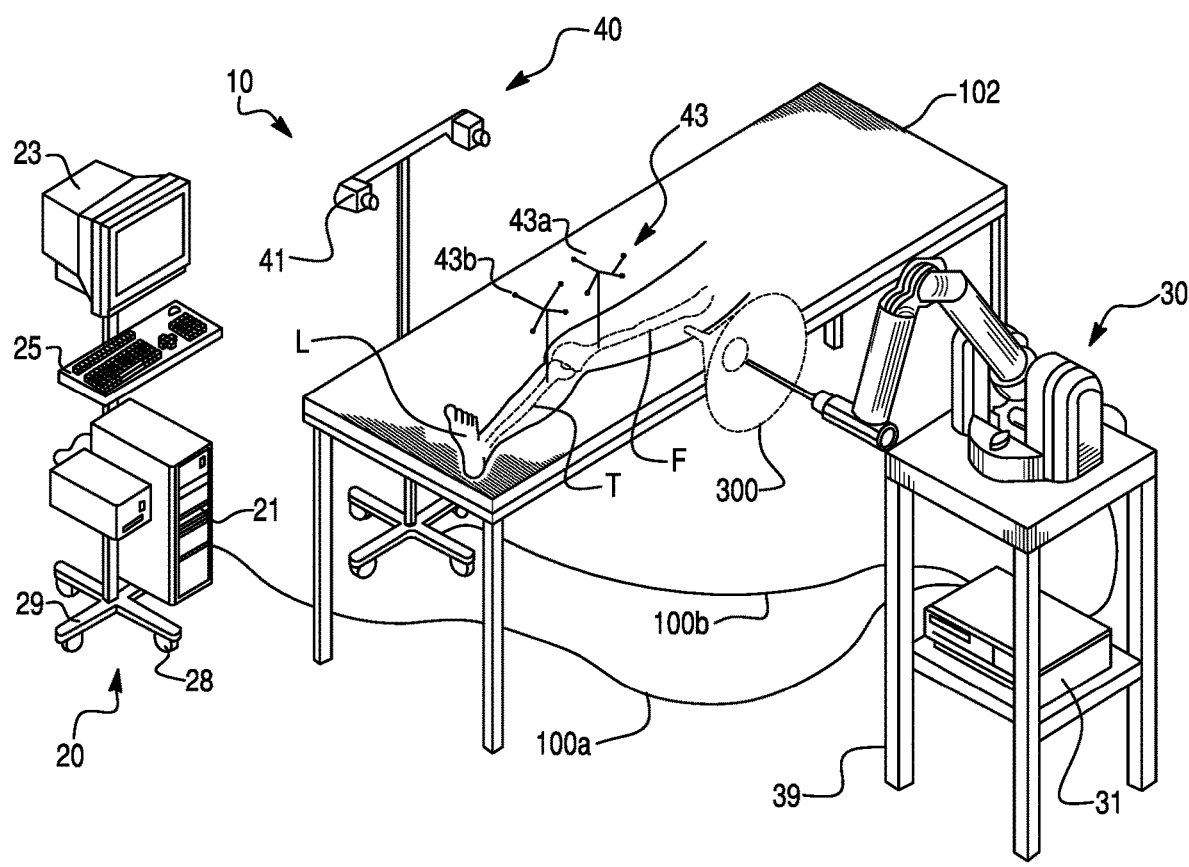
FIG. 1 is a perspective view of an embodiment of a surgical system according to the present invention.

Presently preferred embodiments of the invention are illustrated in the drawings. Although this specification refers primarily to orthopedic procedures involving the knee joint, it should be understood that the subject matter described herein is applicable to other joints in the body, such as, for example, a shoulder, elbow, wrist, spine, hip, or ankle and to any other orthopedic and/or musculoskeletal implant, including implants of conventional materials and more exotic implants, such as orthobiologics, drug delivery implants, and cell delivery implants.

FIG. 1 shows an embodiment of a surgical system 10 according to the present invention. The surgical system 10 includes a computing system 20, a haptic device 30, and a tracking (or localizing) system 40. In operation, the surgical system 10 enables comprehensive, intraoperative surgical planning. The surgical system 10 also provides haptic guidance to a user (e.g., a surgeon) and/or limits the user's manipulation of the haptic device 30 as the user performs a surgical procedure.

The surgical system 10 can be configured and operated as described in U.S. Provisional Patent Application Ser. No. 60/801,378, filed on May 19, 2006, which is hereby incorporated by reference in its entirety, and as described in U.S. patent application Ser. No. 11/357,197, filed Feb. 21, 2006 and published as United States Publication No. 2006/0142657, which is hereby incorporated by reference in its entirety.

The computing system 20 includes hardware and software for operation and control of the surgical system 10. As shown in FIG. 1, the computing system 20 includes a computer 21, a display device 23, and an input device 25. The computing system 20 may also include a cart 29 that can be mounted on wheels 28. As shown in FIG. 1, the computing system 20 can be coupled to the haptic device 30 via an interface 100a. The computing system 20 can be programmed to perform any of the steps and features described herein.

The haptic device 30 is a surgical device configured to be manipulated by a user to move a surgical tool 50 to perform a procedure on a patient. During the procedure, the computing system 20 implements control parameters for controlling the haptic device 30 based, for example, on a relationship between an anatomy of the patient and a position, an orientation, a velocity, and/or an acceleration of a portion of the haptic device 30 (e.g., the surgical tool 50). In one embodiment, the haptic device 30 is controlled to provide a limit on user manipulation of the device (e.g., by limiting the user's ability to physically manipulate the haptic device 30). In another embodiment, the haptic device 30 is controlled to provide haptic guidance (i.e., tactile and/or force feedback) to the user. "Haptic" refers to a sense of touch, and the field of haptics involves research relating to human interactive devices that provide tactile and/or force feedback to an operator. Tactile feedback generally includes tactile sensations such as, for example, vibration, whereas force feedback refers to feedback in the form of force (e.g., resistance to movement) and/or torque (also known as "wrench). Wrench includes, for example, feedback in the form of force, torque, or a combination of force and torque. For example, a haptic guidance system can be configured as described in U.S. patent application Ser. No. 11/646,204, filed Dec. 27, 2006, which is hereby incorporated by reference in its entirety.

Guidance from the haptic device 30 coupled with computer aided surgery (CAS) enables a surgeon to actively and accurately control surgical actions (e.g., bone cutting) and delivery of localized therapies (e.g., in the brain). The computing system 20 can control the haptic device 30 to generate a force, a torque, and/or vibration based on the position of the tool 50 relative to the virtual object, the parameter, and/or the anatomy. Thus, in operation, as a surgeon manipulates the haptic device 30 to move the tool 50, virtual pathways may be used to guide the tool 50 to specific targets, virtual boundaries may be used to define cutting shapes or to prevent the tool 50 from contacting critical tissue, and predefined parameters may be used to limit travel of the tool 50 (e.g., to a predefined depth). The computing system 20 may also be programmed to adjust the control parameters in response to movement of the physical anatomy during the procedure (e.g., by monitoring detected movement of the physical anatomy and then adjusting the virtual object in response to the detected movement). In this manner, the surgical system 10 can supplement or replace direct visualization of the surgical site, enhance the surgeon's natural tactile sense and physical dexterity, and facilitate the targeting, repairing, and replacing of various structures in the body through conventionally sized portals (e.g., 12 inches or greater in length) to portals having a diameter as small as approximately 1 mm.

In orthopedic applications, for example, the haptic device 30 can be applied to the problems of inaccuracy, unpredictability, and non-repeatability in bone (or work piece) preparation by assisting the surgeon with proper sculpting of bone to thereby enable precise, repeatable bone resections while maintaining intimate involvement of the surgeon in the bone preparation process. Moreover, because the haptic device 30 haptically guides the surgeon in the bone cutting operation, the skill level of the surgeon is less critical. As a result, surgeons with varying degrees of skill and experience are able perform accurate, repeatable bone resections. In one embodiment, for example, a surgical tool is coupled to the haptic device 30. The surgeon can operate the tool to sculpt bone by grasping and moving the tool and/or by grasping and manipulating the haptic device 30 to move the tool. As the surgeon performs the cutting operation, the surgical system 10 tracks the location of the tool (with the tracking system 40) and, in most cases, allows the surgeon to freely move the tool in the workspace. When the tool is in proximity to a virtual boundary in registration with the patient, however, the surgical system 10 controls the haptic device 30 to provide haptic guidance that tends to constrain the surgeon from penetrating the virtual boundary with the tool. For example, the virtual boundary may be defined by a haptic object, and the haptic guidance may comprise an output wrench (i.e., force and/or torque) that is mapped to the haptic object and experienced by the surgeon as resistance to further tool movement in the direction of the virtual boundary. A haptic object may have an associated spatial or geometric representation that can be graphically represented on the display device 23. A graphical representation may be selected so as to convey useful information to the user. For example, as shown in FIG. 1, a haptic object 300 configured assist the user in guiding a tool 50 to the surgical site may be represented graphically as a funnel shaped volume. As a virtual tool corresponding to the physical tool 50 moves through and interacts with the haptic object 300, haptic forces are reflected to the user so that the tool 50 is directed to the surgical site. In one embodiment, a haptic object defining a virtual cutting boundary for an implant may be depicted on the display device 23 as a graphical image having a shape that substantially corresponds to a shape of the implant. Thus, a haptic object 208 defining a virtual cutting boundary for a femoral component 72 (shown in FIG. 7A) may have a corresponding graphical representation. Similarly, a haptic object 206 defining a virtual cutting boundary for a tibial component 74 (shown in FIG. 7B) may have a corresponding graphical representation. Thus, the surgeon may feel as if the tool has encountered a physical object, such as a wall. In this manner, the virtual boundary functions as a virtual cutting guide. Thus, the haptic device 30 communicates information to the surgeon regarding the location of the tool relative to the virtual boundary and provides physical guidance in the actual cutting process. The haptic device 30 may also be configured to limit the user's ability to manipulate the surgical tool as described, for example, in U.S. patent application Ser. No. 10/470,314 (Pub. No. US 2004/0128026), which is hereby incorporated by reference herein in its entirety.

The haptic device 30 may include a mechanical or electromechanical device adapted to transmit tactile feedback (e.g., vibration) and/or force feedback (e.g., wrench) to the user. The haptic device 30 may be robotic, non-robotic, or a combination of robotic and non-robotic systems. For example, the haptic device 30 may include a haptic device as described in U.S. Pat. Nos. 7,206,626; 7,206,627; U.S. patent application Ser. No. 10/384,078, filed Mar. 6, 2003, published Feb. 19, 2004; U.S. patent application Ser. No. 10/384,194, filed Mar. 6, 2003, published Feb. 19, 2004; U.S. patent application Ser. No. 10/621,119, filed Jul. 16, 2003, published Jun. 3, 2004; and/or U.S. Provisional Patent Application Ser. No. 60/655,642, filed Feb. 22, 2005. Each of the above-referenced published applications is hereby incorporated by reference herein in its entirety.

Figure 2A:
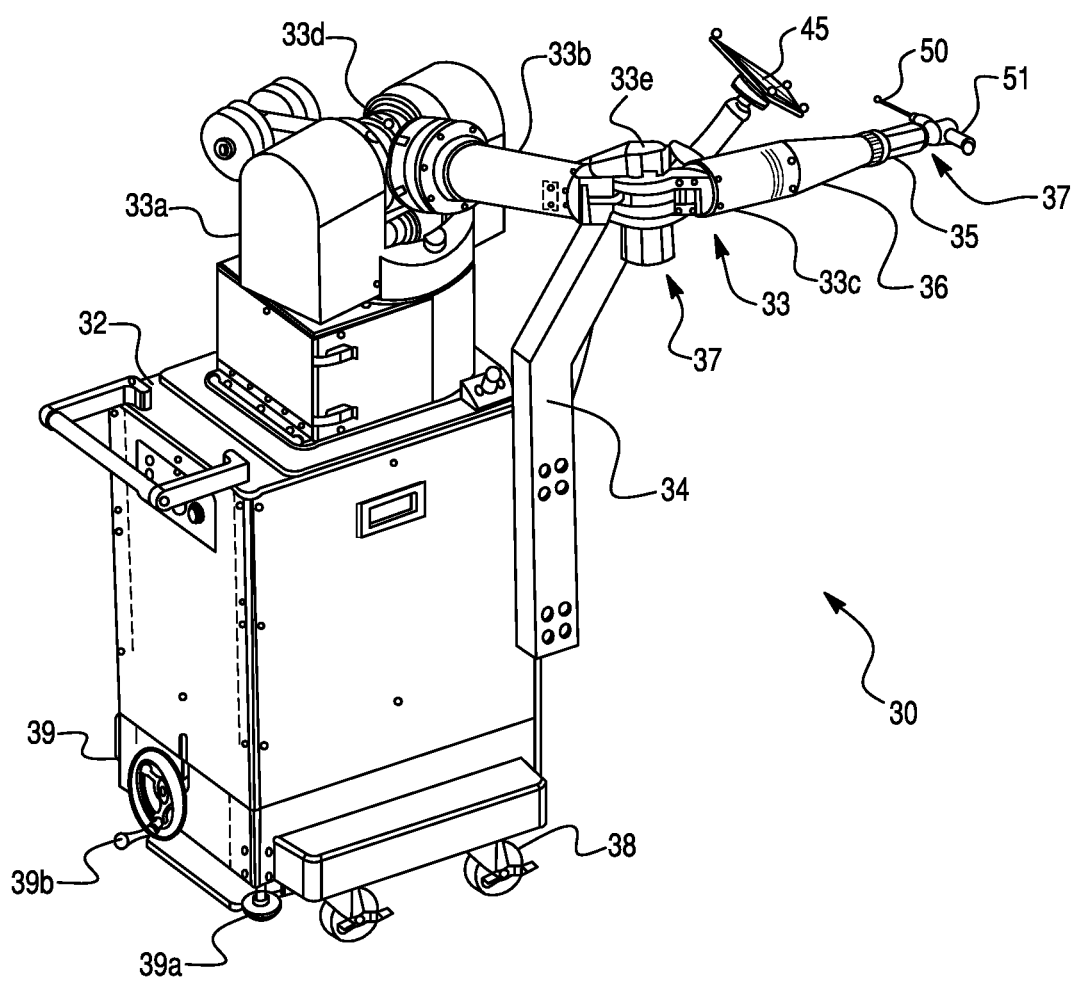
FIG. 2A is a perspective view of an embodiment of a haptic device according to the present invention.

In one embodiment, the haptic device 30 comprises a robot. In such an embodiment, as shown in FIG. 2A, the haptic device 30 can include a base 32, an arm 33, an end effector 35, and a user interface 37. The haptic device 30 may also include a platform 39. Such a platform 39 may include rolling members 38 (e.g., wheels or casters) to enable the platform 39 to be moved. The platform 39 may also include a mechanism for securing the platform 39 in position. For example, the platform 39 may be equipped with wheel locks or brakes for the rolling members 38, a foot pedal locking device, jack stands, and/or any other known mechanism for securing a platform or cart in position. In one embodiment, as shown in FIG. 2A, the platform 39 includes rigid feet 39a that can be actuated between a retracted position (shown in FIG. 2A) and an extended position (not shown) with a mechanism 39b.

Figure 2B:
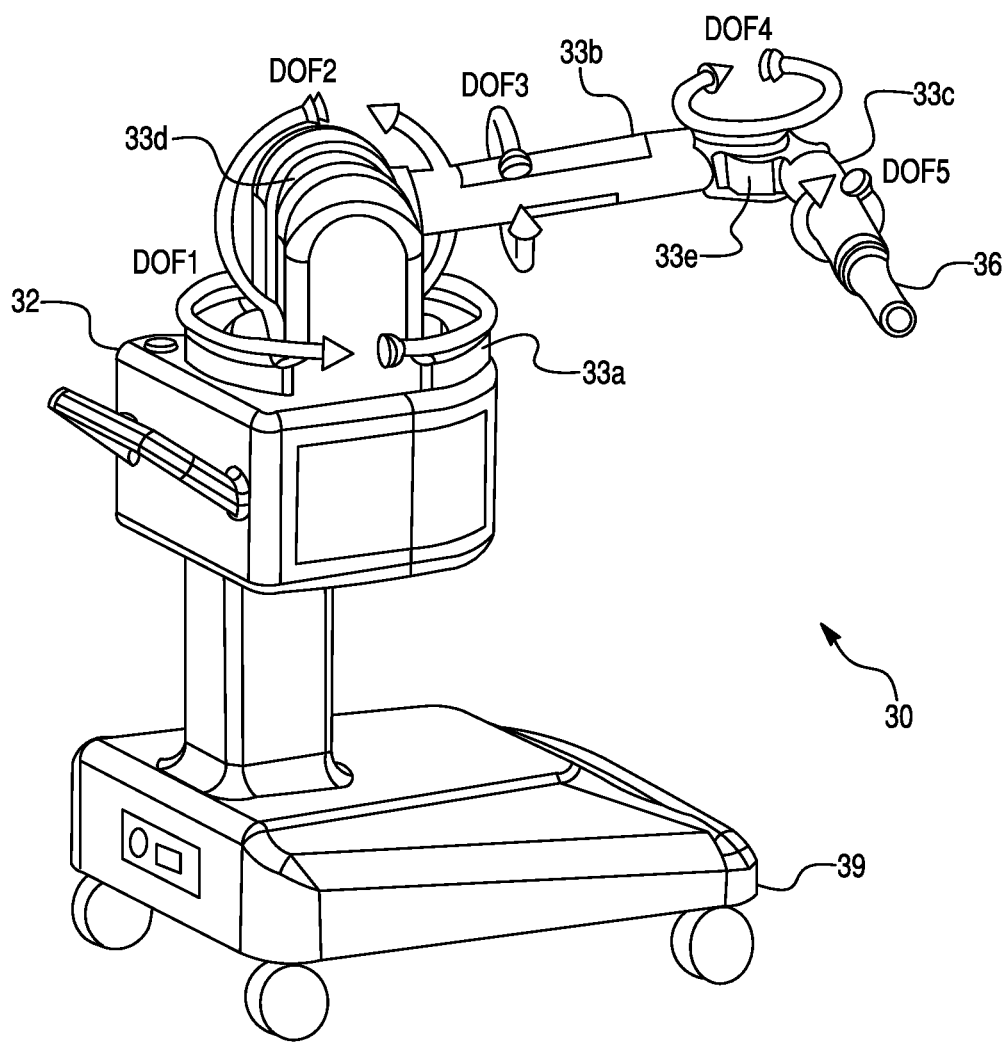
FIG. 2B is a perspective view of an embodiment of a haptic device according to the present invention.

The arm 33 is disposed on the base 32 and is adapted to enable the haptic device 30 to be manipulated by the user. The arm 33 may be any suitable mechanical or electromechanical structure but is preferably an articulated arm having four or more degrees of freedom (or axes of movement), such as, for example, a robotic arm known as the "Whole-Arm Manipulator" or WAM™ currently manufactured by Barrett Technology, Inc. The arm 33 includes a proximal end disposed on the base 32 of the haptic device 30 and a distal end to which a surgical tool 50 is coupled. As described further below, the distal end of the arm 33 may include the end effector 35 and/or a tool holder 51 for the tool 50. In one embodiment, the arm 33 includes a first segment 33a, a second segment 33b, and a third segment 33c as shown in FIG. 2A. The first segment 33a and the second segment 33b are connected at a first joint 33d (e.g., a shoulder joint), and the second segment 33b and the third segment 33c are connected at a second joint 33e (e.g., an elbow joint). As shown in FIG. 2B, the arm 33 may have, for example, a first degree of freedom $DOF_1$, a second degree of freedom $DOF_2$, a third degree of freedom $DOF_3$, and a fourth degree of freedom $DOF_4$. Thus, the segments 33a, 33b, and 33c and the joints 33e and 33d form an articulating mechanical linkage that can be manipulated into various positions or poses. The arm 33 is sized to be appropriate for use in a variety of procedures, such as orthopedic, neurological, and/or trauma procedures, and to be sufficiently compact to enable mobility of the haptic device 30 and efficient positioning of the haptic device 30 in an operating room. For example, the arm 33 may be sized slightly larger than a human arm. In one embodiment, the arm 33 has a reach of approximately 1 m, and a diameter of the segments 33b and 33c is approximately 89 mm. The arm 33 may also be adapted to house and/or route components of the haptic device 30, such as, for example, instrumentation, power lines, motors, transmission components, controllers, actuators, amplifiers, brakes, clutches, power supplies, sensors, and/or computer hardware.

Dexterity of the arm 33 may be enhanced, for example, by adding additional degrees of freedom. For example, the arm 33 may include a wrist 36. As shown in FIG. 2A, the wrist 36 may be disposed on the arm 33 (e.g., at a distal end of the third segment 33c) and includes one or more degrees of freedom to augment the degrees of freedom $DOF_1$, $DOF_2$, $DOF_3$, and $DOF_4$ of the arm 33. For example, as shown in FIG. 2B, the wrist 36 may include a degree of freedom $DOF_5$. In one embodiment, the wrist 36 includes two degrees of freedom, and the degree of freedom $DOF_3$ of the arm 33 is eliminated. The wrist 36 may also be a one degree of freedom or a three degree of freedom WAM™ wrist manufactured by Barrett Technology, Inc.

The end effector 35 may comprise a working end of the haptic device 30 and can be configured to enable the user to perform various activities related to a surgical procedure. For example, in one embodiment, the end effector 35 functions as an adapter or coupling between the arm 33 and the tool 50. By decoupling the tool 50 from the end effector 35 and interchanging one tool 50 for another, the user can utilize the haptic device 30 for different activities, such as registration, bone (or work piece) preparation, measurement/verification, and/or implant installation. In one embodiment, as shown in FIG. 2A, the end effector 35 includes a proximal portion adapted to be connected to the arm 33 and a distal portion that includes the tool 50 and/or a tool holder 51. The proximal portion of the end effector 35 may be electrically and mechanically connected to the arm 33 in any conventional manner. The tool 50 may be, for example, a surgical tool (such as a burr, drill, probe, saw, etc.), medical device, microscope, laser range finder, camera, light, endoscope, ultrasound probe, irrigation device, suction device, radiotherapy device, and/or any other component useful for surgery, surgical planning, and/or surgical navigation. The tool 50 may be a single tool or may include multiple tools.

The tracking (or localizing) system 40 of the surgical system 10 is configured to determine a pose (i.e., position and orientation) of one or more objects during a surgical procedure to detect movement of the object(s). For example, the tracking system 40 may include a detection device that obtains a pose of an object with respect to a coordinate frame of reference (or coordinate system) of the detection device. As the object moves in the coordinate frame of reference, the detection device tracks the pose of the object to detect (or enable the surgical system 10 to determine) movement of the object. As a result, the computing system 20 can adjust the control parameters (e.g., by adjusting a virtual object) in response to movement of the tracked object. Tracked objects may include, for example, tools/instruments, patient anatomy, implants/prosthetic devices, work pieces, and components of the surgical system 10. Using pose data from the tracking system 40, the surgical system 10 is also able to register (or map or associate) coordinates in one space to those in another to achieve spatial alignment or correspondence (e.g., using a coordinate transformation process as is well known). Objects in physical space may be registered to any suitable coordinate system, such as a coordinate system being used by a process running on the computer 21 and/or the computer 31. For example, utilizing pose data from the tracking system 40, the surgical system 10 is able to associate the physical anatomy and the tool 50 (and/or the haptic device 30) with a representation of the anatomy (such as an image displayed on the display device 23). Based on tracked object and registration data, the surgical system 10 may determine, for example, (a) a spatial relationship between the image of the anatomy and the relevant anatomy and (b) a spatial relationship between the relevant anatomy and the tool 50 so that the computing system 20 can superimpose (and continually update) a virtual representation of the tool 50 on the image, where the relationship between the virtual representation and the image is substantially identical to the relationship between the tool 50 and the actual anatomy. Additionally, by tracking not only the tool 50 but also the relevant anatomy, the surgical system 10 can compensate for movement of the relevant anatomy during the surgical procedure (e.g., by adjusting a virtual object in response to the detected movement). As shown in FIG. 1, the tracking system 40 may be coupled to the haptic device 30 via an interface 100b.

The tracking system 40 may be any tracking system that enables the surgical system 10 to continually determine (or track) a pose of the relevant anatomy of the patient and a pose of the tool 50 (and/or the haptic device 30). For example, the tracking system 40 may comprise a non-mechanical tracking system, a mechanical tracking system, or any combination of non-mechanical and mechanical tracking systems suitable for use in a surgical environment.

In one embodiment, as shown in FIG. 1, the tracking system 40 includes a non-mechanical tracking system. In this embodiment, the non-mechanical tracking system is an optical tracking system that comprises a detection device 41 and at least one trackable element (or tracker) configured to be disposed on (or incorporated into) a tracked object and detected by the detection device 41. As shown in FIG. 1, the detection device 41 may include, for example, a stereo camera pair sensitive to infrared radiation and positionable in an operating room where the surgical procedure will be performed. The tracker is configured to be affixed to the tracked object in a secure and stable manner and includes an array of markers (e.g., an array S1 in FIG. 3) having a known geometric relationship to the tracked object. In operation, the detection device 41 detects positions of the markers, and the unique geometry (or firing pattern) and known geometric relationship to the tracked object enable the surgical system 10 to calculate a pose of the tracked object based on the positions of the markers.

A non-mechanical tracking system may include a trackable element (or tracker) for each object the user desires to track. For example, in one embodiment, the non-mechanical tracking system includes an anatomy tracker 43 (to track patient anatomy), a haptic device tracker 45 (to track a global or gross position of the haptic device 30), an end effector tracker 47 (to track a distal end of the haptic device 30), and an instrument tracker 49 (to track an instrument/tool held manually by the user).

Figure 3:
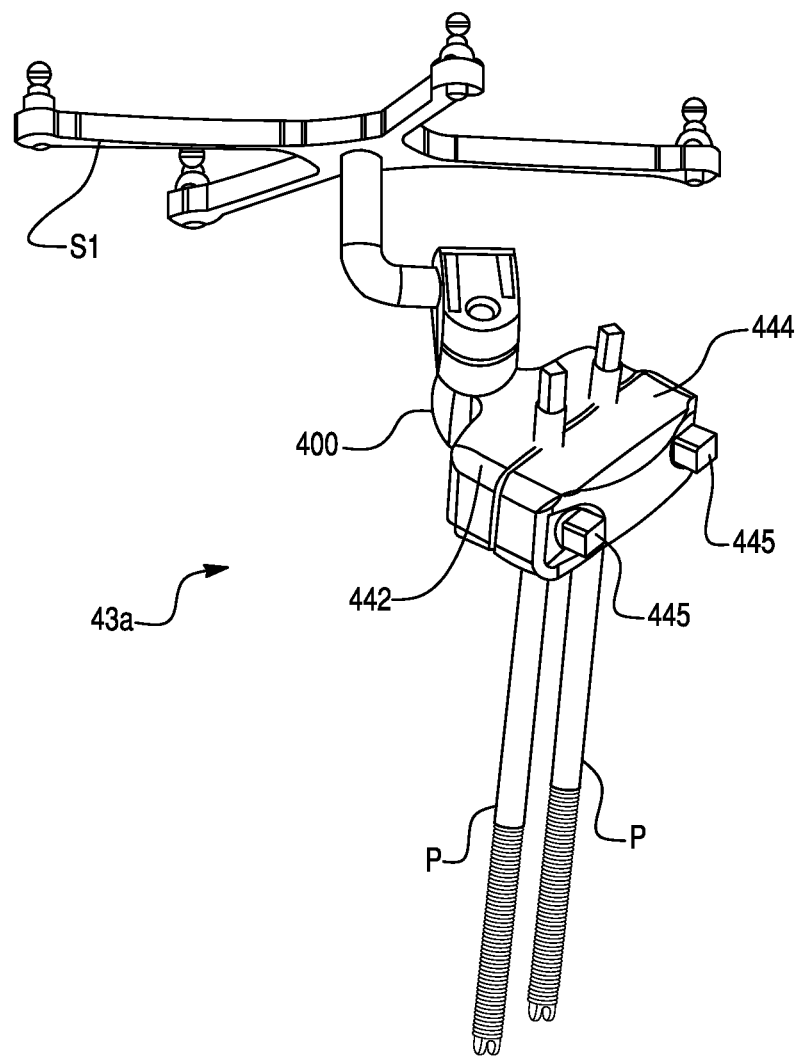
FIG. 3 is a perspective view of an embodiment of an anatomy tracker according to the present invention.

As shown in FIG. 1, the anatomy tracker 43 can be disposed on a relevant portion of a patient's anatomy (such as a bone or work piece) and is adapted to enable the relevant anatomy to be tracked by the detection device 41. The anatomy tracker 43 includes a fixation device for attachment to the anatomy. The fixation device may be, for example, a bone pin, surgical staple, screw, clamp, wearable device, intramedullary rod, or the like. In one embodiment, the anatomy tracker 43 is configured for use during knee replacement surgery to track a femur F and a tibia T of a patient. In this embodiment, as shown in FIG. 1, the anatomy tracker 43 includes a first tracker 43a adapted to be disposed on the femur F and a second tracker 43b adapted to be disposed on the tibia T. As shown in FIG. 3, the first tracker 43a includes a fixation device comprising bone pins P and a unique array S1 of markers (e.g., reflective spheres). The array S1 is affixed to a connection mechanism 400 that is adapted to be removably secured to both of the bone pins P. For example, as shown in FIG. 3, the connection mechanism 400 may include a first portion 442, a second portion 444, and screws 445. To install the first tracker 43a on the femur F, the user screws the bone pins P into the femur F, slides the connection mechanism 400 over the bone pins P, and tightens the screws 445 to draw the first and second portions 442 and 444 together to thereby securely fix the connection mechanism 400 to the bone pins P. Once secured, the connection mechanism 400 imparts additional stability to the bone pins P. The second tracker 43b is identical to the first tracker 43a except the second tracker 43b is installed on the tibia T and has its own unique array of markers. When installed on the patient, the first and second trackers 43a and 43b enable the detection device 41 to track motion of the femur F and the tibia T during knee replacement surgery. As a result, the surgical system 10 is able to compensate for bone motion in real-time during surgery.

As shown in FIG. 2A, the haptic device tracker 45 is disposed on the haptic device 30 and is adapted to enable the surgical system 10 to monitor a global or gross position of the haptic device 30 in physical space. In particular, the haptic device tracker 45 enables the surgical system 10 to determine whether the haptic device 30 has moved relative to other objects in the surgical environment, such as the patient. Such information is important because the tool 50 is attached to the haptic device 30. For example, if the user intentionally repositions or inadvertently bumps the haptic device 30 while cutting the femur F with the tool 50, the tracking system 40 will detect movement of the haptic device tracker 45. In response, the surgical system 10 can make appropriate adjustments to programs running on the computer 21 and/or the computer 31 to compensate for global or gross movement of the haptic device 30 (and the attached tool 50) relative to the femur F. As a result, integrity of the femur preparation process is maintained.

Figure 5:
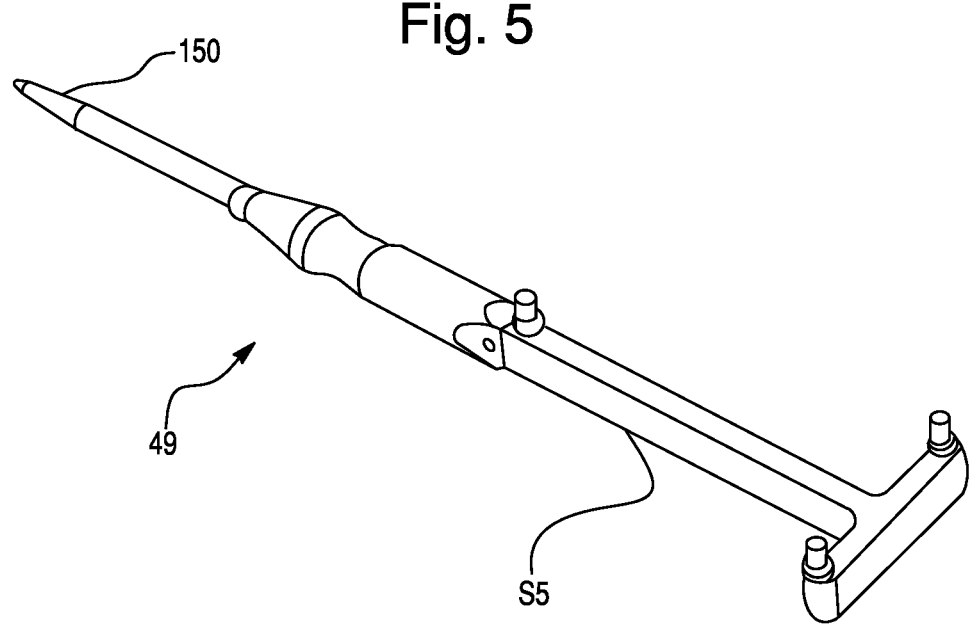
FIG. 5 is a perspective view of an embodiment of an instrument tracker according to the present invention.

The instrument tracker 49 is adapted to be coupled to an instrument 150 that is held manually in the hand of the user (as opposed, for example, to the tool 50 that is attached to the end effector 35). The instrument 150 may be, for example, a probe, such as a registration probe (e.g., a straight or hooked probe). As shown in FIG. 5, the instrument tracker 49 may comprise a unique array S5 of markers (e.g., reflective spheres) formed integrally with the instrument 150 or affixed to the instrument 150 in any known manner, such as with mechanical hardware, adhesive, welding, a threaded connection, a clamping device, a clip, or the like. When the instrument tracker 49 is removably connected to the instrument 150, such as with a clip or a clamping device, the instrument tracker 49 should be calibrated to the instrument 150 to determine a relationship between the instrument tracker 49 and a geometry of the instrument 150. Calibration may be accomplished in any suitable manner, such as with a tool calibrator having a divot or a V-groove (e.g., as described in U.S. Patent Application Pub. No. US 2003/0209096, which is hereby incorporated by reference herein in its entirety). One advantage of using a clip or clamping device to connect the tracker 49 to the instrument 150 is that the clip or clamping device may be adjustable to fit various sizes of instruments. Thus, a single clip or clamping device may be used with multiple instruments. Knowing a geometric relationship between the array S5 and the instrument 150, the surgical system 10 is able to calculate a position of a tip of the instrument 150 in physical space. Thus, the instrument 150 can be used to register an object by touching a tip of the instrument 150 to a relevant portion of the object. For example, the instrument 150 may be used to register a bone of the patient by touching landmarks on the bone or points on a surface of the bone. The instrument 150 may also be used to verify proper alignment of an implant installed in the patient by touching the tip of the instrument 150 to predefined verification features (e.g., divots) located on the implant.

Figure 4:
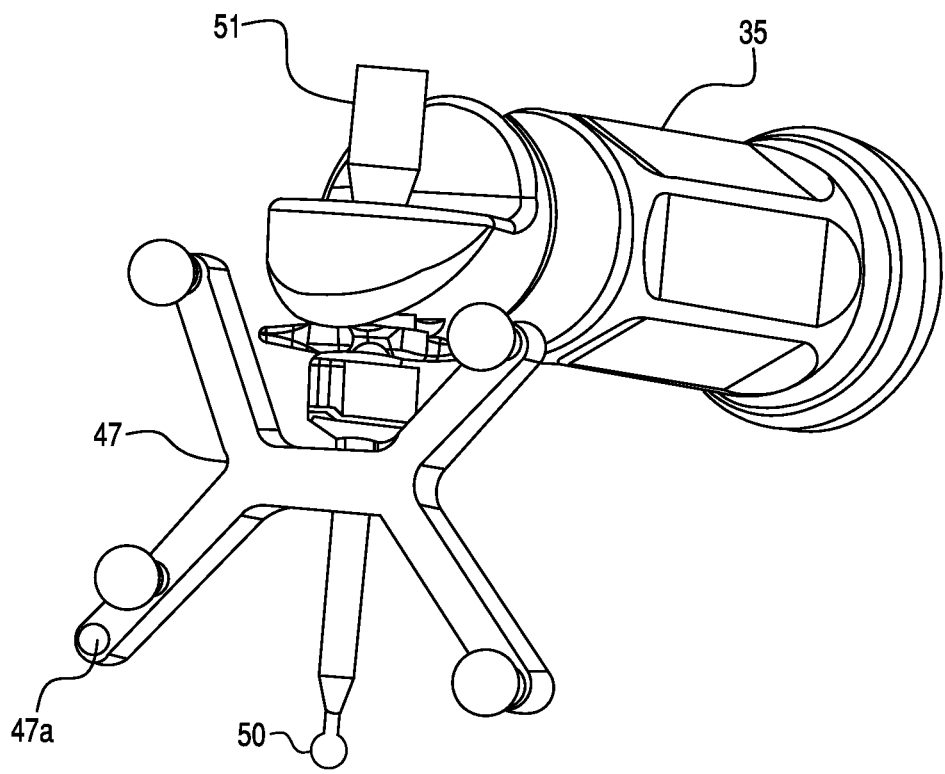
FIG. 4 is a perspective view of the end effector of FIG. 5A attached to a haptic device.
Figure 15:
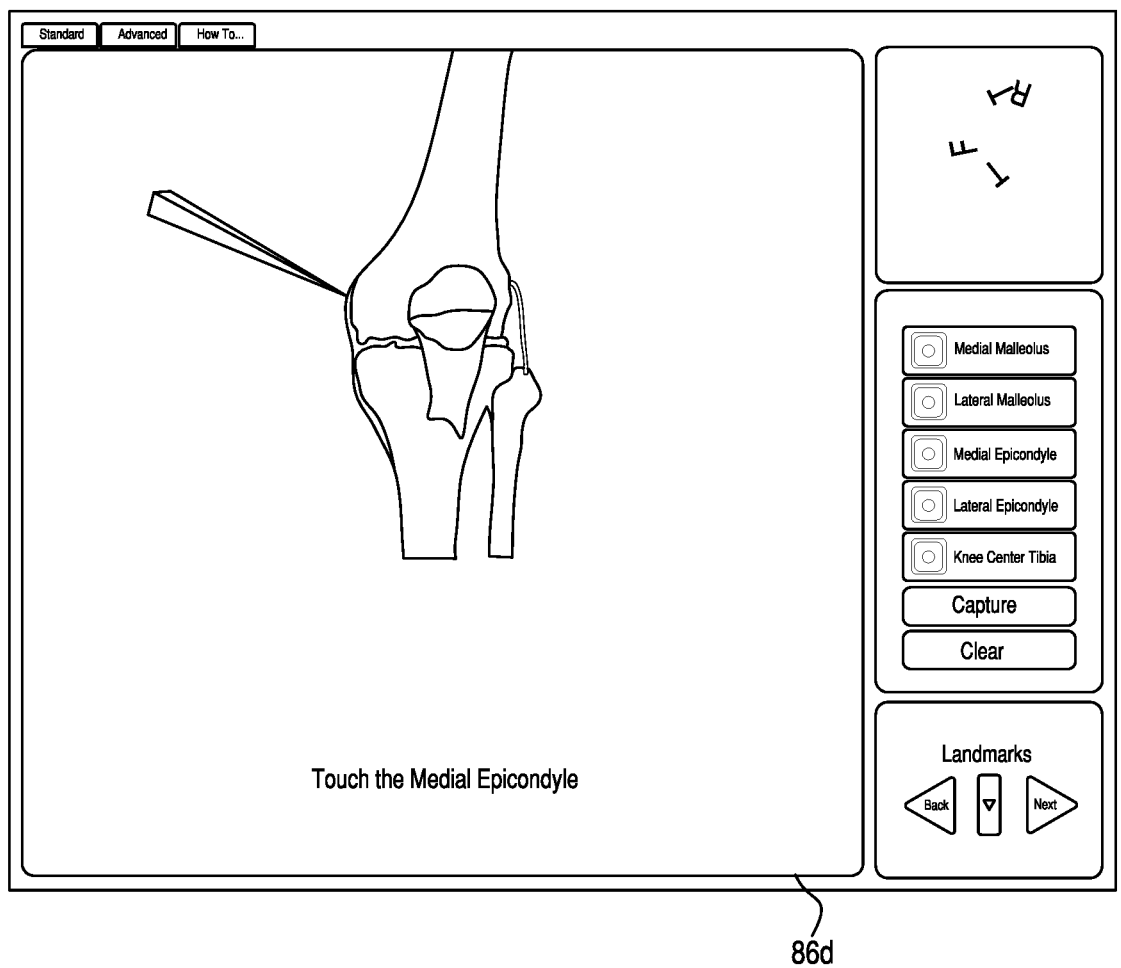
FIG. 15 is a view of an embodiment of a surgical navigation screen showing a registration step according to the present invention.
Figure 16:
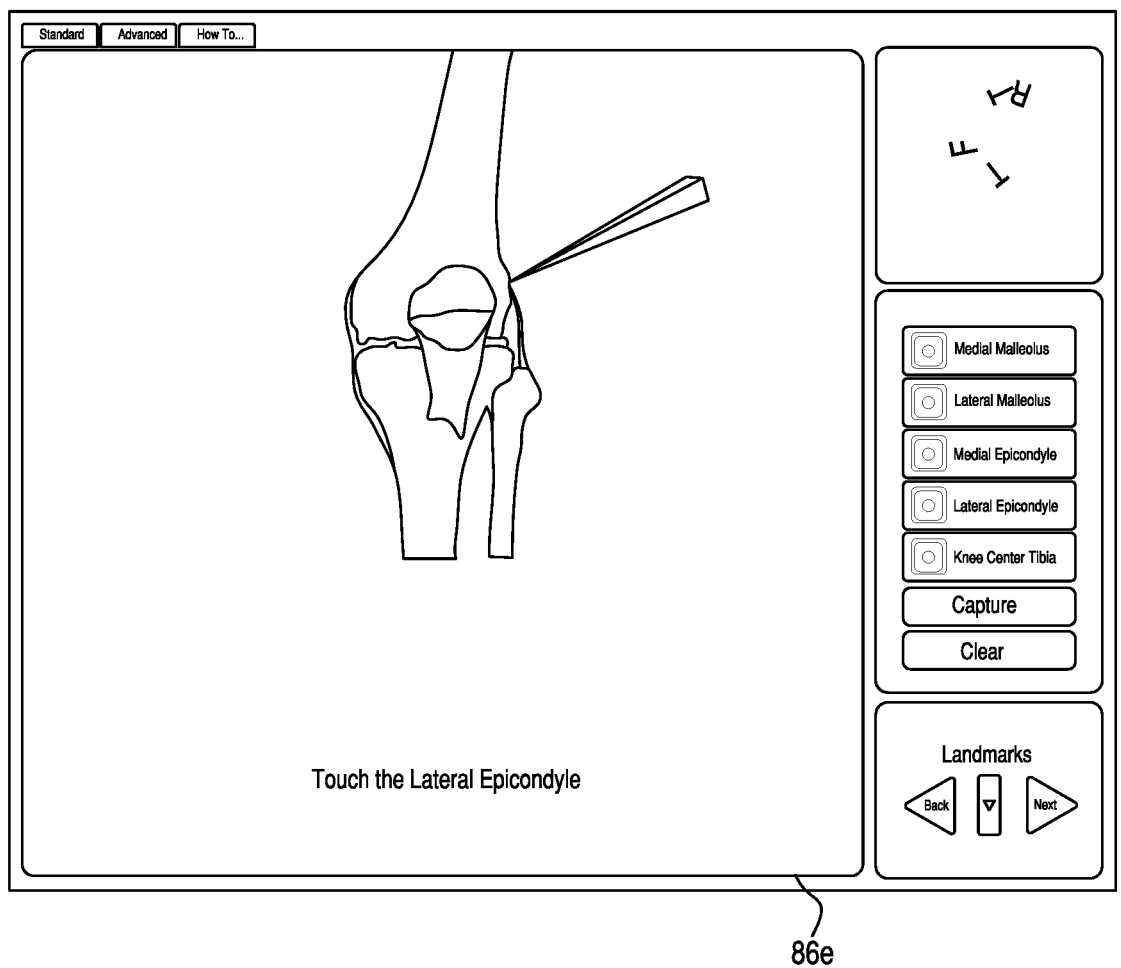
FIG. 16 is a view of an embodiment of a surgical navigation screen showing a registration step according to the present invention.
Figure 17:
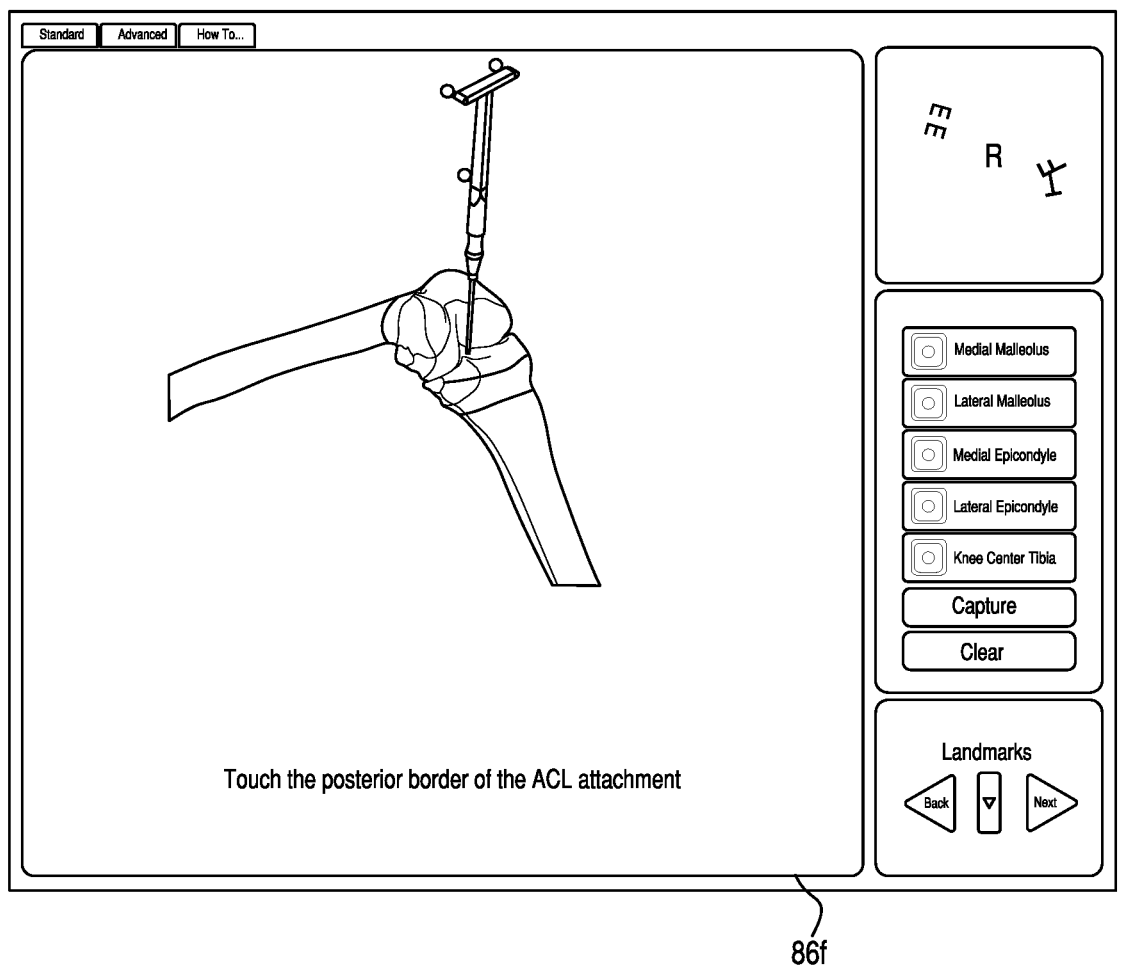
FIG. 17 is a view of an embodiment of a surgical navigation screen showing a registration step according to the present invention.

The instrument tracker 49 may also be configured to verify calibration of the instrument 150. For example, another tracker (e.g., the tracker 43, 45, or 47) may include a divot into which the user can insert the tip of the instrument 150. In one embodiment, as shown in FIG. 4, the end effector tracker 47 includes a divot 47a into which the user can insert the tip of the instrument 150. The detection device 41 can then acquire pose data for the instrument tracker 49 and the end effector tracker 47, and the surgical system 10 can compare an actual geometric relationship between the trackers 47 and 49 to an expected geometric relationship. Deviation between the actual and expected geometric relationships indicates that a physical parameter (e.g., straightness, tip position, etc.) of the instrument 150 is out of calibration. As shown in FIG. 15, during the verification process, the surgical system 10 may display a screen showing a graphical representation of the instrument 150, the instrument tracker 49, and the end effector tracker 47 on the display device 23.

Figure 6:
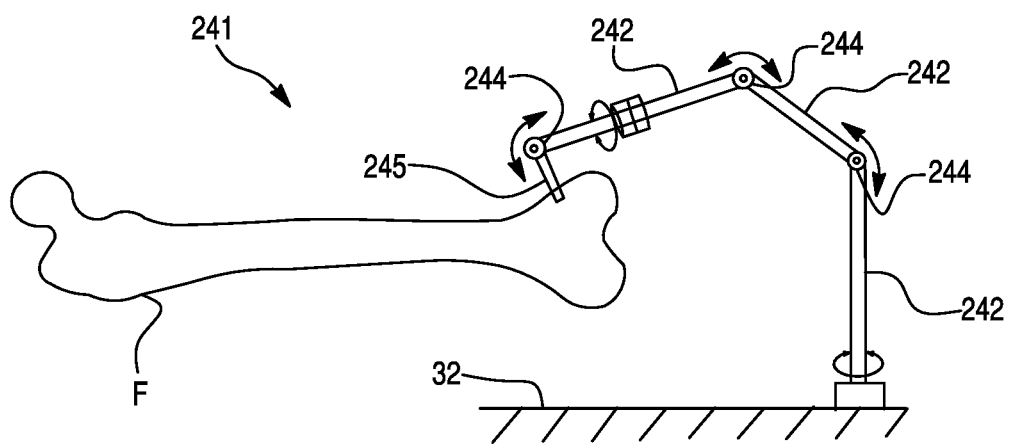
FIG. 6 is a view of an embodiment of a mechanical tracking system according to the present invention.

The tracking system 40 may additionally or alternatively include a mechanical tracking system. In contrast to the non-mechanical tracking system (which includes a detection device 41 that is remote from the trackers 43, 45, 47, and 49), a mechanical tracking system may be configured to include a detection device (e.g., an articulating arm having joint encoders) that is mechanically linked (i.e., physically connected) to the tracked object. The tracking system 40 may include any known mechanical tracking system, such as, for example, a mechanical tracking system as described in U.S. Pat. Nos. 6,033,415 and/or 6,322,567, each of which is hereby incorporated by reference herein in its entirety. In one embodiment, the tracking system 40 includes a mechanical tracking system having a jointed mechanical arm 241 (e.g., an articulated arm having six or more degrees of freedom) adapted to track a bone of the patient. As shown in FIG. 6, the arm 241 has a proximal end affixed to the base 32 of the haptic device 30 and a freely moveable distal end fixed to the femur F of the patient. Alternatively, the proximal end may be affixed to any other suitable location (such as, for example, to a rail of an operating table, a leg holder, etc.) but is preferably connected (e.g., directly or via a bracket) to the base 32 of the haptic device 30 so that the arm 241 moves globally with the haptic device 30. The distal end of the arm 241 includes an fixation device 245 adapted for rigid fixation to the femur F, such as, for example, a bone pin, bone screw, clamp, wearable device, surgical staple, or the like. The arm 241 is configured to have multiple degrees of freedom. For example, in one embodiment, as shown in FIG. 6, the arm 241 includes a plurality of links 242 connected at joints 244. Each joint 244 incorporates one or more position sensors (not shown) to track a pose of the arm 241. The position sensors may include any suitable sensor, such as, for example, the position sensors described above in connection with the arm 33 of the haptic device 30. In operation, as the femur F moves, the distal end of the arm travels with the femur F. The position sensors (and appropriate software) produce measurements of a pose of the distal end of the arm relative to the proximal end of the arm fixed to the haptic device 30. In this manner, motion of the femur F relative to the haptic device 30 is captured. The mechanical tracking system 240 may also include a second arm that is identical to the arm 241 but is rigidly affixed to the tibia T to enable the tracking system 240 to track motion of the tibia T. In this manner, the mechanical tracking system 240 may be used to track the femur F and the tibia T so that the surgical system 10 can detect bone motion in real time during surgery. Using bone motion data in conjunction with appropriate software, the surgical system 10 can compensate for the bone motion in real time during surgery.

When the tracking system 40 includes the mechanical tracking system, the arm 241 may be used to register the patient's anatomy. For example, the user may use the arm 241 to register the tibia T while the second arm (i.e., the arm that is identical to the arm 241 but that is affixed to the tibia T) tracks motion of the tibia T. Registration may be accomplished, for example, by pointing a tip of the distal end of the arm 241 to anatomical landmarks on the tibia T and/or by touching points on (or "painting") a surface of the tibia T with the tip of the distal end of the arm 241. As the user touches landmarks on the tibia T and/or paints a surface of the tibia T, the surgical system 10 acquires data from the position sensors in the arm 241 and determines a pose of the tip of the arm 241. Simultaneously, the second arm provides data regarding motion of the tibia T so that the surgical system 10 can account for bone motion during registration. Based on the bone motion data and knowledge of the position of the tip of the arm 241, the surgical system 10 is able to register the tibia T to the diagnostic images and/or the anatomical model of the patient's anatomy in the computing system 20. In a similar manner, the second arm may be used to register the femur F while the arm 241 (which is affixed to the femur F) tracks motion of the femur F. The patient's anatomy may also be registered, for example, using a non-mechanical tracking system in combination with a tracked probe (e.g., the instrument 150 with the instrument tracker 49) and/or using the haptic device 30 (e.g., as described below in connection with step S8 of FIG. 9).

A fault condition may exist if there is a system problem (e.g., a problem with the hardware or software), if the occlusion detection algorithm detects an occluded condition (e.g., as described below in connection with step S11 of FIG. 9), and/or if the tool 50 is in an undesirable location. In one embodiment, the surgical system 10 is programmed to issue a fault signal and disable the tool 50 if a relationship between the anatomy and a position, an orientation, a velocity, and/or an acceleration of the tool 50 does not correspond to a desired relationship. In one embodiment, the haptic rendering algorithm determines whether the predetermined threshold is exceeded based on the haptic wrench (i.e., force and/or torque) being applied by the haptic device 30 to the user. Another situation that may trigger a fault signal is when rapid motion of the anatomy is detected. Rapid motion may be caused, for example, when the anatomy shifts or someone bumps a tracking element affixed to the anatomy. In one embodiment, the surgical system 10 may have different levels of faults. In one embodiment, the surgical system 10 responds to a fault signal by disabling the tool 50 and placing the haptic device 30 in the free mode (rather than applying the brakes) so that the arm 33 does not pull or apply stress to the anatomy. In this manner, the surgical system 10 avoids damaging the anatomy by preventing the user from operating the tool 50 and/or the arm 33 when an unsafe condition exists.

In one embodiment, a method of controlling the haptic device 30 based on the tool disabling features includes (a) enabling operation of the haptic device 30; (b) manipulating the haptic device 30 to perform a procedure on a patient; (c) determining whether a relationship between the anatomy of the patient and a position, an orientation, a velocity, and/or an acceleration of the tool 50 of the haptic device 30 corresponds to a desired relationship; and (d) issuing a fault signal if the relationship does not correspond to the desired relationship. The method may further include implementing control parameters for controlling the haptic device 30 to provide at least one of haptic guidance to the user and a limit on user manipulation of the surgical device based on the relationship. In one embodiment, in response to the fault signal, the surgical system 10 disables operation of the haptic device 30, locks a portion of the haptic device 30 in position, and/or places the haptic device 10 in a safety mode. In the safety mode, operation of and/or manipulation of the haptic device 30 is impeded.

In one embodiment, a method of compensating for motion of objects during a surgical procedure includes (a) determining a pose of the anatomy; (b) determining a pose of the tool 50; (c) determining at least one of a position, an orientation, a velocity, and an acceleration of the tool 50; (d) associating the pose of the anatomy, the pose of the tool 50, and a relationship between the pose of the anatomy and the at least one of the position, the orientation, the velocity, and the acceleration of the tool 50; and (e) updating the association in response to motion of the anatomy and/or motion of the tool 50. The relationship may be based, for example, on a desired interaction between the anatomy and a position, an orientation, a velocity, and/or an acceleration of the tool 50. In one embodiment, the relationship is defined by a virtual object or parameter positioned relative to the anatomy and representing a desired location of an implant and/or cut surfaces for installing the implant. The step of associating the pose of the anatomy, the pose of the tool 50, and the relationship may be accomplished, for example, using registration processes (e.g., step S8 of FIG. 9), coordinate transformation processes, and implant planning processes (e.g., steps S10 and S13 of FIG. 13). In one embodiment, the step of associating includes (a) defining a first transformation for transforming a coordinate system of the anatomy to a coordinate system of a representation of an anatomy; (b) defining a second transformation for transforming a coordinate system of the tool 50 to a coordinate system of the representation of the anatomy; and (c) associating the relationship with the coordinate system of the representation of the anatomy. To associate the relationship with the coordinate system of the representation of the anatomy, the user may, for example, position a virtual object relative to an image of the anatomy (e.g., implant planning steps S10 and S13 of FIG. 9). To enable the surgical system 10 to compensate for motion of objects during the surgical procedure, the step of updating the association may include updating the first transformation in response to motion of the anatomy and/or updating the second transformation in response to motion of the tool 50.

Figure 20:
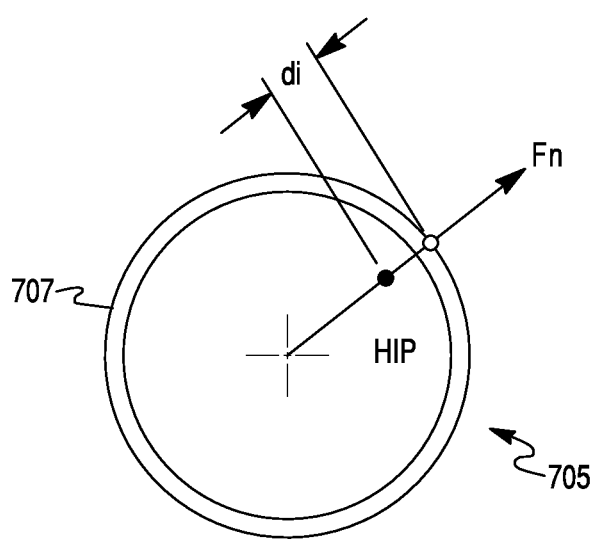
FIG. 20 is a representation of an embodiment of a 3D geometric haptic object according to the present invention.
Figure 21:
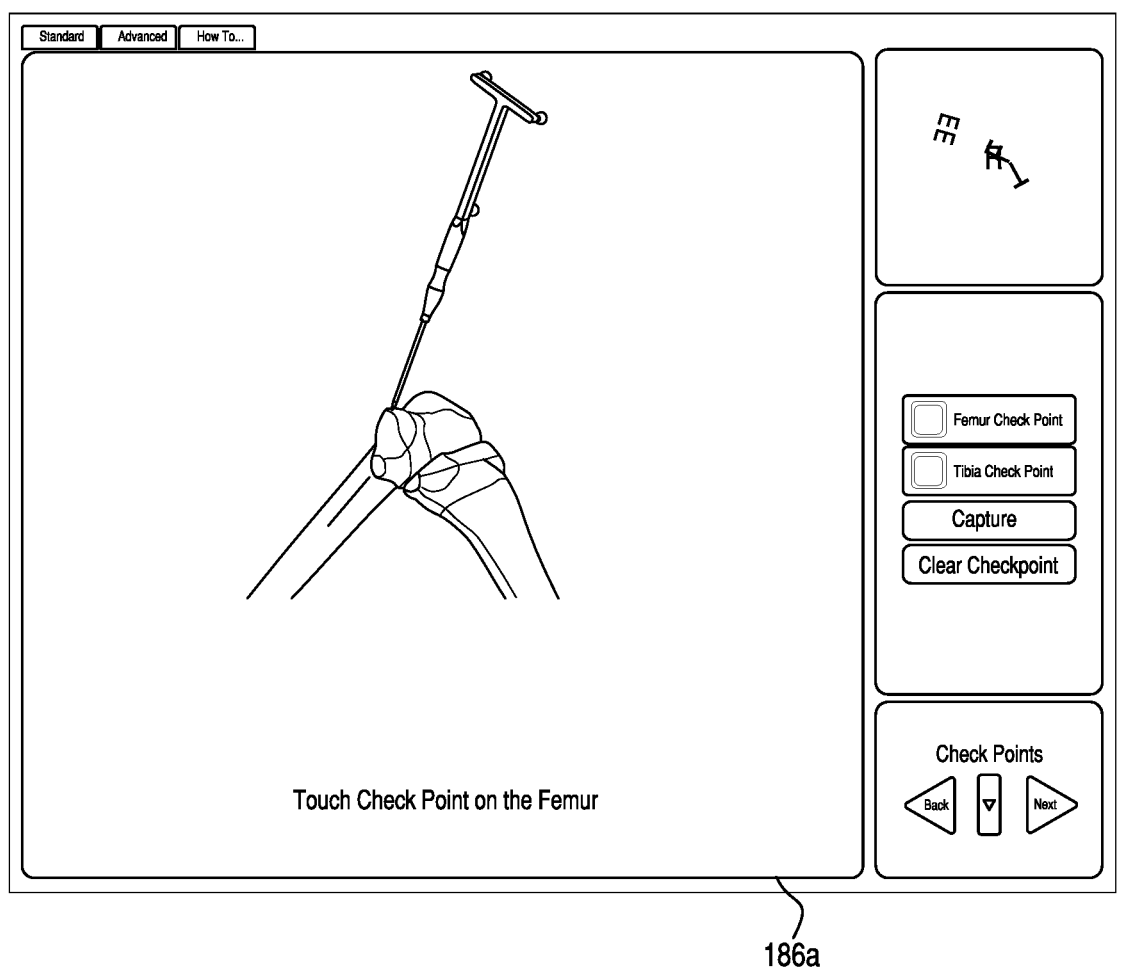
FIG. 21 is a view of an embodiment of a surgical navigation screen showing a checkpoint identification step according to the present invention.
Figure 22:
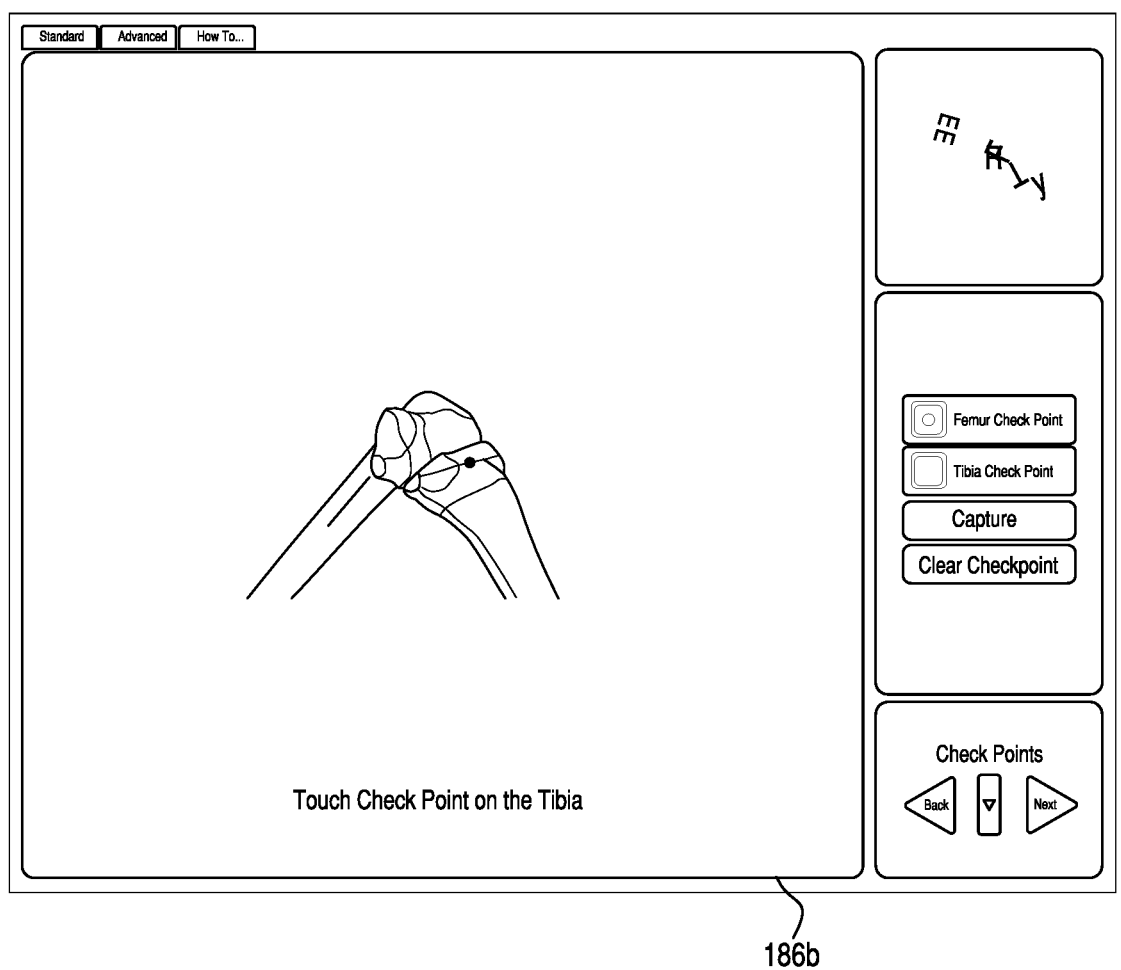
FIG. 22 is a view of an embodiment of a surgical navigation screen showing a checkpoint identification step according to the present invention.

One advantage of including a haptic rendering process in the surgical system 10 is that the haptic rendering process enables interaction between a surgical tool and a virtual environment. The haptic rendering process may include, for example, a haptic rendering process as described in U.S. patent application Ser. No. 11/646,204, filed Dec. 27, 2006, which is hereby incorporated by reference herein in its entirety. For example, the haptic rendering process can create a virtual environment including one or more virtual (or haptic) objects and a virtual representation of the physical tool 50. The physical tool 50 is associated with (e.g., registered to) the virtual environment and/or the virtual representation of the tool 50. Thus, as the user manipulates the physical tool 50, the virtual representation of the tool 50 interacts with virtual objects in the virtual environment. In this manner, the physical tool 50 is able to interact with the virtual environment. Interaction between the virtual objects and the virtual representation of the tool 50 may be based on point, ray (line), multiple point, and/or polygon models. In a preferred embodiment, the surgical system 10 employs point-based haptic interaction where only a virtual point, or haptic interaction point (HIP), interacts with virtual objects in the virtual environment. The HIP corresponds to a physical point on the haptic device 30, such as, for example, a tip of the tool 50. The HIP is coupled to the physical point on the physical haptic device 30 by a virtual spring/damper model. The virtual object with which the HIP interacts may be, for example, a haptic object 705 (shown in FIG. 20) having a surface 707 and a haptic force normal vector $F_n$. A penetration depth $d_i$ is a distance between the HIP and the nearest point on the surface 707. The penetration depth $d_i$ represents the depth of penetration of the HIP into the haptic object 705.

Figure 8:
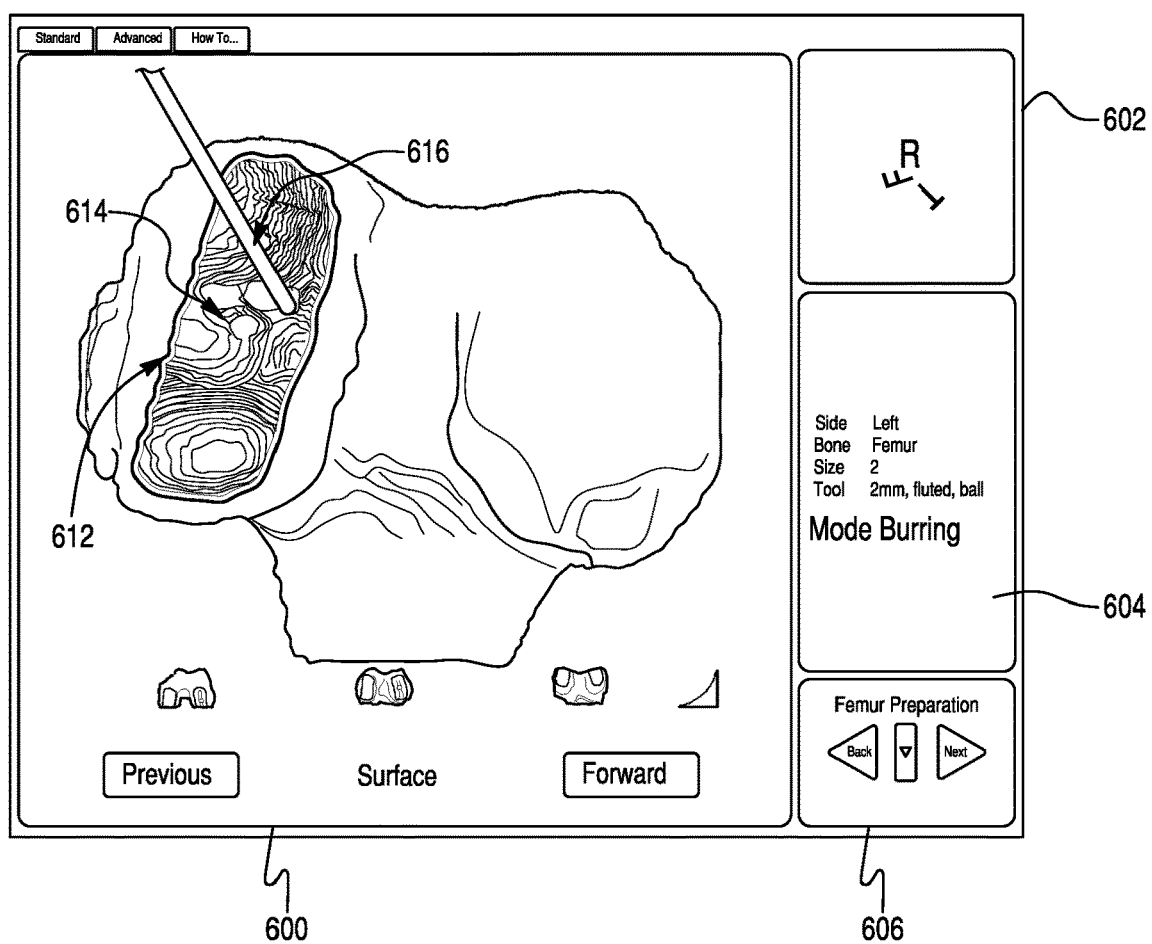
FIG. 8 shows an embodiment of a display of a CAS system according to the present invention.

During a surgical procedure, the computing system 20 guides the user through the procedure. For example, the computing system 20 may be programmed to generate a display configured to guide the user manipulating the haptic device 30 through the procedure. The display may comprise screens shown on the display device 23 that include, for example, predefined pages and/or images corresponding to specific steps of the procedure. The display may also prompt the user to perform one or more tasks. For example, the display may instruct a user to select anatomical landmarks on a representation of the anatomy (discussed below in connection with steps S3 and S4 of FIG. 9). In one embodiment, as shown in FIG. 8, the screen may include a navigation pane 600 for displaying images related to a current step of the procedure; a tracked object pane 602 for showing tracked objects in relation to one another; an information pane 604 for displaying information related to the current step of the procedure, such as, for example, measurement data, error data, status information, selection buttons, and the like; and a pane 606 for advancing to subsequent steps in the procedure and/or returning to previous steps.

Displays or screens associated with the surgical procedure may be configured to communicate visual information to the user regarding the procedure. For example, as shown in FIG. 8, the navigation pane 600 may create and display a representation of the anatomy (such as an image or representation of a bone) and a representation 616 of the surgical tool 50. For a bone preparation process, the surgical system 10 may facilitate the step of preparing the bone to receive an implant by creating a representation 612 of a portion of material to be removed from the bone, superimposing the representation 612 of the portion of material to be removed on the representation of the bone, and updating the representation 612 of the portion of material to be removed with a representation 614 of a portion of material actually removed by the tool 50 as the user manipulates the haptic device 30. To further aid the user, the surgical system 10 can update the representation of the bone and the representation 616 of the tool 50 as the bone and the tool 50 move. In one embodiment, the representation 612 of the portion of material to be removed corresponds to a portion of a virtual object associated with (or registered to) the bone. Thus, the virtual object represents the portion of material to be removed from the anatomy. For example, the virtual object may have a shape substantially corresponding to a shape of a surface of an implant to be fitted to the anatomy (e.g., in a cementless implant application). For cemented implant applications, the virtual object may have a shape that is larger than a shape of the implant to allow room for a cement mantle between the implant and the bone. The above-described bone preparation steps may be performed, for example, on a first bone (e.g., the tibia T) and then repeated for a second bone (e.g., the femur F).

In addition to communicating with the user visually, the computing system 20 may be programmed to emit audible signals (e.g., via the acoustic device). For example, in one embodiment, the computing system 20 may emit sounds (e.g., beeps) indicating that a cutting depth of the tool 50 is too shallow, approximately correct, or too deep. In another embodiment, the surgical system 10 may provide an audible indication of a distance between the tip of the tool 50 and a surface of a haptic object in registration with the patient as described, for example, in U.S. patent application Ser. No. 10/621,119 (Pub. No. US 2004/0106916), which is hereby incorporated by reference herein in its entirety. The computing system 20 may also be programmed to control the haptic device 30 to provide tactile feedback to the user, such as, for example, a vibration indicating that the tool 50 has reached or exceeded the desired cutting depth. The software of the computing system 20 may also include programs or processes that automatically prompt a user to perform certain tasks, such as, for example, segmenting an image of a diagnostic image data set, selecting points on the patient's anatomy to define a mechanical axis, touching (or "painting") points on a surface of the bone with a registration probe, entering data (e.g., implant size, burr size, etc.), and the like.

Figure 9:
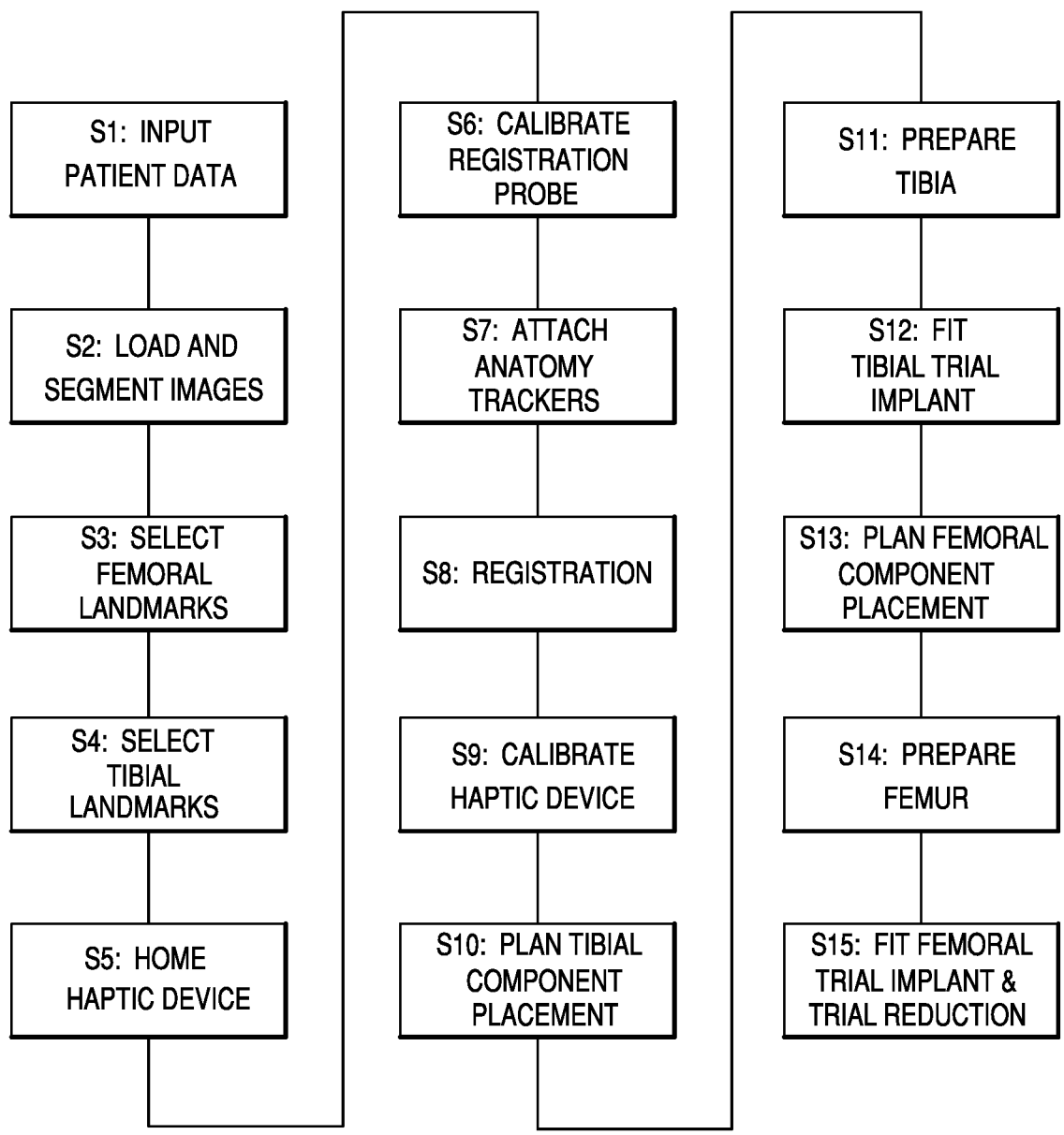
FIG. 9 is a block diagram of an embodiment of a process for a unicondylar knee replacement according to the present invention.

FIG. 9 illustrates an embodiment of a process for using the surgical system 10 for surgical planning and navigation of a unicondylar knee replacement. The process of FIG. 9 is intended as an exemplary illustration only. In other embodiments, the order of the steps of the process may be rearranged in any manner suitable for a particular surgical application. Additionally, other embodiments may include all, some, or only portions of the steps illustrated in FIG. 9 and may combine any of the steps of FIG. 9 with existing and/or later developed surgical approaches. The unicondylar knee replacement procedure detailed in the process of FIG. 9 is for a medial side of the knee. The same process may be used, however, for a lateral side of the knee. Moreover, the illustrated unicondylar procedure is exemplary only. The surgical system 10 may also be used to perform a total knee replacement procedure or other joint replacement procedure involving installation of an implant. The implant may include any implant or prosthetic device, such as, for example, a total knee implant; a unicondylar knee implant; a modular knee implant; implants for other joints including hip, shoulder, elbow, wrist, ankle, and spine; and/or any other orthopedic and/or musculoskeletal implant, including implants of conventional materials and more exotic implants, such as orthobiologics, drug delivery implants, and cell delivery implants. In one embodiment, the implant is a modular knee implant as described in U.S. patent application Ser. No. 11/312,741, filed Dec. 30, 2005, published Aug. 24, 2006, or U.S. patent application Ser. No. 11/684,514, filed Mar. 9, 2007, each of which is hereby incorporated by reference herein in its entirety.

Figure 7A:
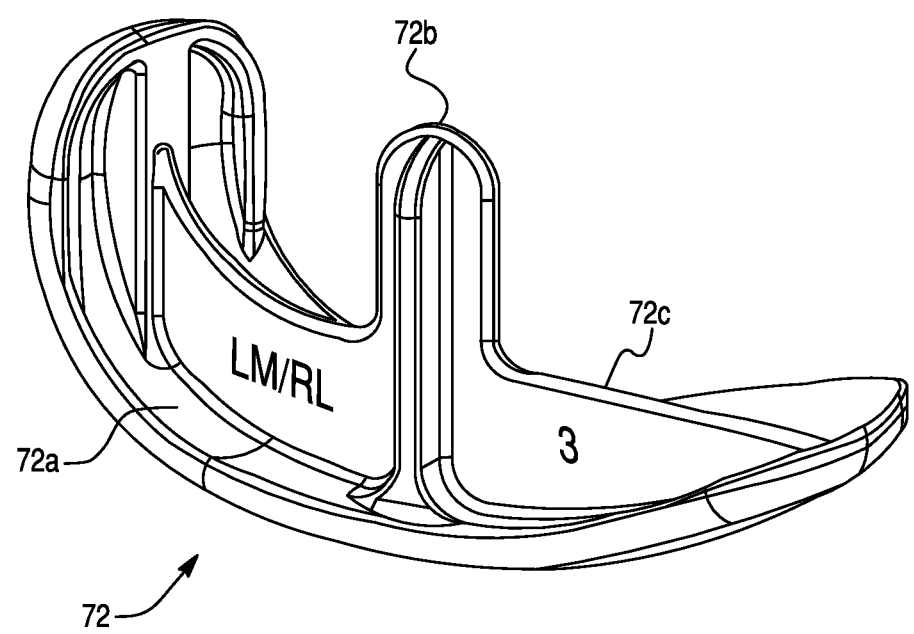
FIG. 7A is a perspective view of an embodiment of a femoral component according to the present invention.
Figure 7B:
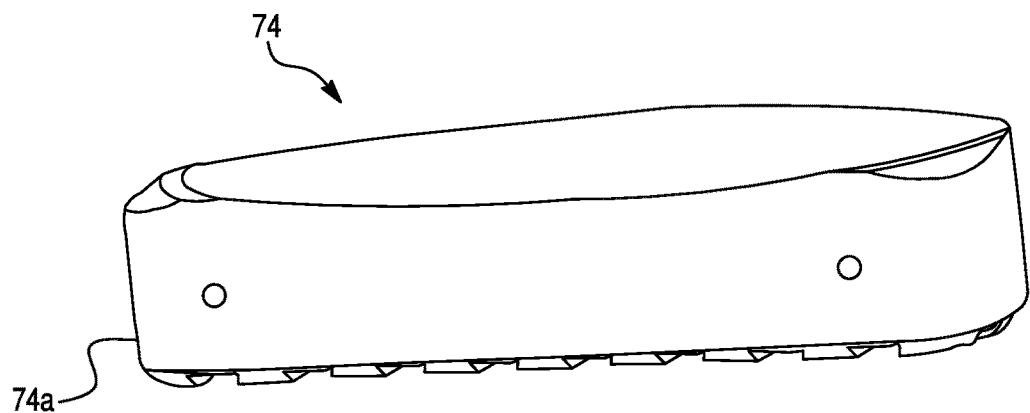
FIG. 7B is a perspective view of an embodiment of a tibial component according to the present invention.

In the embodiment of FIG. 9, steps S1 to S4 are performed preoperatively, and steps S5 to S14 are performed intraoperatively. In step S1, patient information or data may be input to the surgical system 10. In step S2, a preoperative diagnostic image (e.g., a CT data file) is loaded into the surgical system 10 and segmented. In step S3, femoral landmarks are selected. In step S4, tibial landmarks are selected. In step S5, a homing process is performed on the haptic device 30 to initialize position sensors in the arm 33 of the haptic device 30. In step S6, calibration of a registration probe is verified. In step S7, the anatomy trackers 43*a* and 43*b* are attached to the patient. In step S8, patient anatomy is registered. In step S9, the haptic device 30 is calibrated. In step S10, an initial placement of a tibial implant (e.g., a tibial component 74 as shown in FIG. 7B) is planned. A depth of the initial placement may be guided by points that are selected on a surface of the tibial plateau cartilage and transferred to a planning screen on the display device 23 using the registration computed in step S8. In step S11, the tibia T is prepared or sculpted. In step S12, a tibial trial implant is fitted to the prepared surface of the tibia T. In step S13, an initial placement of a femoral implant (e.g., a femoral component 72 as shown in FIG. 7A) is planned, for example, using points related to a position of the tibial trial implant at various flexions of the leg. In step S14, the femur F is prepared or sculpted. In step S15, a femoral trail implant is fitted to the prepared surface of the femur F. A trial reduction process is performed in which the user assesses the fit of the femoral and tibial trial implants and makes any desired adjustments (e.g., repeating implant planning and/or bone sculpting) prior to installing the femoral component 72 and the tibial component 74.

Figure 13:
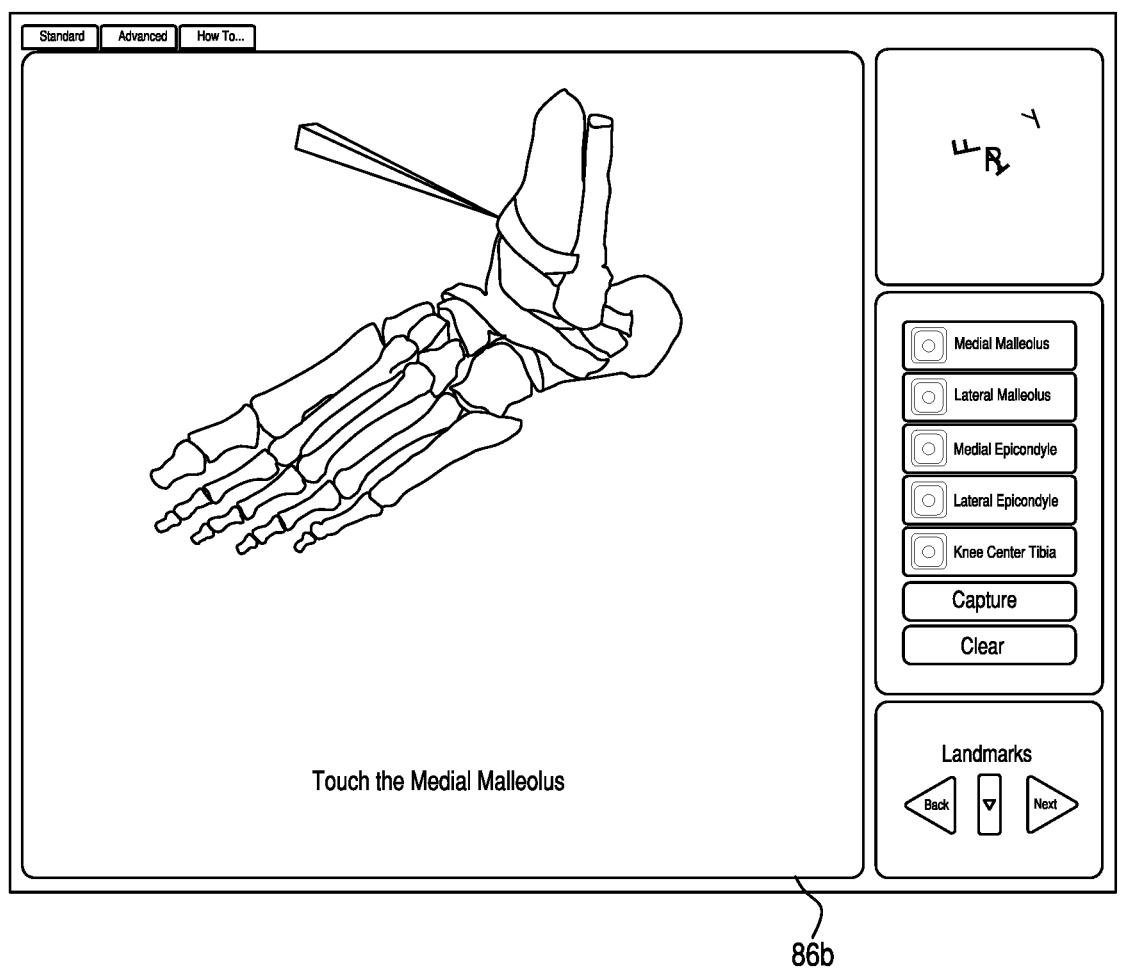
FIG. 13 is a view of an embodiment of a surgical navigation screen showing a registration step according to the present invention.
Figure 14:
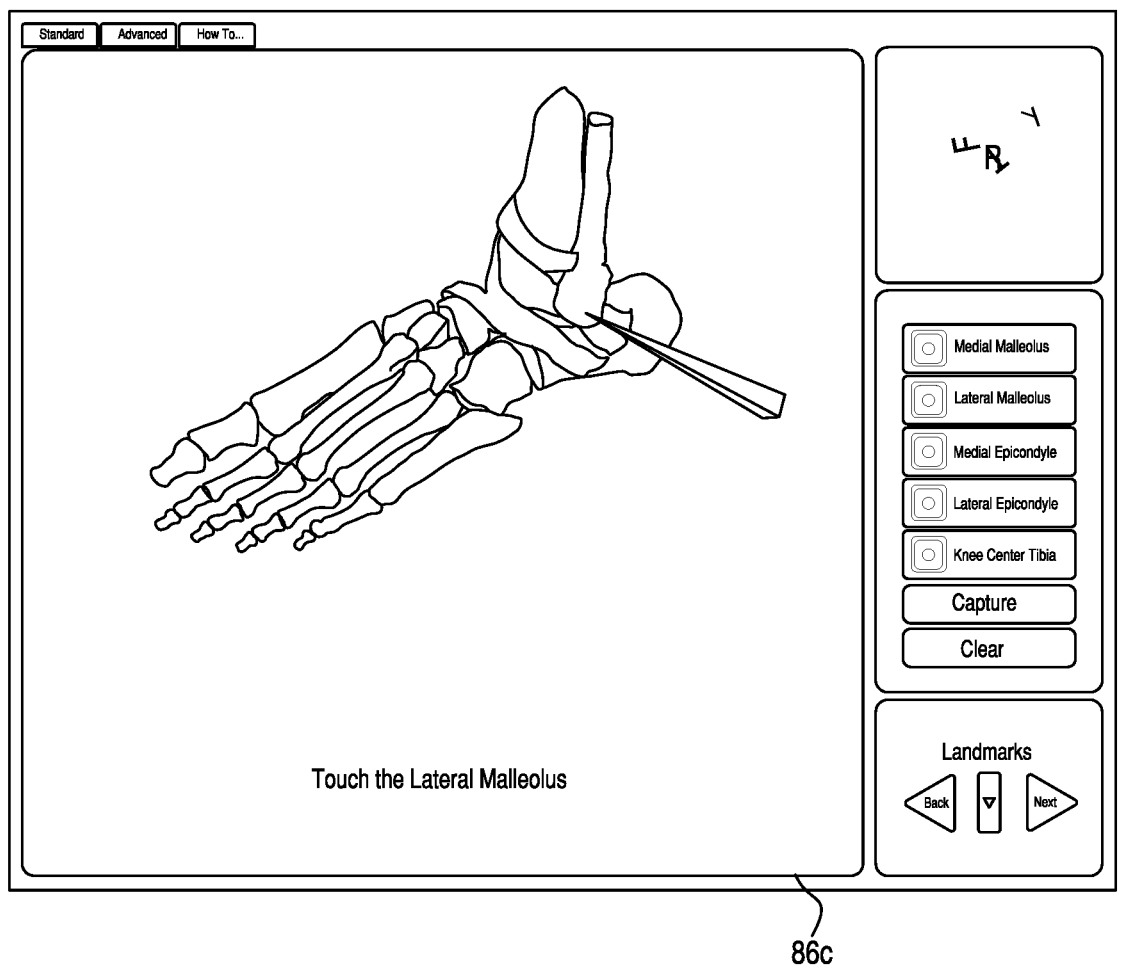
FIG. 14 is a view of an embodiment of a surgical navigation screen showing a registration step according to the present invention.

Regarding the steps of FIG. 13 in further detail, in steps S3 and S4 the user designates landmarks on the representation of the first bone and the representation of the second bone. For example, in step S3, the user may designate femoral landmarks on an image of the femur F. The femoral landmarks are used by the surgical system 10 to associate (or register) the patient's physical anatomy with the representation of the anatomy (e.g., diagnostic images, models generated from segmentation, anatomical models, etc.). In one embodiment, the user may select the femoral landmarks on a displayed image using a mouse or touch screen. In another embodiment, the computer may be programmed to determine the location of the femoral landmarks in the images, for example, using algorithms designed to locate distinguishing features in the diagnostic images.

Similarly, in step S4, the user may designate tibial landmarks on an image of the tibia T. The tibial landmarks are used by the surgical system 10 to associate (or register) the patient's physical anatomy with the representation of the anatomy (e.g., diagnostic images, models generated from segmentation, anatomical models, etc.). As shown in FIGS. 20 to 23, the surgical system 10 generates screens 83*a*, 83*b*, 83*c*, and 83*d*, respectively, to guide the user in specifying the tibial landmarks. For example, the surgical system 10 may direct the user to specify a medial malleolus, a lateral malleolus, a rotational landmark, and a knee center. In one embodiment, the user may select the tibial landmarks on a displayed image using a mouse or touch screen. In another embodiment, the computer may be programmed to determine the tibial landmarks, for example, using algorithms designed to locate distinguishing features in the diagnostic images.

In step S5, a homing process initializes the position sensors (e.g., encoders) of the haptic device 30 to determine an initial pose of the arm 33. Homing may be accomplished, for example, by manipulating the arm 33 so that each joint encoder is rotated until an index marker on the encoder is read. The index marker is an absolute reference on the encoder that correlates to a known absolute position of a joint. Thus, once the index marker is read, the control system of the haptic device 30 knows that the joint is in an absolute position. As the arm 33 continues to move, subsequent positions of the joint can be calculated based on the absolute position and subsequent displacement of the encoder. The surgical system 10 may guide the user through the homing process by providing instructions regarding the positions in which the user should place the arm 33. The instructions may include, for example, images displayed on the display device 23 showing the positions into which the arm 33 should be moved.

Figure 10:
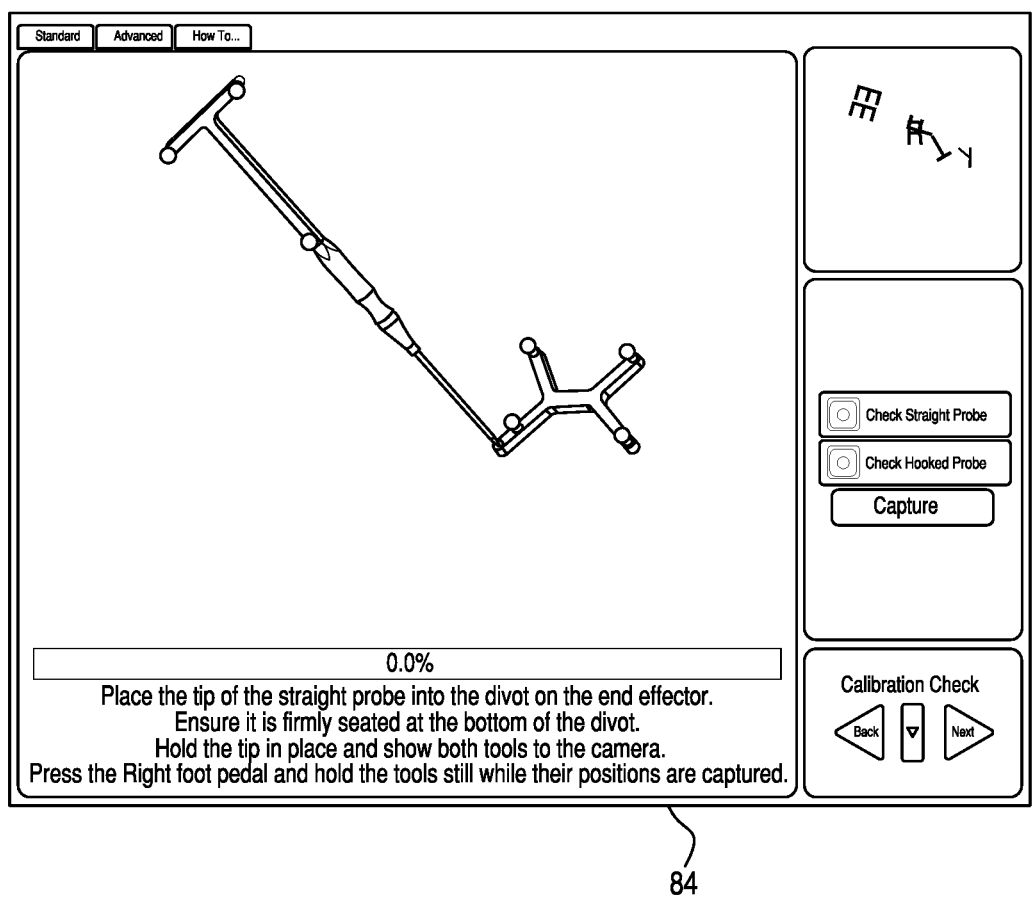
FIG. 10 is a view of an embodiment of a surgical navigation screen showing a probe calibration verification step according to the present invention.

In step S6, an instrument (e.g., a registration probe such as the instrument 150) is checked to verify that the instrument is calibrated. For example, step S6 may be used to verify that a registration probe has a proper physical configuration. As discussed above in connection with the instrument tracker 49, calibration of a probe that includes the instrument tracker 49 may be accomplished by inserting a tip of the probe into the divot 47a of the end effector tracker 47, holding the tip in place, and detecting the instrument tracker 49 and the end effector tracker 47 with the detection device 41. The detection device 41 acquires pose data, and the surgical system 10 compares an actual geometric relationship between the trackers 49 and 47 to an expected geometric relationship between the trackers 49 and 47. Deviation between the actual and expected geometric relationships indicates one or more physical parameters of the probe is out of calibration. As shown in FIG. 10, during the verification process, the surgical system 10 may display a screen 84 showing a graphical representation of the probe, the instrument tracker 49, and the end effector tracker 47 on the display device 23.

Figure 11:
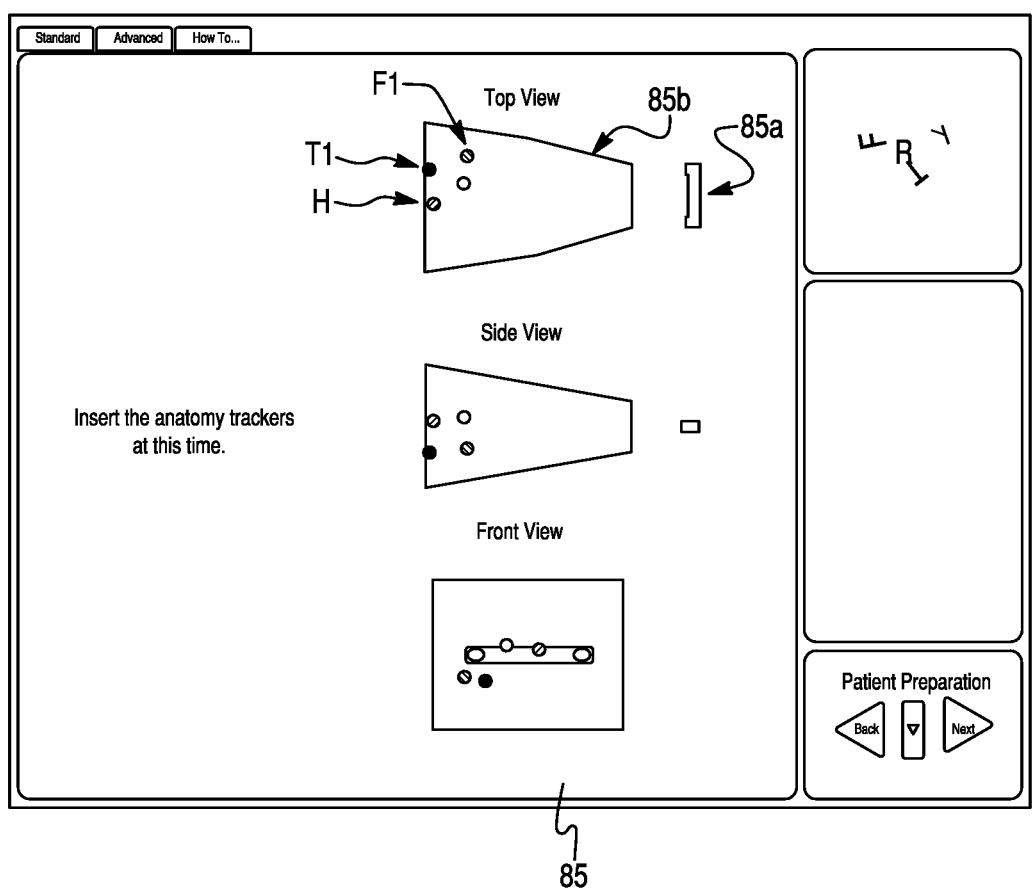
FIG. 11 is a view of an embodiment of a surgical navigation screen showing an anatomy tracker installation step according to the present invention.

In step S7, the surgical system 10 prompts the user to attach the anatomy trackers 43a and 43b to the patient. As shown in FIG. 11, the surgical system 10 may also generate a screen 85 to enable the user to optimize positioning of tracked objects with respect to the detection device 41. For example, the screen 85 may include a representation 85a of the detection device 41 and a representation 85b of a field of view of the detection device 41. The screen may also display a representation F1 of the anatomy tracker 43a, a representation T1 of the anatomy tracker 43b, a representation H of the haptic device tracker 45, and/or a representation of any other trackable element in relation to the field of view 85a of the detection device 41. In one embodiment, each of the representations F1, T1, and H is displayed in a different color to enable the user to distinguish between each of the tracked objects. In another embodiment, the representations F1, T1, and H1 may change to a different color when the tracked object is near a boundary of the field of view of the detection device 41. In this manner, the user may determine whether tracked objects are sufficiently positioned within the field of view of the detection device 41.

In one embodiment, once the anatomy trackers 43a and 43b are attached, a range of motion (ROM) of the knee joint is captured (e.g., by moving the knee joint through the ROM while tracking the anatomy trackers 43a and 43b with the tracking system 40). The captured ROM data may be used to assess relative placement of the femoral and tibial implants. In this way, comprehensive placement planning for both implants can be performed before cutting any bone. The ROM data may also be used (e.g., during the implant planning steps S10 and S13) to display relative positions of the femoral and tibial implants at extension, flexion, and various angles between extension and flexion on the display device 23.

Figure 12:
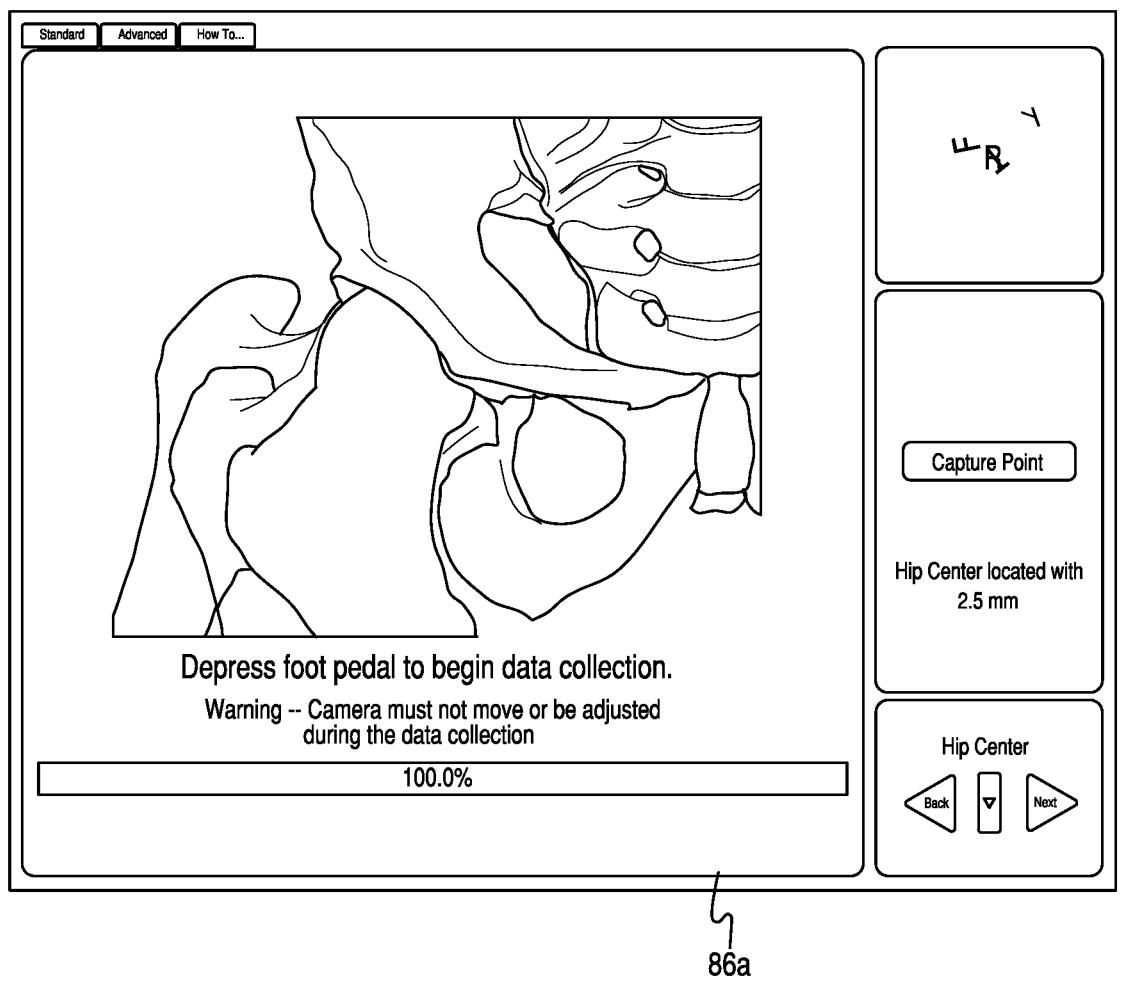
FIG. 12 is a view of an embodiment of a surgical navigation screen showing a registration step according to the present invention.
Figure 18:
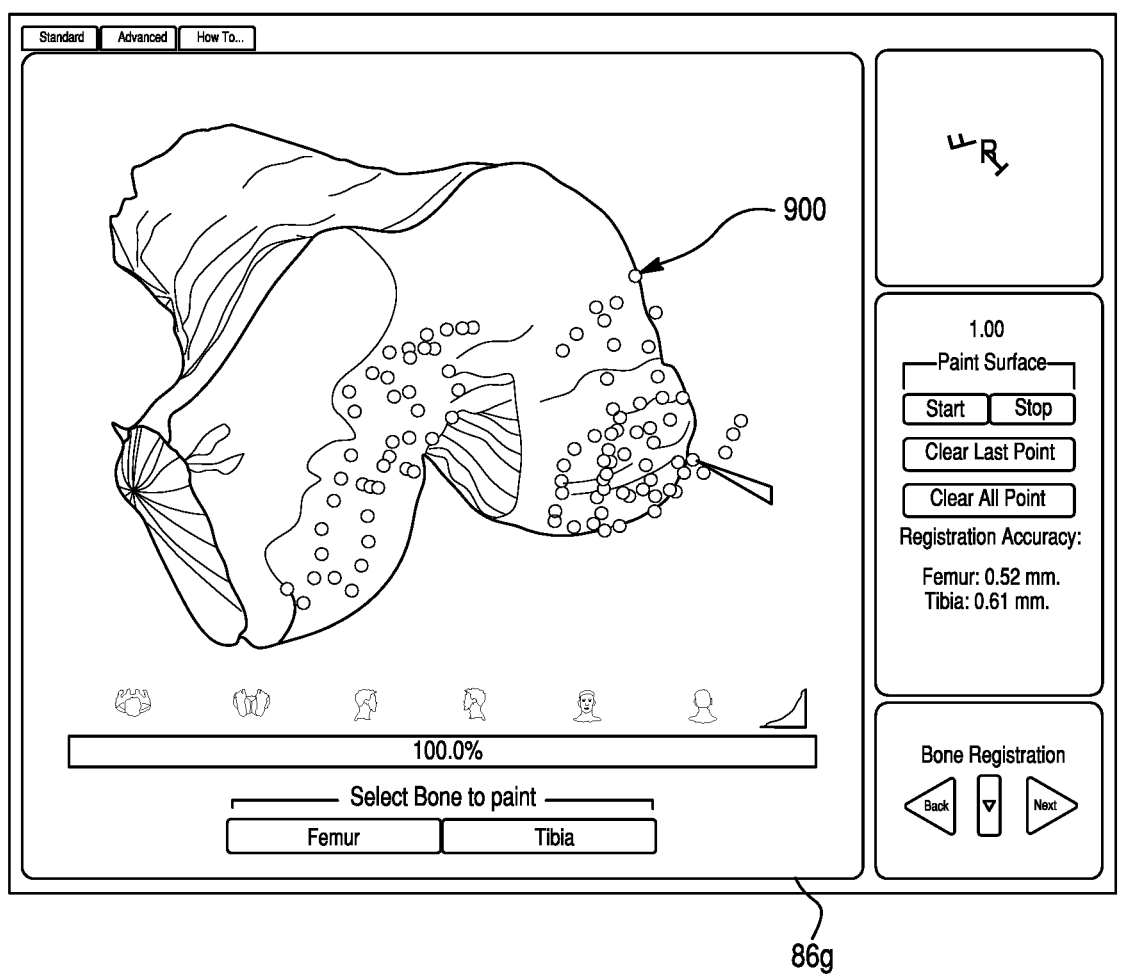
FIG. 18 is a view of an embodiment of a surgical navigation screen showing a registration step according to the present invention.
Figure 19:
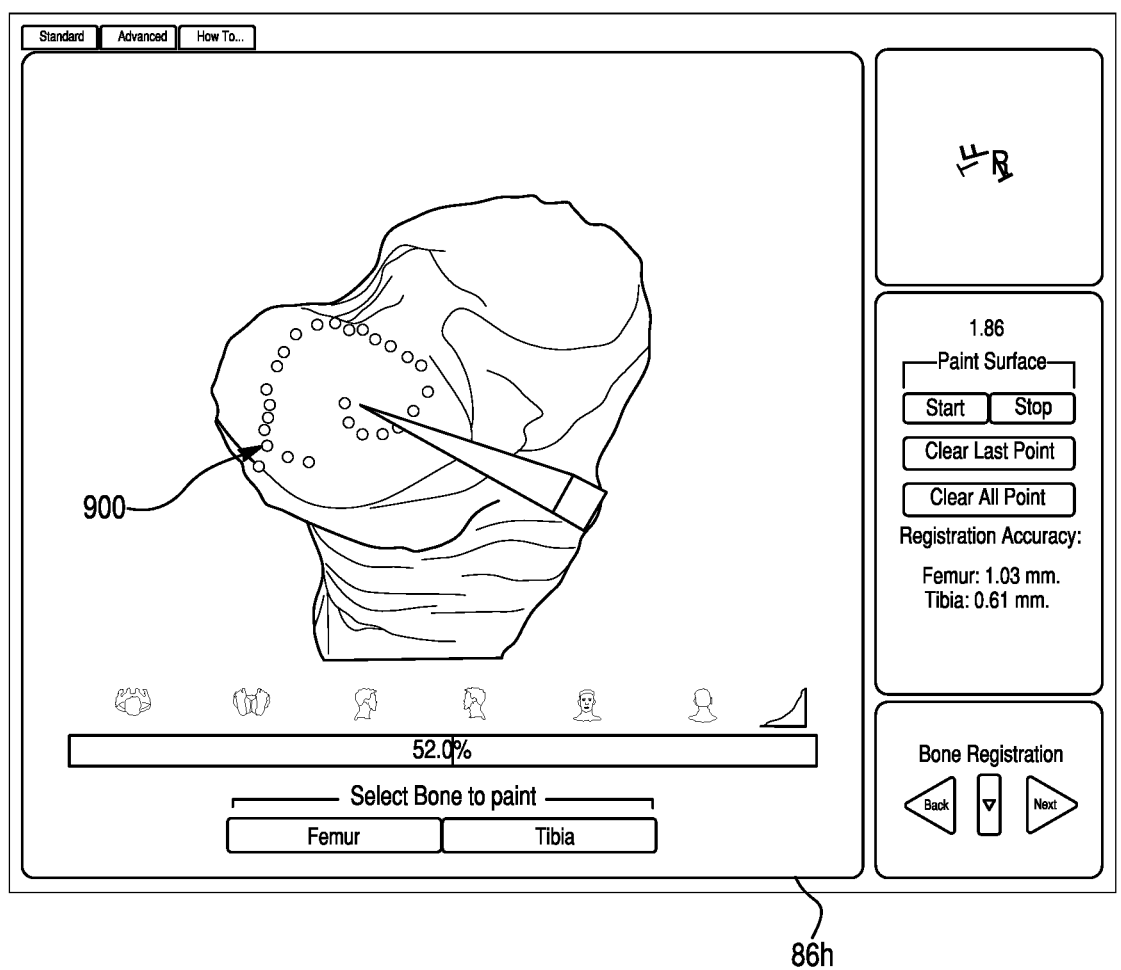
FIG. 19 is a view of an embodiment of a surgical navigation screen showing a registration step according to the present invention.

After the anatomy trackers 43a and 43b are fixed to the patient, the process proceeds to step S8 in which the patient's physical anatomy is registered to the representation of the anatomy. In other words, the physical anatomy is registered to image space. For example, the femur F and the tibia T of the patient may be registered in standard fashion using a paired-point/surface match approach based on the femoral and tibial landmarks specified in steps S3 and S4, respectively. The surgical system 10 generates screens to guide the user through the registration process. For example, a screen 86a (FIG. 12) instructs the user to rotate the femur F to find a center of a hip of the leg L. In one embodiment, the surgical system 10 determines the hip center by determining a center of a pivot point of the femur F based on motion of the anatomy tracker 43a during the rotation of the femur F. Screens 86b, 86c, 86d, 86e, and 86f (shown in FIGS. 27, 28, 29, 30, and 31, respectively) instruct the user to point a registration probe to various anatomical landmarks (e.g., medial malleolus, lateral malleolus, medial epicondyle, lateral epicondyle, posterior border of anterior cruciate ligament (ACL) attachment, etc.) and to select the landmarks. For example, the user may place a tip of a tracked registration probe on the relevant landmark and select the landmark with a foot pedal or other input device 25. When the user selects the landmark, the detection device 41 acquires data related to the pose of the registration probe, which is then used to calculate the location of the landmark. Based on the landmark pose data and the landmark designations in the diagnostic images (in steps S3 and S4), the surgical system 10 registers the physical anatomy to the diagnostic images by determining a correspondence between the physical landmarks on the patient and the landmarks in the diagnostic images. The accuracy of this landmark-based registration may be improved by acquiring surface data for the femur F and the tibia T. For example, the surgical system 10 may generate a screen 86g (FIG. 18) instructing the user to touch points on (or "paint") a surface of a distal end of the femur F with the registration probe. As the user paints the surface (e.g., by inserting a tip of the registration probe through the incision 128), the surgical system 10 periodically acquires a position of the probe tip and displays the acquired tip positions on the screen 86g as dots 900. For bone surfaces that are overlaid with cartilage, a sharp probe may be used to pierce the cartilage and collect points on the surface of the bone (as opposed to points on the surface of the cartilage). Similarly, the surgical system 10 generates a screen 86h (FIG. 19) and instructs the user to paint a surface of a proximal end of the tibia T with the registration probe. As the user paints the surface (e.g., by inserting the probe tip through the incision 128), the surgical system 10 periodically acquires a position of the probe tip and displays the acquired tip positions on the screen as the dots 900. As with the femur, a sharp probe may be used to pierce any cartilage so that points on the surface of the bone (as opposed to the surface of the cartilage) are collected. Additionally, a hooked probe may be used to facilitate the collection of points at a posterior margin of the tibial plateau. The result of the registration process of step S8 is a registration transform that relates a coordinate system of the physical anatomy to a coordinate system of the representation of the anatomy.

Preferably, step S8 includes identifying at least one interface on the anatomy and determining a position of a checkpoint of the interface in a coordinate frame of reference, such as by digitizing the checkpoint when a registration probe is in contact with the interface. The interface may be, for example, a painted portion on a bone of the patient, a divot made in the bone, or a mechanical interface disposed on the bone. During the surgical procedure, the checkpoint enables the user to verify that the surgical system 10 is properly configured. For example, the user can touch the tip of the tool 50 to the interface to confirm that the tracking system 40 is properly configured (e.g., the tracking elements are not occluded and are still properly aligned relative to the anatomy and/or the haptic device 30, etc.), that the tool 50 is correctly installed (e.g., properly seated, shaft not bent, etc.), and/or that any other object is properly mounted, installed, calibrated, and the like. In this manner, the checkpoint enables the surgical system 10 to confirm that all elements involved in relating the tip of the tool 50 to the anatomy of the patient remain in calibration and that the tracking elements are updating properly.

In one embodiment, the checkpoint is established as follows. In step S8, after locating the hip center (screen 86a of FIG. 12) and prior to collecting any landmarks (screen 86b of FIG. 13), the user designates two interfaces on the anatomy that enable two reference points (or checkpoints) to be defined—a first interface on the femur F for defining a first checkpoint associated with the femur F and a second interface on the tibia T for defining a second checkpoint associated with the tibia T. Each interface should be placed so that it is accessible with a registration probe but is not located on a portion of the bone that will be removed during the surgical procedure. An interface may be established, for example, by marking the bone with methylene blue (or other clinical marking product), by creating a small (e.g., approximately 1 mm diameter) divot on the bone (e.g., using a drill bit), and/or by implanting a temporary fiducial marker (or mechanical interface) on the bone. When the interface is a marking or divot on the bone, the interface itself is an anatomical reference point that comprises the checkpoint. In contrast, when the interface is a mechanical interface, the checkpoint is a datum defined based on an engagement of a registration probe with the mechanical interface, as described below in connection with a mechanical interface 510. In one embodiment, the surgical system 10 displays a screen 186a (shown in FIG. 21) instructing the user to identify (e.g., touch or contact) the first interface on the femur F. When the user contacts the first interface with the tip of the registration probe, the surgical system 10 digitizes the first checkpoint and establishes a point in the coordinate space of the anatomy tracker 43a. The surgical system 10 may also instruct the user to verify (or re-touch) the first interface to ensure that the first checkpoint is accurately captured. The surgical system 10 then displays a screen 186b (shown in FIG. 22) instructing the user to identify (e.g., touch or contact) the second interface on the tibia T. When the user contacts the second interface with the tip of the registration probe, the surgical system 10 digitizes the second checkpoint and establishes a point in the coordinate space of the anatomy tracker 43b. The surgical system 10 may also instruct the user to verify (or re-touch) the second interface to ensure that the second checkpoint is accurately captured. After the first and second checkpoints have been established, the user proceeds with registration by selecting landmarks and painting surfaces of the femur F and the tibia T (as described above in connection with step S8). If desired, the first and second checkpoints may be transformed into image space (e.g., using the registration transform obtained in step S8) and displayed on the display device 23 to aid in assessing the success of the registration.

According to another embodiment, the interface is a mechanical interface that has a portion configured to be affixed to the anatomy and a portion configured to engage an instrument. For example, the mechanical interface can be configured to engage with a burr, a router, a probe, and/or the like. One advantage of a mechanical interface is that the mechanical interface is stabilized relative to the bone and the bone coordinate system. Thus, the mechanical interface can improve the checkpoint verification procedure by enabling instruments, such as probes/burrs, to be positioned relative to the checkpoint with a high degree of repeatability. Furthermore, a mechanical interface can advantageously provide accurate verification because the mechanical interface will not be obscured by bodily fluids or tissues, or deformed by repeated probing.

According to an embodiment, the surgical system 10 can use a mechanical interface to determine the position of an instrument. Such a step can verify if an instrument is in the correct position relative to a patient's anatomy and can verify if the instrument is the correct size. Such verification steps can quickly provide a user with information useful for determining if the system is performing as intended and/or being used properly before any non-reversible cuts are made to the patient's anatomy. The position of the checkpoint of the mechanical interface can be digitized, such as with a registration probe as described in the digitizing steps above. Furthermore, the position of the checkpoint of the mechanical interface can be verified repeatedly during the surgical process. In a further example, different-sized instruments can be contacted with the mechanical interface to determine if a distance between a tip of the instrument (e.g., when the instrument is a sharp probe, blunt probe, or router) or a center of the tip of the instrument (e.g., when the instrument is a burr) and the checkpoint is less than a predetermined tolerance. The checkpoint of the mechanical interface may be any suitable datum, such as a portion of the mechanical interface (e.g., a surface), a datum defined relative to a portion of the mechanical interface, or a datum defined relative to an instrument engaged with the mechanical interface. For example, the datum may be a point, line, or plane defined relative to a surface of the mechanical interface. Preferably, however, the datum is defined by a location of a tip of a probe when the probe is "bottomed out" (i.e., inserted as far as possible) in the mechanical interface, such as a datum Db shown in FIG. 24 (for a blunt probe 600) or a datum Ds shown in FIG. 28 (for a sharp probe 640). In one embodiment, contacting the mechanical interface with an instrument can verify whether or not a position of the surgical tool has an expected correspondence to a position of the checkpoint (or datum). If so, all steps involved with relating a patient's anatomy to an instrument, such as a burr, were correctly established, and that all tracking devices are accurately being updated.

According to an embodiment, a surgical system 10 can include a verification checkpoint system that can be configured to perform various tests, such as on information gathered from a mechanical interface. For example, the verification checkpoint system can test for three conditions: 1) if a bone tracker (such as anatomy trackers 43a, 43b) has not moved, 2) whether the position of the instrument, such as a burr (i.e. the surgical tool 50), on the end effector is correct, and 3) whether the instrument, such as a burr, is the correct size. According to a further embodiment, the verification checkpoint system compares an actual offset (the distance between the tip of the instrument or the center of the tip of the instrument and the checkpoint of the mechanical interface)) to an ideal offset (a predetermined distance between the expected (or ideal) position of the tip of the instrument or the center of the tip of the instrument and the checkpoint of the mechanical interface when all three conditions are met). The predetermined distance is calculated from the known geometry of the mechanical interface and the tool tip. If all three conditions are met, the difference between the actual offset and the ideal offset should be below a predetermined threshold. For example, a predetermined threshold of 1.0 mm could be used to verify that all three conditions are met.

According to an embodiment, once a mechanical interface has been affixed to a portion of a patient's anatomy, an instrument, such as a blunt probe or burr, can be inserted into an interface portion of the mechanical interface. For example, the interface portion of a mechanical interface can include divot or interface surface that is configured to engage with the instrument.

Figure 23A:
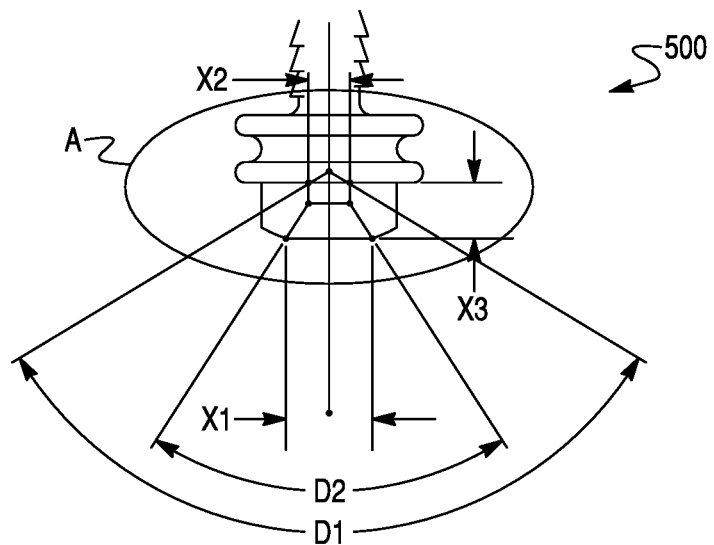
FIG. 23A is a sectional view of an embodiment of a mechanical interface 500 according to the present invention
Figure 23B:
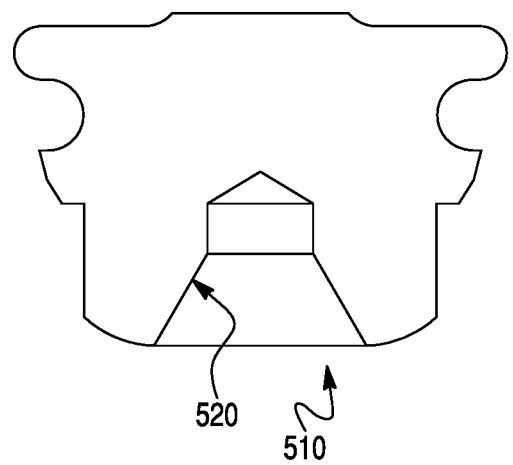
FIG. 23B is an enlarged view of region A indicated in FIG. 23A.

FIG. 23A is a sectional view of a mechanical interface 500, according to an embodiment. FIG. 23B is an enlarged view of region A indicated in FIG. 23A. As shown in the example of FIG. 23B, a mechanical interface 500 can include an interface 510 or divot that is configured to engage with an instrument. In particular, the interface 510 can include an interface surface 520 configured to engage with the instrument. The interface surface 520 can advantageously position an instrument within the interface 510 of the mechanical interface 500, thereby providing for accurate determinations of the position of the mechanical interface 500, the size of the instrument, and other features described herein. For example, the interface surface 520 can be a conical or frustoconical surface. Such an interface surface configuration can act as a mechanical amplifier in that the locations of different-sized instruments can vary by a degree that is significant enough to be detected. Because the locations of different-sized instruments vary to such a degree, the verification checkpoint system is capable of determining which particular instrument, such as a burr or probe, is being seated within the interface 510 of the mechanical interface 500.

The interface 510 or divot of a mechanical interface 510 can be designed so that the tip of an instrument (such as a probe) will "bottom out" at a predetermined location within the interface or divot. To bottom out the instrument, the surgeon inserts the tip of the instrument into the mechanical interface 510 until the instrument comes to a hard stop and cannot be inserted any further. The predetermined 3D location then becomes the established checkpoint, which is a reference in the physical space of the bone tracker (such as anatomy trackers 43a, 43b). Because the location of the mechanical interface is known with respect to the bone tracker, the position of the tip of the instrument, and thus the position of the checkpoint (or datum), is also known through the bone tracker, the haptic guidance system, the geometry of the instrument, and the mount of the instrument. Once the checkpoint is established, other instruments, such as a surgical burr, can be inserted into the mechanical interface 510 and the position of the tip or the center of the tip of the instrument determined and compared to the position of the checkpoint. Specifically, a distance between a position of the checkpoint of the mechanical interface and a position of the instrument, such as a position of the tip of the instrument or the center of the tip of the instrument, can be calculated. If this calculated distance is less than a predetermined value, the verification checkpoint system will determine that the surgical procedure is proceeding accordingly. If not, the surgical system 10 can be configured to provide a warning to an operator, such as a visual warning, an audible warning, or any other warning known in the art. For example, the calculation of the distance between a position of the checkpoint and a position of the instrument can be used to verify any movement of an anatomy tracker, to verify accuracy of mechanical interface registration, to calibrate the haptic guidance system, to verify proper mounting of an instrument in an end effector, and/or to verify that the correct instrument is mounted. In a further example, the mechanical interface can be used to verify movement of an array of markers. If the array has moved, a newly digitized mechanical interface will appear to be in a different location than the one when the mechanical interface was originally digitized. If the distance between these locations is greater than a predetermined threshold (such as, for example, about 2.00 mm) the array will be deemed to have moved and the registration for that portion of the patient's anatomy, such as a bone, will have to be repeated.

According to an embodiment, the interface 510 of a mechanical interface 500 can be configured to have dimensions suitable for engagement with various instruments. For example, the interface 510 of a mechanical interface 500, as shown in the example of FIG. 23A, can be configured to have a dimension X1 of about 2.0 to 3.0 mm, or more preferably about 2.5 to 3.5 mm, or more preferably about 3.0 mm; a dimension X2 of about 0.5 to 2.5 mm, or more preferably about 1.0 to 2.0 mm, or more preferably about 1.5 mm; a dimension X3 of about 1.0 to 3.0 mm, or more preferably about 1.5 to 2.5 mm, or more preferably about 2 mm; an angle D1 of about 110° to 130°, or more preferably about 115° to 125° mm, or more preferably about 118°; an angle D2 of about 50° to 70°, or more preferably about 55° to 65° mm, or more preferably about 60°.

Figure 24:
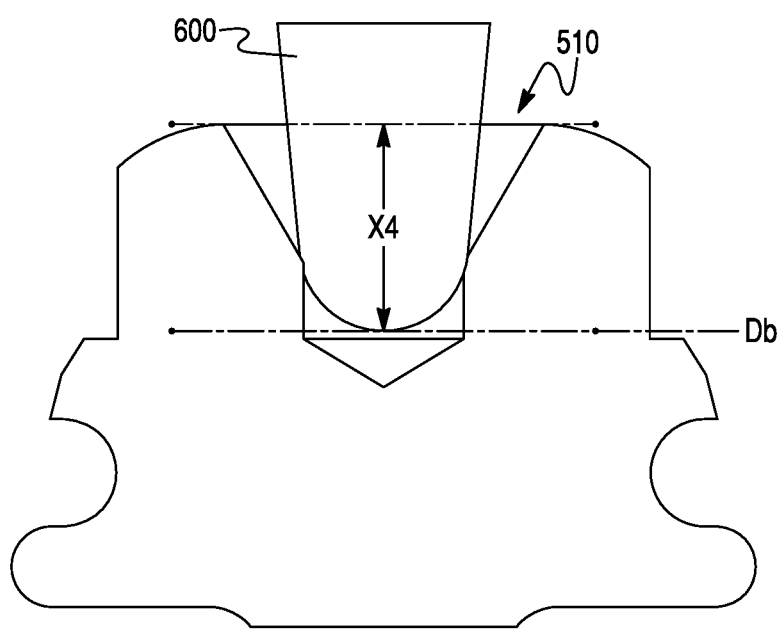
FIG. 24 shows a sectional view of an embodiment of a blunt probe that has been inserted into the interface 510 of a mechanical interface 500 according to the present invention.
Figure 28:
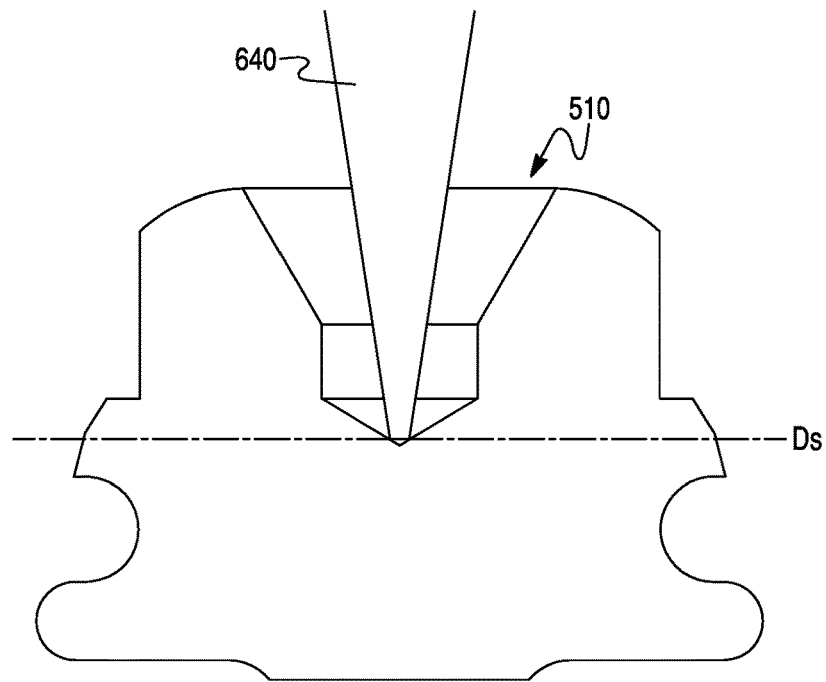
FIG. 28 shows a sectional view of an alternative embodiment of a probe with a sharp point that has been inserted into an interface of a mechanical interface according to the present invention.

FIG. 24 shows a sectional view of a blunt probe 600 that has been inserted into the interface 510 of a mechanical interface 500, according to an embodiment. As shown in the example of FIG. 24, a blunt probe 600 can be configured to be inserted into the interface 510 of a mechanical interface 500 so that the blunt probe 600 bottoms out. The location of the tip of the blunt probe 600 when the blunt probe 600 is bottomed out may be used to define the checkpoint, such as a datum Db. The datum Db may be located, for example, a distance X4 from the surface of the interface 510 of the mechanical interface 500. In one embodiment, the distance X4 can be about 1.00 to 3.00 mm, or more preferably about 1.50 to 2.50 mm, or more preferably about 1.88 mm for the blunt probe 600. The position of the tip of the blunt probe 600 (i.e., the datum Db) will become an established checkpoint that can be used to determine distances for other instruments and to discriminate between instruments, as will be described below. The actual distance between the checkpoint (the datum Db) as measured by the tip of the blunt probe 600 and the tip or the center of the tip of the tool being checked will be determined, as described above, and compared to a predetermined value or ideal offset. Such a predetermined value can depend upon the dimension of the blunt probe 600 and the dimensions of the interface 510, as described above. Alternatively, instead of a blunt probe 600, a sharp probe 640 may be used to establish the checkpoint. A checkpoint established using the sharp probe 640 may correspond to a datum Ds, which is the location of the tip of the sharp probe 640 when the sharp probe 640 is bottomed out in the mechanical interface 510, as shown in FIG. 28.

Figure 25:
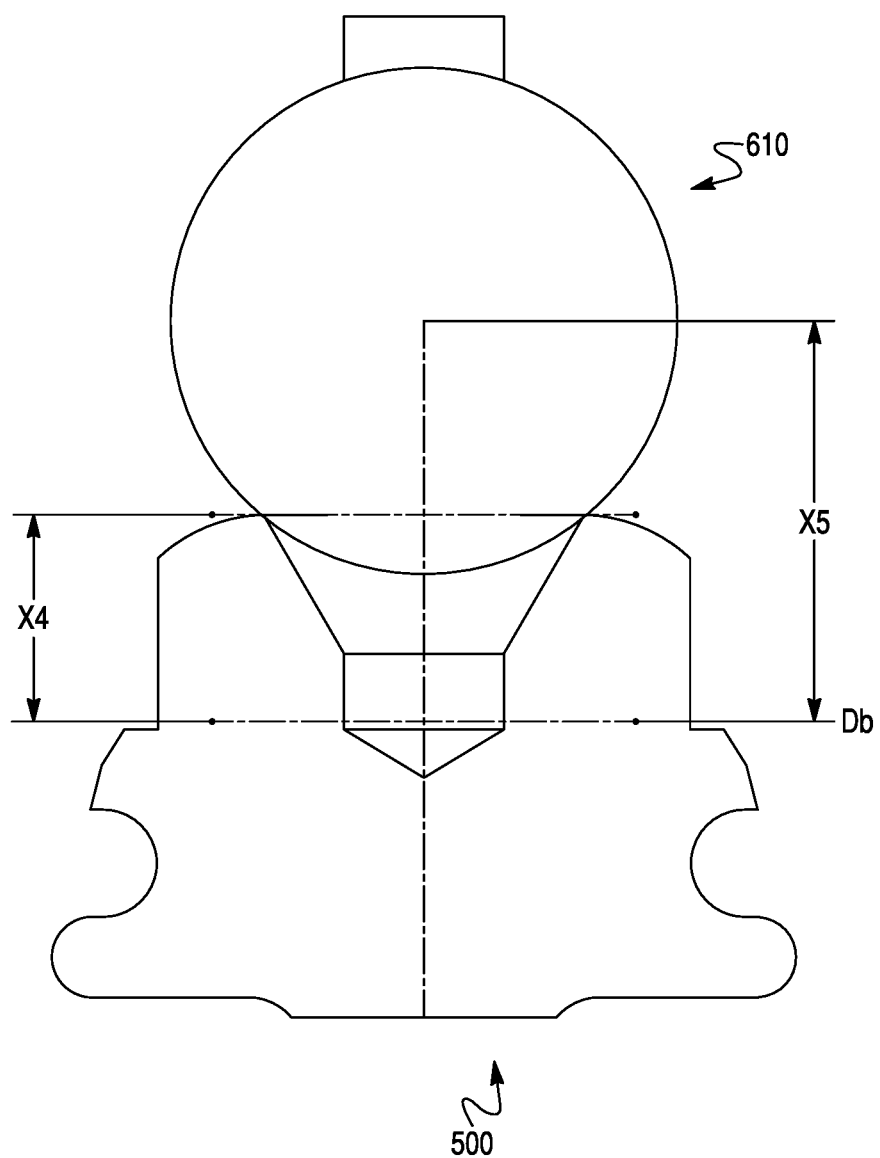
FIG. 25 shows a sectional view of an embodiment of a 6 mm burr inserted into the interface 510 of a mechanical interface according to the present invention.

Compared to a blunt probe 600 and the checkpoint established by bottoming out the blunt probe 600 in the mechanical interface 510 (as represented by the datum Db), an instrument, such as a burr, can be configured with different dimensions so that differently dimensioned instruments have different distances between the checkpoint and a position on the instrument. For example, the mechanical interface 510 can be configured so that a 1 mm burr can be inserted deeper into the interface 510 than the blunt probe 600, such as, for example, about 0.10 to 0.30 mm deeper, or more preferably about 0.26 mm deeper. Similarly, the mechanical interface 510 can be configured so that a 2 mm burr can not be inserted as deeply into the mechanical interface 510 as the blunt probe 600. For example, the 2 mm burr may be about 1.28 mm more shallow. Because the 1 mm burr and the 2 mm burr bottom out at different locations in the mechanical interface 510, they will have different distances from the established checkpoint. In another example, FIG. 25 shows a sectional view of a 6 mm burr 610 inserted into the interface 510 of a mechanical interface, according to an embodiment. The distance X5 from a position of the 6 mm burr 610, such as a center of the tip of the 6 mm burr 610, to the registered checkpoint corresponding to the tip of the blunt probe 600 (as represented by the datum Db) is determined. The distance X5 is then compared to a predetermined value or ideal offset. The comparison of the distance X5 and the predetermined value can be used to provide information about the position of the mechanical interface, the type or size of instrument, movement of anatomy trackers, and other information as described above. According to a further embodiment, the distance X5 can be about 3.50 to 5.50 mm, or more preferably about 4.00 to 5.00 mm, or more preferably about 4.49 mm.

Figure 26:
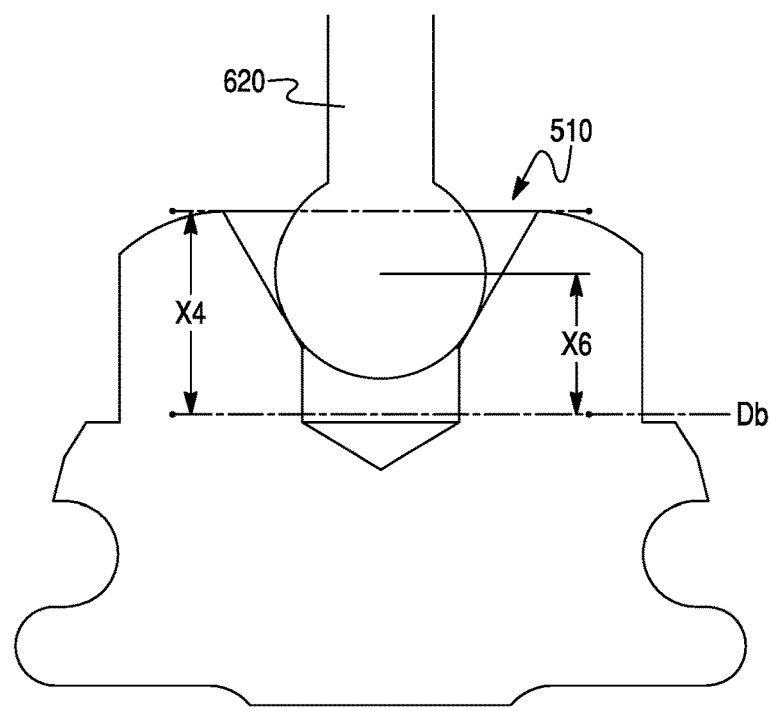
FIG. 26 shows a sectional view of an embodiment of a 2 mm burr inserted into the interface 510 of a mechanical interface according to the present invention.

FIG. 26 shows a sectional view of a 2 mm burr 620 inserted into the interface 510 of a mechanical interface, according to an embodiment. The distance X6 from a position of the 2 mm burr 620, such as a center of the tip of the 2 mm burr 620, to the registered checkpoint corresponding to the tip of the blunt probe 600 (as represented by the datum Db) is determined. The distance X6 is then compared to a predetermined value or ideal offset. The comparison of the distance X6 and the predetermined value can be used to provide information about the position of the mechanical interface, the type or size of instrument, movement of anatomy trackers, and other information as described above. According to a further embodiment, the distance X6 can be about 0.50 to 2.00 mm, or more preferably about 0.75 to 1.75 mm, or more preferably about 1.28 mm.

Figure 27:
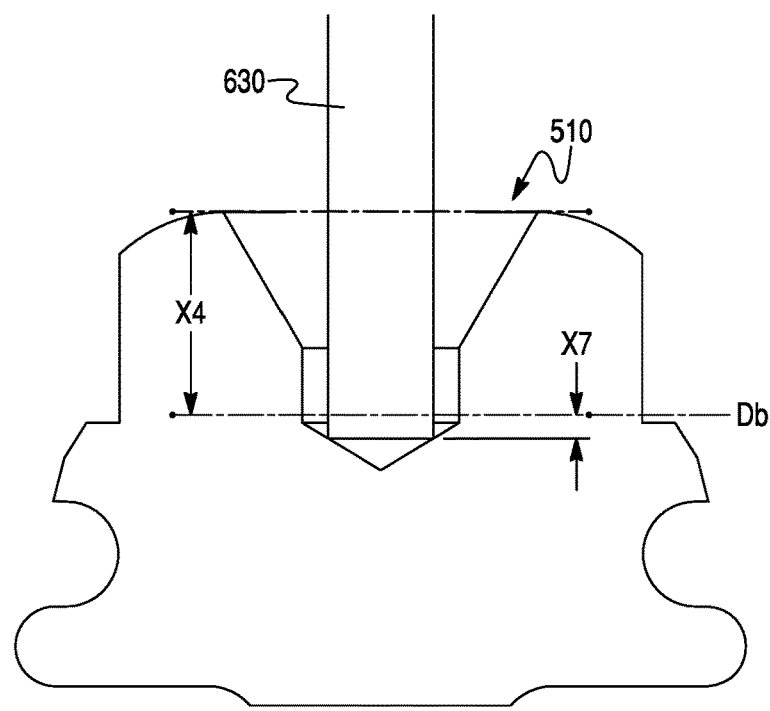
FIG. 27 shows a sectional view of an embodiment of a router inserted into the interface 510 of a mechanical interface according to the present invention.

FIG. 27 shows a sectional view of a router 630 inserted into the interface 510 of a mechanical interface, according to an embodiment. For example, the router 630 can be a 1.2 mm router. The distance X7 from a position of the router 630, such as a tip of the router 630, to the registered checkpoint corresponding to the tip of the blunt probe 600 (as represented by the datum Db) is determined. The distance X7 is then compared to a predetermined value or ideal offset. The comparison of the distance X7 and the predetermined value can be used to provide information about the position of the mechanical interface, the type or size of instrument, movement of anatomy trackers, and other information as described above. According to a further embodiment, the distance X7 can be about 0.05 to 0.35 mm, or more preferably about 0.15 to 0.25 mm, or more preferably about 0.21 mm.

FIG. 28 shows a sectional view of an alternative embodiment of a probe 640 with a sharp point that has been inserted into an interface 510 of a mechanical interface. The sharp point of the probe 640 permits the probe to be inserted deeper into the interface 510 of the mechanical interface. Therefore, a sharper probe geometry provides a registered checkpoint for the probe that is closer to the bottom of the interface 510 than a probe with a blunt tip geometry. Such a sharp tip geometry may be used when one desires a registered checkpoint, which corresponds to the tip of the probe, that more closely corresponds to the bottom of the interface 510 of the mechanical interface. In one embodiment, when the sharp probe 640 is used to establish the checkpoint (as represented by the datum Ds), a distance between a tip of the blunt probe 600 and the datum Ds is about 0.5 mm; a distance between the center of the tip of the 1 mm burr and the datum Ds is about 0.24 mm; a distance between the center of the tip of the 2 mm burr and the datum Ds is about 1.78 mm; and a distance between the center of the tip of the 6 mm burr and the datum Ds is about 4.99 mm.

Because of their geometry, some instruments are easier to discriminate from other instruments. For example, because a 6 mm burr has the largest offset, the 6 mm burr is the easiest to discriminate from other burrs, which can have more similar offset values. According to a further embodiment, the interface of the mechanical interface can be designed to increase the differences between the ideal offsets and increase the ability of the checkpoint verification procedure to discriminate between the various burrs.

According to an embodiment, the mechanical interface can include a feature to remind a surgeon to remove the mechanical interface before closing the incision. For example, a suture can be attached to the mechanical interface, with a remaining length of suture thread that extends outside of the incision to serve as a reminder for the surgeon to remove the checkpoint before closing the incision. In another example, a piece of surgical tape can be applied to the mechanical interface with a written reminder to remove the checkpoint or a warning screen can be provided that reminds the surgeon to remove any checkpoints affixed to the patient.

Figure 29:
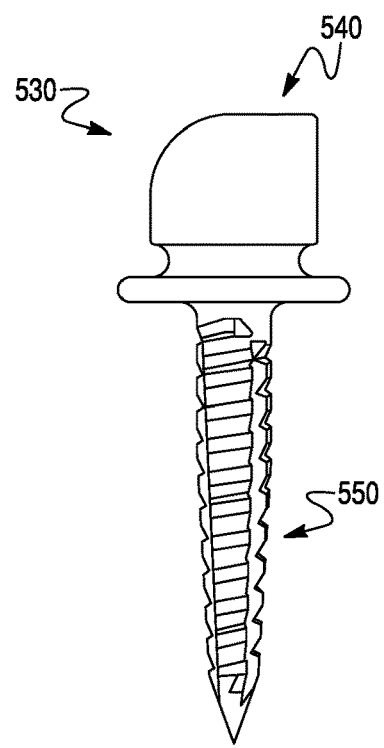
FIG. 29 shows a side view of an embodiment of a mechanical interface that is configured to be impacted into the femur of a patient according to the present invention.
Figure 30:
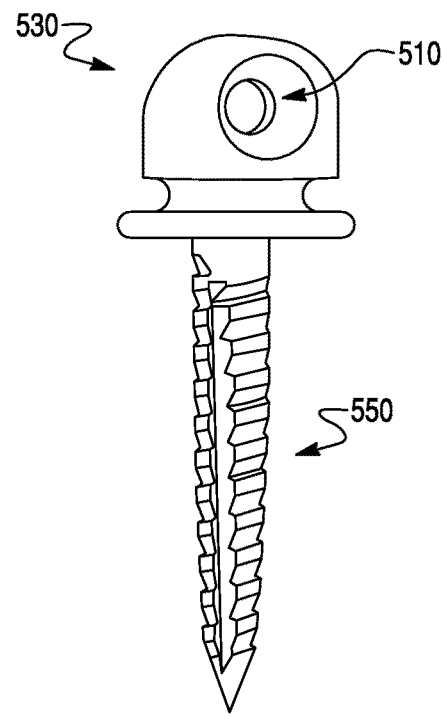
FIG. 30 shows a side view of the femoral mechanical interface from another angle.

FIG. 29 shows a side view of a mechanical interface 530 that is configured to be impacted into the femur of a patient, according to an embodiment. Such a mechanical interface 530 can be used to establish a reference point on the femur of the patient. The femoral mechanical interface 530 can be configured to have a low profile to minimize impingement on soft tissue. For example, the mechanical interface 530 can include a head portion 540 and a post 550 for insertion into the femur. For example, head portion 540 can include a square head over a round flange, as shown in the example of FIG. 29, and the post 550 can include a screw to facilitate insertion of the mechanical interface 530 into the bone. FIG. 30 shows a side view of the femoral mechanical interface 530 from an angle to more clearly show the interface 510 within the head portion 540 of the mechanical interface 530. As shown in the example of FIG. 30, the interface 510 of the femoral mechanical interface 530 can be configured to be located on a side of the head portion 540 (as opposed to the top surface of the head portion 540) to permit easier access to the interface 510 during a surgical procedure. The interface 510 can be configured according to any of the embodiments described herein.

Figure 31:
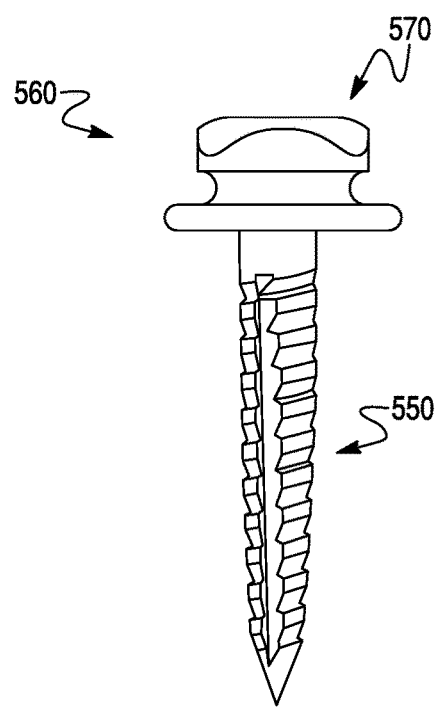
FIG. 31 shows a side view of an embodiment of a mechanical interface that is configured to be impacted into the tibia of a patient according to the present invention.
Figure 32:
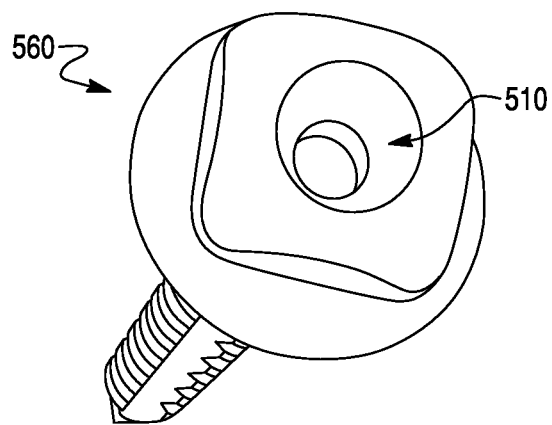
FIG. 32 shows a top view of the tibial mechanical interface.

FIG. 31 shows a side view of a mechanical interface 560 that is configured to be impacted into the tibia of a patient. Such a mechanical interface 560 can be used to establish a reference point on the tibia of the patient. The mechanical interface 560 can include a head portion 570 and a post 550 for insertion into the tibia. The tibial mechanical interface 560 can be configured to have a low profile to minimize impingement on soft tissue. For example, head portion 570 can include a flat head over a round flange, as shown in the example of FIG. 31, and the post 550 can include a screw to facilitate insertion of the mechanical interface 560 into the bone. FIG. 32 shows a top view of the tibial mechanical interface 560 to more clearly show the interface 510 within the head portion 570 of the mechanical interface 560. The interface 510 can be configured according to any of the embodiments described herein.

Figure 33:
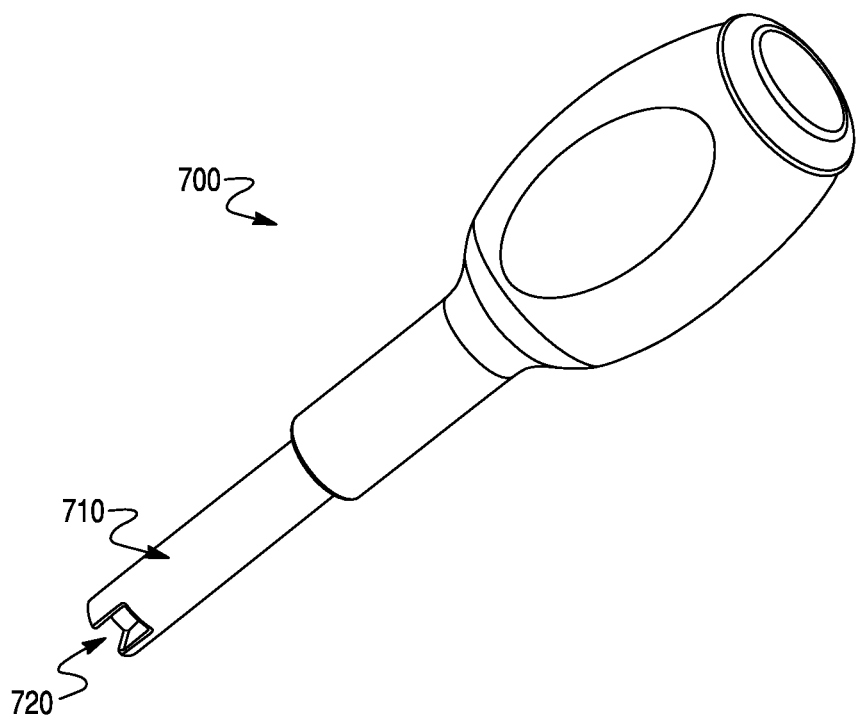
FIG. 33 shows a plan view of an embodiment of an impactor/extractor tool according to the present invention.

FIG. 33 shows a plan view of an impactor/extractor tool 700, according to an embodiment. As shown in the example of FIG. 33, the impactor/extractor tool 700 can have a square shaft 710 configured to fit over the square head portion 540, 570 of the mechanical interface 530, 560 so that the mechanical interface (or checkpoint) may be "screwed" into or out of the bone. For example, as shown in FIG. 33, the end of the shaft 710 can have a female portion including a slot 720 that is about 6 mm long and that extends to the end of the shaft 710. The female portion may also include an undercut feature. In operation, the surgeon can slide the impactor/extractor tool 700 over the checkpoint 530, 560 from the side so that the round flange of the checkpoint 530, 560 engages the undercut feature. With the mechanical interface 530, 560 held in the impactor/extractor tool 700, the surgeon can position a tip of the checkpoint 530, 560 on a bone insertion site and strike an impaction pad on the opposite end of the impactor/extractor tool 700 with a mallet to drive the mechanical interface 530, 560 into the bone. During insertion, the slot 720 can also act as a "window" so that the surgeon can see the orientation of the mechanical interface 530. To remove the mechanical interface 530, 560, the surgeon can engage the impactor/extractor tool 700 with the mechanical interface, as described above, and unscrew the mechanical interface 530, 560 from the bone.

According to an embodiment, a mechanical interface can be made of a material typically used for orthopedic devices, such as, for example, 316L SST, 17-4PH SST, Ti6AL4V (Titanium alloy), Titanium CP (commercially pure). Alternatively, the mechanical interface could be made of a bioabsorbable material so that the checkpoint can be left in the patient and eventually absorbed by the body of the patient. For example, the head of a mechanical interface can be broken off after use, with the post to be left in place to be reabsorbed by the bone.

According to the embodiments described above, the orientation of the mechanical interface would not be known when the mechanical interface is affixed to the bone. One way to determine the orientation of the mechanical interface is to determine the orientation of the long axis of the interface or divot of the mechanical interface. However, if the mechanical interface is not tracked, the axis of the divot will not be known. In contrast, the location of the axis of the divot 47A (described above in the discussion of the end effector tracker 47) is known relative to the geometry of the reflective spheres S4 on the end effector tracker 47. Because the spheres S4 are tracked by the camera and the relative geometry between the spheres S4 and the axis is known, the orientation of the axis of the divot 47A is known.

According to an embodiment, the mechanical interface may be configured so that the orientation of the mechanical interface can be determined, for example, by determining an axis of the divot of the mechanical interface. When the orientation of the mechanical interface is not known, the verification process tests only if the instrument, such as a tip of a probe or a center of a tip of a burr, which is engaged with the mechanical interface is approximately at an "ideal" distance from the checkpoint that has been previously established with a blunt or sharp probe. Because orientation of the mechanical interface is not known, the expected location of the tip or the center of the tip of the instrument is not known and therefore only the ideal distance of the tip or the center of the tip of the instrument from the established checkpoint is known (based on the geometry of the mechanical divot). In order to compute the expected location of the tip or the center of the tip of the instrument (as opposed to just its distance from the established checkpoint), the orientation of the interface of the mechanical interface must be known or estimated. For example, the orientation of the interface of the mechanical interface could be determined from the orientation of the blunt or sharp probe when the checkpoint for the tip of the probe is established. Alternatively, the interface of the mechanical interface can be redesigned so that it has a mating surface for a specially designed probe such that the probe seats in the interface in such a way that the orientation of the interface can be precisely determined. According to another example, the mechanical interface could be tracked to provide its orientation. However, the mechanical interface would be difficult to track because it must be small enough not to interfere with any soft tissue or instruments used during the surgical procedure. Thus, adding reflective spheres to track the mechanical interface is impractical because the spheres would make the mechanical interface bulky. However, the mechanical interface could possibly be tracked with a non-optical tracking system, such as an electromagnetic or radiofrequency system or with sensors, such as RFID sensors.

Once the orientation of the interface or divot is known or estimated, the expected location of the center of a tip of a burr (i.e., the burr center) can be computed by the simple formula:

$$C_b = C_p(O^*A_d)$$

where $C_b$ is the location of the burr center, $C_p$ is the checkpoint picked by the probe, O is the offset (given by the geometry of the interface of the mechanical interface) to the burr center, and $A_d$ is the vector defining the central axis of the divot and pointing from the base to the top of the divot. The "expected location" of the center of the burr can then be directly compared to the actual location of the center of the burr.

According to an embodiment, the mechanical interface can include at least one feature configured to provide information about the mechanical interface. The feature may be configured to be detected by a detection device, and the information provided by the feature may include, for example, a position, an orientation, a size, an identity (e.g., part number), and/or any other useful information regarding the mechanical interface. For example, in operation, the feature can function as a reference point or datum for the mechanical interface (e.g., a shape, curve, point, axis, etc.). Thus, the feature may be used as a basis for calculating or determining a position and/or an orientation of the mechanical interface. In this manner, the feature may be used to provide additional degrees of freedom for the mechanical interface.

According to a further embodiment, the feature configured to provide information about the mechanical interface may be integrated with the mechanical interface in any known manner. For example, the feature may be embedded in the mechanical interface, affixed to the mechanical interface (e.g., using adhesive), formed on a surface of the mechanical interface (e.g., by etching, cutting, marking, etc.), and/or formed integrally with the mechanical interface. The feature can take any of a variety of forms, some of which are described below.

According to a further embodiment, the feature configured to provide information about the mechanical interface can be configured to be detectable (or readable) by a detection device (or detection system) using any suitable detection method. For example, the feature may be detected using optical, electromagnetic, radio, and/or acoustic methods, as are well known. As further examples, the feature may be detected using a laser scanner or infrared camera. As yet additional examples, the feature may be detected using a trackable probe or instrument in combination with an infrared camera or a mechanical arm with joint encoders. The detection device can read the feature after the mechanical interface has been implanted in the patient.

Some specific features and detection devices will now be described. The invention is not intended to be limited to the specific features described, nor is it intended to be limited to the described combinations of features and detection devices. The feature may include, for example, an optical characteristic, such as an optical etching (e.g., a laser etching), an optical marking (e.g., a bar code, a checkerboard pattern, or a grid or array of dots), and/or a marker (e.g., a passive infrared marker) that can be formed or disposed on a surface of the mechanical interface. Such a feature could be detected, for example, with a detection device including a laser scanner or infrared camera.

As another example, the feature configured to provide information about the mechanical interface can include a pattern disposed on a surface of the mechanical interface. The pattern may include, for example, textures, grooves, etchings, and the like. Such a feature could be detected, for example, with a detection device that includes a trackable probe that can be slid over the pattern and an infrared camera that can detect the probe.

As another example, the feature configured to provide information about the mechanical interface can include a landmark or surface characteristic. The landmark or surface characteristic may be an integral or intrinsic part of the mechanical interface that is sufficiently defined and identifiable to function as a recognizable marker (e.g., an articular surface, outlines of anatomical structure, shapes, colors, etc.).

The ability to communicate information from the mechanical interface via the feature and the detection device provides a wide variety of capabilities. For example, if the feature provides information to the detection device regarding the position and/or orientation of the feature, a computing device can calculate or determine the position and/or orientation of the mechanical interface based on that information and a known geometric relationship between the feature and the mechanical interface. The ability to determine the position of the mechanical interface makes it possible to determine the positioning of the mechanical interface relative to another object, relative to a plurality of other objects, and/or relative to a patient's bone. For example, the computing device (in combination with the detection device) can calculate or determine the position and orientation of the mechanical interface relative to one or more tracking arrays, such as an anatomy tracker. The computing device can then compare the relative position of the mechanical interface and the tracker to a desired relationship established during patient registration. If the actual relationship deviates from the desired relationship, corrective action can be taken, such as repeating patient registration.

As yet another example, the feature may be structure that emits one or more signals that provide information. The feature may, for example, emit a directional signal having a known orientation relative to the component. Such a directional signal allows for determining the location and/or orientation of the mechanical interface. Structure that could be used to provide such a directional signal includes, for example, a transmitter positioned on the edge of the mechanical interface. A detection device that could be used to detect the directional signal includes, for example, a receiver capable of triangulating and identifying a position. As another example, the signal emitting structure may include at least one sensor. The sensor may be, for example, a smart label such as a passive radio frequency identification (RFID) tag. The RFID tag is affixed to the surface of the mechanical interface and/or embedded in the mechanical interface and is detectable by an RFID reader that emits radio waves. As a user scans the mechanical interface with the RFID reader, the radio waves power the RFID tag, which then communicates with the RFID reader. One advantage of using a signal emitting structure is that the detection device can obtain information from the structure even when the mechanical interface is not visible or exposed (e.g., when the mechanical interface is covered with tissue such as muscle and skin or occluded by other anatomy).

In operation, the user can contact the femoral and tibial checkpoint verification interfaces any time the user wants to validate the configuration of the surgical system 10, such as when the tool 50 is withdrawn from and then reinserted into the patient. Based on geometric data obtained during establishment of the first and second checkpoints, the surgical system 10 knows a location of the first checkpoint relative to the anatomy tracker 43*a* and a location of the second checkpoint relative to the anatomy tracker 43*b*. Based on geometric data obtained during calibration of the haptic device 30 (as described below in connection with step S9), the surgical system 10 knows a location of a center of the tip of the tool 50 from a pose of the haptic device tracker 45, a pose of the arm 33 of the haptic device 30, the geometry of the tool 50, and the geometric relationship between the tool 50 and the end effector 35. Based on this data, when the user touches the tip of the tool 50 to an interface, the surgical system 10 can calculate a distance between the location of the center of the tip of the tool 50 and the location of the relevant checkpoint. A radius of the tip of the tool 50 is subtracted from the distance to obtain a verification value. Preferably, the verification value is approximately 0.00 mm, which indicates that the location of the tip of the tool 50 and the location of the checkpoint correspond. Some error, however, is acceptable. For example, in one embodiment, if the verification value is equal to or less than a predetermined tolerance (e.g., approximately 1 mm), the system configuration will be deemed acceptable and the user may proceed with the surgical procedure. In contrast, if the verification value exceeds the predetermined tolerance, the surgical system 10 will issue a warning (e.g., a visual, audible, and/or tactile warning) indicating a problem with the system configuration. A problem may exist, for example, if one of tracking elements was bumped by the user during a tool change and is now misaligned, if the tool shaft is bent, and the like. If a warning is issued, registration (step S8) and/or calibration (step S9) should be repeated.

According to a further embodiment, the checkpoint verification system/process can be configured to determine if an instrument, such as a probe or burr, is positioned within a mechanical interface in a stable manner. Confirmation of a stable position advantageously confirms that position readings are being made in an accurate manner. In order to make the verification process as accurate as possible, such as to account for camera movement and to provide a way to detect when the verification should be done, the checkpoint verification system/process can be configured to take a number of burr tip positions, calculate the average of the positions, and calculate a standard deviation of the positions. The acquisition of a mechanical interface position with an instrument, such as a probe, is done by averaging a number of readings, such as, for example, ten, of the position of the instrument with reference to the bone tracker. The averaging of multiple positions provides a better estimate of the position of the interface of the mechanical interface than a single measurement. For example, the system/method can be configured to maintain a running average of instrument positions to compute an estimate of the instrument position with reference to a bone tracker. A distance between a position of the instrument, such as a position of the tip or the center of the tip of the instrument, and each instrument position in a current list is then computed and the standard deviation of this list of distances is compared to a threshold. If the standard deviation is below a predetermined threshold value, the probe is assumed to be static (i.e. steady and not moving). For example, a threshold value of about 0.20, or more preferably 0.15 can be used. The standard deviation can be used to indicate that the instrument has been held steady for a period of time so that the mechanical interface comparison can be made. Another measure, such as a maximum distance relative to a position of the mechanical interface, can also be used to define when the instrument is steady.

In addition to checking the entire system configuration, the checkpoints may also be used to determine whether the anatomy trackers 43a and 43b have moved relative to the femur F and the tibia T, respectively. For example, to determine whether the anatomy tracker 43a has moved relative to the femur F, the user returns to the checkpoint identification screen (e.g., screen 186a of FIG. 56) and re-digitizes the first checkpoint. If the anatomy tracker 43a has moved, the newly digitized checkpoint will appear on the display device 23 in a different location than the original first checkpoint. If the difference between a location of the original first checkpoint and a location of the new checkpoint is greater than a predetermined tolerance (e.g., approximately 2 mm), the surgical system 10 determines that that the anatomy tracker 43a has moved. In this situation, registration (step S8) should be repeated. Similarly, to determine whether the anatomy tracker 43b has moved relative to the tibia T, the user returns to the checkpoint identification screen (e.g., screen 186b of FIG. 57) and re-digitizes the second checkpoint. If the anatomy tracker 43b has moved, the newly digitized checkpoint will appear on the display device 23 in a different location than the original second checkpoint. If the difference between a location of the original second checkpoint and a location of the new checkpoint is greater than the predetermined tolerance, the surgical system 10 determines that that the anatomy tracker 43b has moved. Accordingly, registration (step S8) should be repeated.

In one embodiment, a method for verifying calibration of the surgical system 10 using the checkpoints includes (a) identifying an interface on the anatomy (e.g., a marking, divot, or mechanical interface on a bone); (b) determining a position of a checkpoint of the interface in a coordinate frame of reference (e.g., a coordinate frame of reference of the anatomy or a representation of the anatomy); (c) contacting the interface with a portion of a surgical tool of the haptic device 30 (e.g., with a tip of the tool 50); (d) determining a position of the portion of the surgical tool in the coordinate frame of reference; and (e) determining whether the position of the portion of the surgical tool has an expected correspondence to the position of the checkpoint. The method may also include (f) identifying a second interface on the anatomy (e.g., a second marking, divot, or mechanical interface on a second bone); (g) determining a position of a second checkpoint of the second interface in the coordinate frame of reference; (h) contacting the second interface with the portion of the surgical tool (e.g., with the tip of the tool 50); and (i) determining whether the position of the portion of the surgical tool has an expected correspondence to the position of the second checkpoint. To determine the position of the first and second checkpoints, the surgical system 10 may associate the first and second checkpoints with a representation of the anatomy, such as an image on the display device 23. In one embodiment, to determine whether the position of the portion of the surgical tool has an expected correspondence to the position of the first or second checkpoint, the surgical system 10 determines whether a distance between a tip or a center of the tip of the tool 50 and the first or second checkpoint is equal to or less than a predetermined value (e.g., 1 mm).

One advantage of the checkpoint verification procedure is that the procedure enables the user to confirm that various parts of the surgical system 10 are performing as intended prior to making any non-reversible cuts on the patient's anatomy. For example, the checkpoints can be used to verify registration, calibration of the haptic device 30, and proper operation of the tracking system 40 and tracking elements. As a result, the checkpoints enable the surgical system 10 to simultaneously verify movement of the anatomy trackers 43a and 43b, registration accuracy, movement of the haptic device tracker 45, kinematic calibration of the haptic device 30, proper mounting of the tool 50, and correct tool size.

In step S9, the haptic device 30 is calibrated to establish a geometric relationship or transformation (i.e., position and orientation) between a coordinate system of the haptic device tracker 45 and a coordinate system of the haptic device 30. If the haptic device tracker 45 is fixed in a permanent position on the haptic device 30, calibration is not necessary because the geometric relationship between the tracker 45 and the haptic device 30 is fixed and known (e.g., from an initial calibration during manufacture or setup). In contrast, if the tracker 45 can move relative to the haptic device 30 (e.g., if the arm 34 on which the tracker 45 is mounted is adjustable) calibration is necessary to determine the geometric relationship between the tracker 45 and the haptic device 30.

The surgical system 10 can initiate a calibration procedure by generating a screen instructing the user to calibrate the haptic device 30. Calibration involves securing the haptic device tracker 45 in a fixed position on the haptic device 30 and temporarily affixing the end effector tracker 47 to the end effector 35. The end effector 35 is then moved to various positions in a vicinity of the anatomy (e.g., positions above and below the knee joint, positions medial and lateral to the knee joint) while the tracking system 40 acquires pose data for the trackers 47 and 45 relative to the tracking system 40 in each of the positions. The calibration process of step S9 need not be performed if the haptic device tracker 45 has not moved with respect to the haptic device 30 since the previous calibration and the previously acquired calibration data is still reliable.

In step S10, the user plans bone preparation for implanting a first implant on a first bone. In a preferred embodiment, the first bone is the tibia T, the first implant is the tibial component 74, and bone preparation is planned by selecting a location on a proximal end of the tibia T where the tibial component 74 will be installed. To facilitate implant planning, the surgical system 10 can generate a screen that includes various views of representations of the first and second bones (i.e., the tibia T and the femur F, respectively).

Steps S11 to S15 encompass the bone preparation process. In step S11, the first bone (e.g., the tibia T) is prepared to receive the first implant (e.g., the tibial component 74) by manipulating the tool 50 to sculpt the first bone. In step S12, a trial implant is fitted to the prepared feature on the first bone. In step S13, an initial placement of the second implant (e.g., the femoral component) is planned (or a previously planned placement of the second implant may be revisited and adjusted). In step S14, the second bone (e.g., the femur F) is prepared to receive the second implant after preparation of the first bone. In step S15, a trial implant is fitted to the prepared features on the second bone.

Throughout surgical procedure, the surgical system 10 monitors movement of the anatomy to detect movement of the anatomy and makes appropriate adjustments to the programs running on the computer 21 and/or the computer 31. The surgical system 10 can also adjust a virtual object associated with the anatomy in response to the detected movement of the anatomy.

In step S11, the first bone is prepared to receive the first implant by manipulating the tool 50 to sculpt the first bone. In one embodiment, the tibia T is prepared by forming the medial tibial pocket feature on the proximal end of the tibia T. Upon installation of the tibial component 74, the medial tibial pocket feature will mate with the surface 74a of the tibial component 74 (shown in FIG. 7B).

The occlusion detection algorithm is a safety feature adapted to mitigate risk during a cutting operation in the event tracking elements associated with the haptic device 30 and/or the anatomy become occluded (e.g., the haptic device tracker 45, the anatomy trackers 43a and 43b). An occluded state may exist, for example, when the detection device 41 is unable to detect a tracking element (e.g., when a person or object is interposed between the tracking element and the detection device 41), when a lens of the detection device 41 is occluded (e.g., by dust), and/or when reflectivity of markers on a tracking element is occluded (e.g., by blood, tissue, dust, bone debris, etc.). If an occluded state is detected, the occlusion detection algorithm alerts the user, for example, by causing a warning message to be displayed on the display device 23, an audible alarm to sound, and/or the generation of tactile feedback (e.g., vibration). The occlusion detection algorithm may also issue a control signal, such as a command to the surgical system 10 to shut off power to or otherwise disable the tool 50. In this manner, the occlusion detection algorithm prevents the tool 50 from damaging the anatomy when the tracking system 40 is not able to track relative positions of the tool 50 and the anatomy.

Step S12 is a trial reduction process in which the first implant (i.e., the tibial component 74) or a trial implant (e.g., a tibial trial) is fitted to the first bone (i.e., the prepared medial tibial pocket feature on the tibia T). The user assesses the fit of the tibial component or the tibial trial and may make any desired adjustments, such as, for example, repeating implant planning and/or bone sculpting to achieve an improved fit.

In step S13, the user plans bone preparation for implanting a second implant on a second bone after preparing the first bone. In a preferred embodiment, the second bone is the femur F, the second implant is the femoral component 72, and bone preparation is planned by selecting a location on a distal end of the femur F where the femoral component 72 will be installed. If the femoral component 72 has been previously planned (e.g., in step S10), the prior placement may be revisited and adjusted if desired.

In step S14, the second bone is prepared to receive the second implant by manipulating the tool 50 to sculpt the second bone. In one embodiment, the femur F is prepared by forming the medial femoral surface, post, and keel features on the distal end of the femur F. Upon installation of the femoral component 72, the medial femoral surface, post, and keel features will mate with a surface 72a, a post 72b, and a keel 72c, respectively, of the femoral component 72 (shown in FIG. 7A). Preparation of the femoral features is substantially similar to the preparation of the medial tibial surface feature.

Step S15 is a trial reduction process in which the second implant (i.e., the femoral component 72) or a trial implant (e.g., a femoral trial) is fitted to the prepared medial femoral surface, post, and keel features on the femur F. The user assesses the fit of the femoral component 72 or the femoral trial and may make any desired adjustments, such as, for example, repeating implant planning and/or bone sculpting to achieve an improved fit. In step S15, adjustments may also be made to the tibia T. When the user is satisfied with the fit of the trial implants, the user may proceed with installation of the femoral component 72 and the tibial component 74 and completion of the surgical procedure.

Thus, embodiments of the present invention can be configured to provide a haptic guidance system and method that may replace direct visualization in minimally invasive surgery, spare healthy bone in orthopedic joint replacement applications, enable intraoperative adaptability and planning, and produce operative results that are sufficiently predictable, repeatable, and/or accurate regardless of surgical skill level.

A method and apparatus for controlling a haptic device are disclosed in U.S. patent application Ser. No. 11/750,815, entitled Method and Apparatus for Controlling a Haptic Device, filed on May 18, 2007, the disclosure of which is hereby incorporated herein by reference in its entirety, U.S. patent application Ser. No. 11/750,840, entitled Method and Apparatus for Controlling a Haptic Device, filed on May 18, 2007, the disclosure of which is hereby incorporated herein by reference in its entirety, and U.S. patent application Ser. No. 11/750,845, entitled Method and Apparatus for Controlling a Haptic Device, filed on May 18, 2007, the disclosure of which is hereby incorporated herein by reference in its entirety.

Other embodiments of the invention will be apparent to those skilled in the art from consideration of the specification and practice of the invention disclosed herein. It is intended that the specification and examples be considered as exemplary only.

What is claimed is:

1. A system for verifying a tool for use in a surgical procedure, the system comprising:
 a mechanical interface configured to be affixed to a portion of a patient's anatomy, wherein the mechanical interface comprises a divot, the divot comprising at least a first portion having a first dimension and a second portion having a second dimension;
 a probe configured to be inserted into the divot of the mechanical interface; and
 a computing system configured to determine a location of a portion of the probe when the probe is inserted into the divot and define a checkpoint location based on the location of the portion of the probe;

wherein the computing system is further configured to verify a surgical tool by comparing the checkpoint location to a location of a portion of the surgical tool when the surgical tool is inserted into the divot and the probe is no longer inserted into the divot.

2. The system of claim 1, wherein the divot has a conical or frustoconical shape.

3. The system of claim 1, wherein:
the surgical tool has a third dimension corresponding to the first dimension such that the surgical tool bottoms out at the first portion of the divot when inserted into the divot; and
the probe has a fourth dimension corresponding to the second dimension such that the probe bottoms out at the second portion of the divot when inserted into the divot.

4. The system of claim 1, wherein the probe has a blunt tip.

5. The system of claim 1, wherein the probe has a sharp tip.

6. The system of claim 1, wherein verifying the surgical tool comprises determining an identity of the surgical tool.

7. The system of claim 1, wherein verifying the surgical tool comprises determining a size of the surgical tool.

8. The system of claim 1, wherein verifying the surgical tool comprises determining that the surgical tool is correctly installed.

9. The system of claim 1, wherein the computing system is configured to determine the location of the portion of the probe or location of the portion of the surgical tool the probe or the surgical tool is received by the divot and engages with and is stopped by the mechanical interface.

10. The system of claim 1, wherein the surgical tool is a burr, a second probe, or a router.

11. The system of claim 1, further comprising a second surgical tool, wherein the computing system is configured to verify the second surgical tool by determining that the second surgical tool has a different identity, shape, size, or configuration than the surgical tool.

12. A method for verifying a surgical tool, the method comprising:
affixing a mechanical interface to a portion of a patient's anatomy;
establishing a checkpoint location associated with the mechanical interface;
inserting a surgical tool a maximum distance into the mechanical interface such that the surgical tool bottoms out in a divot of the mechanical interface; and
comparing the checkpoint location with a position of a portion of the surgical tool when the surgical tool is inserted the maximum distance into the mechanical interface to verify the surgical tool.

13. The method of claim 12, wherein the portion of the surgical tool is a tip of the surgical tool.

14. The method of claim 12, wherein establishing the checkpoint location comprises inserting a probe a second maximum distance into the mechanical interface such that the probe bottoms out in the divot of the mechanical interface and determining a location of a portion of the probe when the probe is inserted into the mechanical interface to the second maximum distance, wherein the second maximum distance is greater than the maximum distance.

15. The method of claim 12, wherein verifying the surgical tool comprises determining an identity of the surgical tool.

16. The method of claim 12, wherein verifying the surgical tool comprises determining a size of the surgical tool.

17. The method of claim 12, wherein verifying the surgical tool comprises determining that the surgical tool is correctly installed.

18. The method of claim 12, further comprising verifying movement of an anatomy tracker, verifying accuracy of the mechanical interface registration, and/or calibrating a guidance system associated with the system by comparing the checkpoint location to the location of the portion of the surgical tool when the surgical tool is inserted the maximum distance into the mechanical interface.

19. The method of claim 12, further comprising positioning a second surgical tool in the mechanical interface and comparing a position of a portion of the second surgical tool with the checkpoint location to verify the second surgical tool.

20. The method of claim 19, wherein verifying the second surgical tool comprises determining that the second surgical tool has a different identity, shape, size, or configuration than the surgical tool.

* * * * *